US008853213B2

(12) United States Patent
Son et al.

(10) Patent No.: US 8,853,213 B2
(45) Date of Patent: Oct. 7, 2014

(54) BICYCLIC COMPOUND FOR MODULATING G PROTEIN-COUPLED RECEPTORS

(75) Inventors: Jung Beom Son, Hwaseong-si (KR); Nam Du Kim, Hwaseong-si (KR); Young Kil Chang, Seoul (KR); Hee Cheol Kim, Yongin-si (KR); Ji Sook Kim, Yeoju-gun (KR); Young Hee Jung, Seoul (KR)

(73) Assignee: Hanmi Pharm. Co., Ltd, Hwaseong-si (KR)

( * ) Notice: Subject to any disclaimer, the term of this patent is extended or adjusted under 35 U.S.C. 154(b) by 0 days.

(21) Appl. No.: 13/997,415

(22) PCT Filed: Dec. 29, 2011

(86) PCT No.: PCT/KR2011/010304
§ 371 (c)(1),
(2), (4) Date: Jun. 24, 2013

(87) PCT Pub. No.: WO2012/093809
PCT Pub. Date: Jul. 12, 2012

(65) Prior Publication Data
US 2013/0274268 A1    Oct. 17, 2013

(30) Foreign Application Priority Data

Jan. 3, 2011    (KR) ........................ 10-2011-0000250

(51) Int. Cl.
*A61K 31/7024*    (2006.01)
*C07D 495/04*    (2006.01)
*C07D 487/04*    (2006.01)

(52) U.S. Cl.
CPC ............ *C07D 495/04* (2013.01); *C07D 487/04* (2013.01)
USPC ........................ 514/252.01; 514/252; 514/160

(58) Field of Classification Search
None
See application file for complete search history.

(56) References Cited

U.S. PATENT DOCUMENTS

2008/0293690 A1    11/2008    Fevig et al.

FOREIGN PATENT DOCUMENTS

| KR | 10-2007-0098907 A | 10/2007 | |
|---|---|---|---|
| WO | 96/35689 A1 | 11/1996 | |
| WO | 97/49706 A1 | 12/1997 | |
| WO | WO 2005066182 | * 7/2005 | ........... C07D 495/04 |
| WO | 2008/137436 A1 | 11/2008 | |
| WO | 2011/159657 A1 | 12/2011 | |

OTHER PUBLICATIONS

Lodish, H. et al, Molecular Cell Biology, 4th Edition, 2000, http://www.ncbi.nlm.nih.gov/books/NBK21718.*
Lefkowitz, Robert J., "Turned on to ill effect," G Protein coupled receptors. Nature, 364, Oct. 14, 1993, p. 603-604.(News and Views).*
Das, et al., The Genetic Basis of Type 2 Diabetes, Cell Science, 2006, Apr. 30, 2 (4): 100-131.*
International Searching Authority, International Search Report for PCT/KR2011/010304 dated Sep. 3, 2012.
European Patent Office, Communication dated May 12, 2014, issued in the European Patent Application No. 11854581.3.
Montgomery, et al., "The Use of Enamines in the Synthesis of Heterocycles (1)", Journal of Heterocyclic Chemistry, Wiley-Blackwell Publishing, Inc., US, vol. 9, No. 5, Oct. 1, 1972, XP 000673524, pp. 1077-1079.

* cited by examiner

*Primary Examiner* — San-Ming Hui
*Assistant Examiner* — Jeanmarie Calvillo
(74) *Attorney, Agent, or Firm* — Sughrue Mion, PLLC

(57) ABSTRACT

The present invention relates to a bicyclic compound for modulating G protein-coupled receptors. The inventive compound provides preventing or treating a disease associated with the modulation of G protein-coupled receptors, particularly GPR119 G protein-coupled receptors.

8 Claims, No Drawings

BICYCLIC COMPOUND FOR MODULATING G PROTEIN-COUPLED RECEPTORS

FIELD OF THE INVENTION

The present invention relates to a novel bicyclic compound for modulating G protein-coupled receptors, particularly GPR119 G protein-coupled receptors, and a pharmaceutical composition comprising the same.

BACKGROUND OF THE INVENTION

Diabetes mellitus, often simply referred to as diabetes, is a group of metabolic diseases in which a person retains high blood sugar for a long period of time, either because the body does not produce enough insulin, or because cells do not respond to the insulin that is produced, or for both reasons. Insulin is a hormone, produced in the beta cells of the pancreas, which causes cells to take up glucose from the blood, using it as an energy source. When insulin does not work properly in the body, the uptake of glucose from the blood to, for example, muscle cells becomes poor, resulting in the accumulation of glucose in the blood and the excretion of sugar in the urine. Continuance of such hyperglycemia for a long period of time causes various complications in the nerves, the kidney, the eye and the heart. Serious complications include lower limb amputation, cardiovascular disease, renal failure, retinal damage, hypertension and myocardial infarction.

Diabetes is one of the major causes of death among adults throughout the world. The number of diabetics has drastically increased along with the increase in the obese population. As of 2010, approximately 360 million people worldwide have diabetes, and the expectation is for approximately 560 million people to have diabetes in 2030.

There are two main types of diabetes. Type 1 diabetes mellitus (also known as insulin-dependent diabetes mellitus) is a chronic autoimmune disease characterized by the extensive loss of the insulin-producing beta cells of the islets of Langerhans in the pancreas (hereinafter referred to as "pancreatic islet cells" or more simply as "islet cells"). As these cells are progressively destroyed, the amount of secreted insulin decreases, the production of insulin decreases finally below the level required for euglycemia, eventually leading to hyperglycemia. Although the exact trigger for this immune response is not known, type 1 diabetes is mainly attributed to autoimmune, genetic and environmental factors. The onset of type 1 diabetes most often occurs before the age of 30. Patients with Type I diabetes have a high level of antibodies to pancreatic beta cells (hereinafter referred to as "beta cells"). However, not all patients with high levels of these antibodies develop type 1 diabetes.

Type II diabetes mellitus (also known as non-insulin-dependent diabetes mellitus) develops when muscle, fat and liver cells fail to respond normally to insulin. This response failure (known as insulin resistance) may be attributed to a decreased number of insulin receptors on these cells, or the dysfunction of the signaling pathway within the cells, or both of these factors. Initially, beta cells increase insulin output to compensate for the insulin resistance. Over time, these cells become unable to produce enough insulin to maintain normal blood glucose levels, resulting in the progression of Type II diabetes (see [Kahn B B, Cell 92:593-596, 1998]; [Cavaghan M K, et al., J. Clin. Invest. 106:329-333, 2000]; [Saltiel A R, Cell 104:517-529, 2001]; [Prentki M and Nolan C J. J Clin Invest. 116:1802-1812. (2006)]; and [Kahn S E. J. Clin. Endicrinol. Metab. 86:4047-4058, 2001]). Fasting hyperglycemia featuring Type II diabetes results from the combination of insulin resistance and beta cell dysfunction (see [UKPDS group, JAMA 281:2005-2012, 1999]; [Levy J, et al., Diabetes Med. 15:290-296, 1998]; and [Zhou Y P, et al., J. Biol. Chem. 278:51316-23, 2003]). Type II diabetes is primarily related to lifestyle factors and genetics. Among the lifestyle factors are obesity, stress, drinking, smoking, frequent pregnancy, and intemperance.

The beta cell defect has two components: the first component, an elevation of basal insulin release (occurring in the presence of low, non-stimulatory glucose concentrations), is observed in obese, insulin-resistant pre-diabetic stages as well as in Type II diabetes. The second component is a failure to increase insulin release above the already elevated basal output in response to a hyperglycemic challenge. This lesion is absent in pre-diabetes and appears to define the transition from normo-glycemic insulin-resistant states to frank diabetes. There is currently no cure for diabetes. Conventional treatments for diabetes are very limited and are focused on attempting to control the blood glucose level in order to minimize or delay complications. Current treatments target either insulin resistance (metformin, thiazolidinediones ("TZDs")), or insulin release from the beta cell (sulphonylureas, exenatide). Sulphonylureas, and other compounds that act by depolarizing the beta cell, have the side effect of hypoglycemia since they cause insulin secretion independent of circulating glucose levels. One approved drug, Byetta (exenatide) stimulates insulin secretion only in the presence of high glucose, but is not orally available and must be injected. Januvia (sitagliptin) is another recently approved drug that increases blood level of incretin hormones, which can increase insulin secretion, reduce glucagon secretion and have other less well-known characterized effects. However, the use of Januvia is restricted in patients with renal problems. Further, Januvia and other dipeptidyl peptidases IV inhibitors may also influence the tissue levels of other hormones and peptides, and the long-term consequences of this broader effect have not been fully investigated. There is an unmet need for oral drugs that stimulate insulin secretion in a glucose dependent manner.

The elevation of beta cell cAMP (cyclic adenosine monophosphate) has a substantial potentiating effect on insulin secretion in the presence of stimulatory levels of glucose (see below). Unfortunately, many potentiators of glucose-stimulated insulin secretion also have effects outside of the islet which limit their use as diabetes therapeutics. For example, the best available selective muscarinic agonists which stimulate insulin secretion also stimulate multiple undesirable responses in multiple tissues (see [Rhoades R A and Tanner G A, eds (2003) Medical Physiology, 2nd ed Lippmcott, Williams and Wilkins. ISBN 0-7817-1936-4]). Likewise, VIP and PACAP receptors are present in multiple organ systems and mediate effects on the reproductive, immune and other diverse systems that make them less attractive as specific enhancers of glucose dependent insulin secretion.

Incretin hormones such as Glucagon-Like Peptide 1 (GLP-1) and Glucose-dependent Insulinotropic Polypeptide ([0011] GIP, also known as Gastric Inhibitory Polypeptide) also bind to specific G alpha s-coupled GPCR receptors on the surface of islet cells, including beta cells, and increase intracellular cAMP (see [Drucker D J, J. Clin. Invest. 2007 January; 117(1):24-32]). Although the receptors for these hormones are present in other cells and tissues, the overall sum of effects of these peptides appears to be beneficial at controlling the glucose metabolism in the organism (see [Hansotia T, et al., J. Clin. Invest. 2007 January; 117(1):143-52. Epub 2006 Dec. 21]). GIP and GLP-1 are produced and secreted from intestinal K and L cells, respectively, and these peptide hormones are released in response to meals by both direct action of nutrients in the gut lumen and neural stimulation resulting from food ingestion. GIP and GLP-1 have short half-lives in circulation in the human body due to the action of the protease dipeptidyl-peptidase IV (DPP-IV), and inhibitors of this protease can lower blood glucose thanks to their ability to raise the levels of active forms of the incretin peptides. The glucose lowering that can be obtained with DPP-IV inhibitors, however, is somewhat limited since these drugs are dependent on the endogenous release of the incretin hormones. Peptides (e.g., exenatide (Byetta)) and peptide-conjugates that bind to the GIP or GLP-1 receptors but are resistant to serum protease cleavage can also lower blood glucose substantially (see [Gonzalez C, et al., *Expert Opin Investig Drugs* 2006 August; 15(8):887-95]), but these incretin mimetics must be injected and tend to induce a high rate of nausea and therefore are not ideal therapies for general use in the Type II diabetic population. The clinical success of DPP4 inhibitors and incretin mimetics, although far from ideal, points to the potential utility of compounds that increase incretin activity in the blood or directly stimulate cAMP in the beta cell. Some studies have indicated that beta cell responsiveness to GIP is diminished in Type II diabetes (see [Nauck M A, et al., *J. Clin. Invest.* 91:301-307 (1993)]; and [Elahi D, et al., *Regul. Pept.* 51:63-74 (1994)]). Restoration of this responsiveness (see [Meneilly G S, et al., *Diabetes Care.* 1993 January; 16(1): 110-4]) may be a promising way to improve beta cell functioning in vivo.

Since increased incretin activity has a positive effect on glucose dependent insulin secretion and other mechanisms that lead to lower blood glucose, interest is also being shown in the exploration of therapeutic approaches to increasing incretin release from intestinal K and L cells. GLP-1 secretion appears to be attenuated in Type II diabetes (see [Vilsboll T, et al., *Diabetes* 50:609-613]), so that an improvement in incretin release may ameliorate this component of metabolic dysregulation. Nutrients such as glucose and fat in the gut lumen prompt incretin secretion by interaction with apical receptors (see [Vilsboll T, et al., *Diabetes* 50:609-613]). GLP-1 and GIP release can also result from neural stimulation; acetylcholine and GRP can enhance incretin release in a manner perhaps analogous to the effects of these neurotransmitters on the beta cell in regard to insulin secretion (see ([Brubaker P, Ann N Y *Acad. Sci.* 2006 July; 1070:10-26]; and [Reimann F, et al., *Diabetes* 2006 December; 55 (Suppl 2):S78-S85]). Somatostatin, leptin and free fatty acids also appear to modulate incretin secretion (see [Brubaker P, Ann N Y *Acad. Sci.* 2006 July; 1070: 10-26]; and [Reimann, F. et al., *Diabetes.* 2006 December; 55(Suppl 2):S78-S85]). However, there does not appear to be a way to selectively impact these pathways to promote incretin secretion for therapeutic benefit.

Many people with diabetes mellitus are obese and they weigh approximately 20% more than the recommended weight for their height and build. Furthermore, obesity is characterized by hyperinsulinemia, insulin resistance, hypertension and atherosclerosis.

Obesity and diabetes are among the most common human health problems in industrialized societies. In industrialized countries a third of the population is at least 20% overweight. As of 2010, the number of obese people amounts to 470 million worldwide, and tends to increase in number every year. Obesity is one of the most important risk factors for diabetes mellitus. Definitions of obesity differ, but as a rule, a subject weighing at least 20% more than the recommended weight for his/her height and build is considered obese. The risk of developing diabetes mellitus is tripled in subjects 30% overweight, and three-quarters of those with diabetes are overweight.

Obesity, which is the result of an imbalance between caloric intake and energy expenditure, is highly correlated with insulin resistance and diabetes in experimental animals and human. However, the molecular mechanisms that are involved in obesity-diabetes syndromes are unclear. During early development of obesity, increased insulin secretion balances insulin resistance and protects patients from hyperglycemia (see [Le Stunff, et al. *Diabetes* 43, 696-702 (1989)]). However, after several decades, β cell function deteriorates and non-insulin-dependent diabetes develops in about 20% of the obese population (see [Pederson, P. *Diab. Metab. Rev.* 5, 505-509 (1989)); and (Brancati, F. L., et al., *Arch. Intern. Med.* 159, 957-963 (1999)). Given its high prevalence in modern societies, obesity has thus become the leading risk factor for NIDDM (see [Hill, J. O., et al., *Science* 280, 1371-1374 (1998)]). However, the factors which predispose a fraction of patients to alteration of insulin secretion in response to fat accumulation remain unknown.

Whether someone is classified as overweight or obese is generally determined on the basis of their body mass index (BMI) which is calculated by dividing body weight (kg) by height squared (m$^2$). Thus, the units of BMI are kg/m$^2$ and it is possible to calculate the BMI range associated with a minimum mortality in each decade of life. Being overweight is defined as a BMI in the range from 25 to 30 kg/m$^2$, and obesity as a BMI greater than 30 kg/m$^2$ (see TABLE below).

| Classification of Weight by Body Mass Index (BMI) | |
|---|---|
| BMI | Classification |
| <18.5 | Underweight |
| 18.5-24.9 | Normal |
| 25.0-29.9 | Overweight |
| 30.0-34.9 | Obesity (Class I) |
| 35.0-39.9 | Obesity (Class II) |
| >40 | Extreme Obesity (Class III) |

A problem with this definition is that it does not take into consideration the ratio of muscle to fat (adipose tissue). Obesity may be also defined on the basis of body fat content (25% and 30% excess in males and females, respectively). As the BMI increases there is an increased risk of death from a variety of causes that are independent of other risk factors. The most common diseases that are accompanied by obesity are cardiovascular disease (particularly hypertension), diabetes (obesity aggravates the development of diabetes), gall bladder disease (particularly cancer) and reproductive diseases. Research has shown that even a modest reduction in body weight can correspond to a significant reduction in the risk of developing coronary heart disease.

Orlistat is a representative commercially available anti-obesity agent. Orlistat (a lipase inhibitor) inhibits fat absorption directly and tends to produce a high incidence of unpleasant side-effects such as diarrhea. Sibutramine (a mixed 5-HT/noradrenaline reuptake inhibitor) can increase blood pressure and heart rate in some patients. The serotonin releaser/reuptake inhibitors fenfluramine and dexfenfluramine were withdrawn due to problems in heart safety. Contrave, Lorcaserin and Qnexa failed to acquire the approval from the FDA because their use was associated with heart abnormalities and oncogenesis. Accordingly, there is a need for the development of a safer anti-obesity agent.

Obesity considerably increases the risk of developing cardiovascular diseases as well. Coronary insufficiency, atheromatous disease, and cardiac insufficiency are at the forefront of the cardiovascular complication induced by obesity. It is estimated that if the entire population had an ideal weight, the risk of coronary insufficiency would decrease by 25% and the risk of cardiac insufficiency and of cerebral vascular accidents by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the relationship between risks factors for diabetes and coronary heart disease and the potential value of an integrated approach to the prevention of these conditions based on the prevention of these conditions based on the prevention of obesity (see [Perry, I. J., et al., *BMJ* 310, 560-564 (1995)]).

Diabetes has also been involved in the development of renal diseases, retinal diseases, and nervous-system problems. Renal disease, also called nephropathy, occurs when the kidney's "filter mechanism" is damaged and an excessive amount of protein leaks into urine leading eventually to kidney failure. Diabetes is also a main cause of damage to the retina at the back of the eye and increases the risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

SUMMARY OF THE INVENTION

Accordingly, it is an object of the present invention to provide a novel bicyclic compound for modulating G protein-coupled receptors, particularly GPR119 G protein-coupled receptors ("GPR119").

It is another object of the present invention to provide a pharmaceutical composition for preventing or treating a disease associated with the modulation of G protein-coupled receptors which comprises the compound as an active ingredient.

In accordance with one aspect of the present invention, there is provided a compound selected from the group consisting of a bicyclic heteroaryl derivative of formula (I), a pharmaceutically acceptable salt thereof, a hydrate thereof, and a solvate thereof:

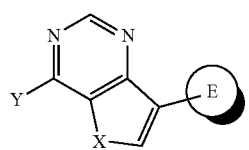

(I)

wherein,

X is S or $NR^1$, $R^1$ is H or $C_{1-4}$ alkyl;

E is $C_{6-14}$ aryl or $C_{2-13}$ heteroaryl, wherein E is optionally substituted with one to three substituents selected from the group consisting of halogen, $-NO_2$, $-CN$, $-CF_3$, $C_{1-6}$ alkyl, $C_{3-8}$ cycloalkyl, $-NH_2$, $C_{1-6}$ alkylamino, $diC_{1-6}$ alkylamino, $C_{1-6}$ alkoxy, $-S-C_{1-6}$ alkyl, $-S(O)_2-C_{1-6}$ alkyl, $-S(O)_2-C_{1-6}$ alkylamino, $-S(O)_2-diC_{1-6}$ alkylamino, $-C(O)-C_{1-6}$ alkyl, carboxyl, $-C(O)_2-C_{1-6}$ alkyl, $-C(O)-C_{1-6}$ alkylamino, $-C(O)-diC_{1-6}$ alkylamino, $C_{6-14}$ aryl, $C_{1-13}$ heteroaryl and $C_{2-13}$ heterocycloalkyl, wherein said substitutents aryl, heteroaryl and heterocycloalkyl are optionally each independently additionally substituted with $C_{1-6}$ alkyl, halogen, $diC_{1-6}$ alkylamino or $C_{1-6}$ alkoxy; and Y is $OR^2$ or $NR^2R^3$, wherein $R^2$ and $R^3$ are each independently H, $-OH$, $C_{1-6}$ alkyl, $C_{3-8}$ cycloalkyl or $C_{4-13}$ heterocycloalkyl, or $R^2$ and $R^3$ are fused with the nitrogen atom to form $C_{2-9}$ heterocycle, and wherein $R^2$ and $R^3$ are optionally substituted with one to three substituents selected from the group consisting of $C_{1-6}$ alkyl, $C_{1-6}$ alkoxy, $-C(O)-C_{1-6}$ alkyl, $-C(O)-C_{6-14}$ aryl, $-C(O)-C_{1-13}$ heteroaryl, $-C(O)_2-C_{1-6}$ alkyl, $-C(O)_2-C_{6-14}$ aryl, $-C(O)_2-C_{1-13}$ heteroaryl, $-C(O)-C_{1-6}$ alkylamino, $-C(O)-diC_{1-6}$ alkylamino, $C_{3-8}$ cycloalkyl, $C_{3-13}$ heterocycloalkyl, $C_{6-14}$ aryl and $C_{1-13}$ heteroaryl, wherein said substituents aryl, heteroaryl, cycloalkyl and heterocycloalkyl are optionally each independently additionally substituted with $C_{1-6}$ alkyl, halogen, $diC_{1-6}$ alkylamino, $C_{1-6}$ alkoxy, $C_{3-8}$ cycloalkyl or $C_{6-14}$ aryl.

In accordance with another aspect of the present invention, there is provided a pharmaceutical composition for preventing or treating a disease associated with the modulation of G protein-coupled receptors, which composition comprises the compound of claim 1 as an active ingredient.

DETAILED DESCRIPTION OF THE INVENTION

In a preferred embodiment of the present invention, preferably E is pyrrolyl, imidazolyl, pyrazolyl, phenyl, pyridinyl, or pyrimidinyl, and wherein E is optionally substituted with one to three substituents selected from the group consisting of halogen, $-NO_2$, $-CN$, $-CF_3$, $C_{1-6}$ alkyl, $C_{3-8}$ cycloalkyl, $-NH_2$, $C_{1-6}$ alkylamino, $diC_{1-6}$ alkylamino, $C_{1-6}$ alkoxy, $-S-C_{1-6}$ alkyl, $-S(O)_2-C_{1-6}$ alkyl, $-S(O)_2-C_{1-6}$ alkylamino, $-S(O)_2-diC_{1-6}$ alkylamino, $-C(O)-C_{1-6}$ alkyl, carboxyl, $-C(O)_2-C_{1-6}$ alkyl, $-C(O)-C_{1-6}$ alkylamino, $-C(O)-diC_{1-6}$ alkylamino, $C_{6-14}$ aryl, $C_{1-13}$ heteroaryl and $C_{2-13}$ heterocycloalkyl.

Preferably, said aryl is phenyl, said heteroaryl is pyrrolyl, imidazolyl, pyrazolyl, tetrazolyl, oxadiazolyl, thiazolyl, pyridinyl or pyrimidinyl, and said heterocycloalkyl is pyrrolidinyl, piperidinyl, piperazinyl, or morpholinyl, and wherein said aryl, heteroaryl and heterocycloalkyl are optionally each independently additionally substituted with $C_{1-6}$alkyl, halogen, $diC_{1-6}$alkylamino or $C_{1-6}$alkoxy.

Further, in a preferred embodiment of the present invention, Y is $OR^2$ or $NR^2R^3$, wherein $R^2$ and $R^3$ are each independently H, $-OH$, $C_{1-6}$ alkyl, $C_{1-6}$ alkoxy, $C_{3-8}$ cycloalkyl, pyrrolidinyl or piperidinyl, $R^2$ and $R^3$ are fused with the nitrogen atom which is combined with $R^2$ and $R^3$ to form pyrrolidinyl, morpholinyl, piperidinyl or piperazinyl, and $R^2$ and $R^3$ are optionally each independently substituted with one to three substituents selected from the group consisting of $C_{1-6}$ alkyl, $C_{1-6}$ alkoxy, $-C(O)-C_{1-6}$ alkyl, $-C(O)-C_{6-14}$ aryl, $-C(O)-C_{1-13}$ heteroaryl, $-C(O)_2-C_{1-6}$ alkyl, $-C(O)_2-C_{6-14}$ aryl, $-C(O)_2-C_{1-13}$ heteroaryl, $-C(O)-C_{1-6}$ alkylamino, $-C(O)-diC_{1-6}$ alkylamino, $C_{3-8}$ cycloalkyl, $C_{3-13}$ heterocycloalkyl, $C_{6-14}$ aryl and $C_{1-13}$ heteroaryl.

Preferably, said aryl is phenyl, said heteroaryl is pyrrolyl, imidazolyl, pyrazolyl, triazolyl, tetrazolyl, oxadiazolyl, thiazolyl, pyridinyl or pyrimidinyl, and said heterocycloalkyl is pyrrolidinyl, piperidinyl, piperazinyl, or morpholinyl, and wherein said aryl, heteroaryl and heterocycloalkyl are optionally each independently additionally substituted with $C_{1-6}$ alkyl, halogen, $diC_{1-6}$ alkylamino, $C_{1-6}$ alkoxy, $C_{3-8}$ cycloalkyl or $C_{6-14}$ aryl.

As used herein, the terms "heteroaryl" and "heterocycloalkyl" refer to aromatic and non-aromatic cyclic compounds containing 1 to 4 heteroatoms selected from the group consisting of O, S and N in its ring backbone, respectively, unless otherwise stated.

As used herein, the term "heterocycle" refers to aromatic or non-aromatic cyclic compounds containing 1 to 4 heteroatoms selected from the group consisting of O, S and N in its ring backbone, unless otherwise stated.

Most preferred examples of the inventive compound of formula (I) are as follows. A pharmaceutically acceptable salt, a hydrate and a solvate thereof are also included in the scope of the present invention:

1) 3-cyclopropyl-5-(1-(7-(4-methanesulfonyl-phenyl)thieno[3,2-d]pyrimidin-4-yl)piperidin-4-yl)-1,2,4-oxadiazole;
2) 7-(4-methanesulfonyl-phenyl)-4-(pyrrolidin-1-yl)thieno[3,2-d]pyrimidine;
3) 7-(4-methanesulfonyl-phenyl)-4-(piperidin-1-yl)thieno[3,2-d]pyrimidine;
4) 3-ethyl-5-(1-(7-(4-methanesulfonyl-phenyl)thieno[3,2-d]pyrimidin-4-yl)piperidin-4-yl)-1,2,4-oxadiazole;
5) 3-isopropyl-5-(1-(7-(4-methanesulfonyl-phenyl)thieno[3,2-d]pyrimidin-4-yl)piperidin-4-yl)-1,2,4-oxadiazole;
6) 3-cyclopentyl-5-(1-(7-(4-methanesulfonyl-phenyl)thieno[3,2-d]pyrimidin-4-yl)piperidin-4-yl)-1,2,4-oxadiazole;
7) 3-cyclohexyl-5-(1-(7-(4-methanesulfonyl-phenyl)thieno[3,2-d]pyrimidin-4-yl)piperidin-4-yl)-1,2,4-oxadiazole;
8) 5-(1-(7-(4-(methanesulfonylphenyl)phenyl)thieno[3,2-d]pyrimidin-4-yl)piperidin-4-yl)-3-phenyl-1,2,4-oxadiazole;
9) 3-isopropyl-5-(4-(7-(4-methanesulfonyl-phenyl)thieno[3,2-d]pyrimidin-4-yl)piperazin-1-yl)-1,2,4-oxadiazole;
10) tert-butyl 4-(7-(4-methanesulfonyl-phenyl)thieno[3,2-d]pyrimidin-4-yl)piperazin-1-carboxylate;
11) 4-(4-(5-ethylpyrimidin-2-yl)piperazin-1-yl)-7-(4-methanesulfonyl-phenyl)thieno[3,2-d]pyrimidine;
12) 7-(2-fluoro-4-methanesulfonyl-phenyl)-4-[4-(3-isopropyl-[1,2,4]oxadiazol-5-yl)-piperidin-4-yl]-thieno[3,2-d]pyrimidine;
13) 7-(3-fluoro-4-methanesulfonyl-phenyl)-4-[4-(3-isopropyl-[1,2,4]oxadiazol-5-yl)-piperidin-4-yl]-thieno[3,2-d]pyrimidine;
14) 4-[4-(3-isopropyl-[1,2,4]oxadiazol-5-yl)-piperidin-1-yl]-7-(4-nitro-phenyl)-thieno[3,2-d]pyrimidine;
15) 4-{4-[4-(3-isopropyl-[1,2,4]oxadiazol-5yl)-piperidin-1-yl]-thieno[3,2-d]pyrimidin-7-yl}-benzoic acid;
16) 4-{4-[4-(3-isopropyl-[1,2,4]oxadiazol-5yl)-piperidin-1-yl]-thieno[3,2-d]pyrimidin-7-yl}-benzoic acid methyl ester;
17) 4-[4-(3-tert-butyl-[1,2,4]oxadiazol-5yl)-piperidin-1-yl]-7-(2-fluoro-4-methanesulfonyl-phenyl)-thieno[3,2-d]pyrimidine;
18) 4-[4-(3-cyclopropyl-[1,2,4]oxadiazol-5yl)-piperidin-1-yl]-7-(2-fluoro-4-methanesulfonyl-phenyl)-thieno[3,2-d]pyrimidine;
19) 4-[4-(3-cyclopentyl-[1,2,4]oxadiazol-5yl)-piperidin-1-yl]-7-(2-fluoro-4-methanesulfonyl-phenyl)-thieno[3,2-d]pyrimidine;
20) 4-[4-(3-isopropyl-[1,2,4]oxadiazol-5yl)-piperidin-1-yl]-7-(4-(propylsulfonyl)phenyl)-thieno[3,2-d]pyrimidine;
21) 7-(4-(cyclopropylsulfonyl)phenyl)-4-[4-(3-isopropyl-[1,2,4]oxadiazol-5-yl)-piperidin-1-yl]-thieno[3,2-d]pyrimidine;
22) 4-[4-(3-isopropyl-[1,2,4]oxadiazol-5yl)-piperidin-1-yl]-7-(4-(isopropylsulfonyl)phenyl)-thieno[3,2-d]pyrimidine;
23) 7-(4-(cyclopentylsulfonyl)phenyl)-4-[4-(3-isopropyl-[1,2,4]oxadiazol-5-yl)-piperidin-1-yl]-thieno[3,2-d]pyrimidine;
24) 7-4-(2-fluoro-(4-propylsulfonyl)phenyl)-4-[4-(3-isopropyl-[1,2,4]oxadiazol-5-yl)-piperidin-1-yl]-thieno[3,2-d]pyrimidine;
25) tert-butyl 4-(5-methyl-7-(4-methanesulfonyl-phenyl)-5H-pyrrolo[3,2-d]pyrimidin-4-yloxy)piperidin-1-carboxylate;
26) 5-methyl-7-(4-methanesulfonyl-phenyl)-4-(piperidin-4-yloxy)-5H-pyrrolo[3,2-d]pyrimidine;
27) 4-(1-(5-ethylpyrimidin-2-yl)piperidin-4-yloxy)-5-methyl-7-(4-methanesulfonyl-phenyl)-5H-pyrrolo[3,2-d]pyrimidine;
28) 5-methyl-7-(4-methanesulfonyl-phenyl)-4-(1-(5-(trifluoromethyl)pyrimidin-2-yl)piperidin-4-yloxy)-5H-pyrrolo[3,2-d]pyrimidine;
29) 4-(1-(5-ethylpyrimidin-2-yl)piperidin-4-yloxy)-7-(2-fluoro-4-methanesulfonyl-phenyl)-5-methyl-5H-pyrrolo[3,2-d]pyrimidine;
30) 7-(2-fluoro-4-(methanesulfonyl(phenyl)-5-methyl-4-(1-(5-propylpyrimidin-2-yl)piperidin-4-yloxy)-5H-pyrrolo[3,2-d]pyrimidine;
31) 7-(2-fluoro-4-methanesulfonyl-phenyl)-5-methyl-4-(1-(5-(trifluoromethyl)pyrimidin-2-yl)piperidin-4-yloxy)-5H-pyrrolo[3,2-d]pyrimidine;
32) 5-ethyl-4-(1-(5-ethylpyrimidin-2-yl)piperidin-4-yloxy)-7-(4-methanesulfonyl-phenyl)-5H-pyrrolo[3,2-d]pyrimidine;
33) 5-ethyl-4-(1-(5-ethylpyrimidin-2-yl)piperidin-4-yloxy)-7-(2-fluoro-4-methanesulfonyl-phenyl)-5H-pyrrolo[3,2-d]pyrimidine;
34) 5-ethyl-7-(2-fluoro-4-methanesulfonyl-phenyl)-4-(1-(5-propylpyrimidin-2-yl)piperidin-4-yloxy)-5H-pyrrolo[3,2-d]pyrimidine;
35) 3-isopropyl-5-(4-(5-methyl-7-(4-methanesulfonyl-phenyl)-5H-pyrrolo[3,2-d]pyrimidin-4-yloxy)piperidin-1-yl)-1,2,4-oxadiazole;
36) 5-(4-(7-(2-fluoro-4-methanesulfonyl-phenyl)-5-methyl-5H-pyrrolo[3,2-d]pyrimidin-4-yloxy)piperidin-1-yl)-3-isopropyl-1,2,4-oxadiazole;
37) 5-(4-(5-ethyl-7-(2-fluoro-4-methanesulfonyl-phenyl)-5H-pyrrolo[3,2-d]pyrimidin-4-yloxy)piperidin-1-yl)-3-isopropyl-1,2,4-oxadiazole;
38) 4-[1-(3-isopropyl-[1,2,4]oxadiazol-5-yl)-pyrrolidin-3-yloxy]-7-(4-methanesulfonyl-phenyl)-5-methyl-5H-pyrrolo[3,2-d]pyrimidine;
39) 4-[1-(5-ethyl-pyrimidin-2-yl)-pyrrolidin-3-yloxy]-7-)4-methanesulfonyl-phenyl)-5-methyl-5H-pyrrolo[3,2-d]pyrimidine;
40) 4-[7-(4-methanesulfonyl-phenyl)-5-methyl-5H-pyrrolo[3,2-d]pyrimidin-4-yloxy]piperidin-1-carboxylic acid tert-butylamide;
41) 4-(4-(1-(3-isopropyl-1,2,4-oxadiazol-5-yl)piperidin-4-yloxy)-5-methyl-5H-pyrrolo[3,2-d]piperidin-7-yl)benzeneamine;
42) 3-isopropyl-5-(4-(5-methyl-7-(4-nitrophenyl)-5H-pyrrolo[3,2-d]pyrimidin-4-yloxy)piperidin-1-yl)-1,2,4-oxadiazole;
43) 4-{4-[1-(5-ethylpyrimidin-2-yl)-piperidin-4-yloxy]-5-methyl-5H-pyrrolo[3,2-d]pyrimidin-7-yl}-benzonitrile;
44) 1-(4-{4-[1-(5-ethylpyrimidin-2-yl)-piperidin-4-yloxy]-5-methyl-5H-pyrrolo[3,2-d]pyrimidin-7-yl}-phenyl)-ethanone;
45) 4-(1-isopropyl-piperidin-4-yloxy)-7-(4-methanesulfonyl-phenyl)-5-methyl-5H-pyrrolo[3,2-d]pyrimidine;

46) 1-{4-[7-(4-methanesulfonyl-phenyl)-5-methyl-5H-pyrrolo[3,2-d]pyrimidin-4-yloxy]-piperidin-1-yl}-2,2-dimethynyl-propan-1-one;
47) tert-butyl 4-(7-(6-fluoropyridin-3-yl)-5-methyl-5H-pyrrolo[3,2-d]pyrimidin-4-yloxy)piperidin-1-carboxylate;
48) 4-(1-(5-ethylpyrimidin-2-yl)piperidin-4-yloxy)-7-(6-fluoropyridin-3-yl)-5-methyl-5H-pyrrolo[3,2-d]pyrimidine;
49) 4-((1-(5-ethylpyrimidin-2-yl)piperidin-4-yl)methoxy)-5-methyl-7-(4-methanesulfonyl-phenyl)-5H-pyrrolo[3,2-d]pyrimidine;
50) tert-butyl 4-(7-(4-methanesulfonyl-phenyl)thieno[3,2-d]pyrimidin-4-yloxy)piperidin-1-carboxylate;
51) 3-isopropyl-5-(4-(5-methyl-7-(4-methanesulfonyl-phenyl)-5H-thieno[3,2-d]pyrimidin-4-yloxy)piperidin-1-yl)-1,2,4-oxadiazole;
52) 3-(cyclopropylmethyl)-5-(4-(7-(4-methanesulfonyl-phenyl)thieno[3,2-d]pyrimidin-4-yloxy)piperidin-1-yl)-1,2,4-oxadiazole;
53) 3-tert-butyl-5-(4-(7-(4-methanesulfonyl-phenyl)thieno[3,2-d]pyrimidin-4-yloxy)piperidin-1-yl)-1,2,4-oxadiazole;
54) 3-cyclobutyl-5-(4-(7-(4-methanesulfonyl-phenyl)thieno[3,2-d]pyrimidin-4-yloxy)piperidin-1-yl)-1,2,4-oxadiazole;
55) 4-(1-(5-ethylpyrimidin-2-yl)piperidin-4-yloxy)-7-(4-methanesulfonyl-phenyl)thieno[3,2-d]pyrimidine;
56) 4-[1-(5-cyclopropyl-pyrimidin-2-yl)-piperidin-4-yloxy]-7-(4-methanesulfonyl-phenyl)-thieno[3,2-d]pyrimidine;
57) 4-[1-(5-ethyl-pyrimidin-2-yl)-pyrrolidin-3-yloxy]-7-(4-methanesulfonyl-phenyl)-thieno[3,2-d]pyrimidine;
58) 4-[1-(3-isopropyl-[1,2,4]oxadiazol-5-yl)-pyrrolidin-3-yloxy]-7-(4-methanesulfonyl-phenyl)-thieno[3,2-d]pyrimidine;
59) 7-(4-((methanesulfonyl)phenyl)-4-(1-(4-(trifluoromethyl)pyrimidin-2-yl)piperidin-4-yloxy)thieno[3,2-d]pyrimidine;
60) 7-(2-fluoro-4-methanesulfonyl-phenyl)-4-[1-(3-isopropyl-[1,2,4]oxadiazol-5-yl)piperidin-4-yloxy]thieno[3,2-d]pyrimidine;
61) 3-ethyl-5-(4-(7-(2-fluoro-4-methanesulfonyl-phenyl)thieno[3,2-d]pyrimidin-4-yloxy)piperidin-1-yl)-1,2,4-oxadiazole;
62) 3-sec-butyl-5-(4-(7-(2-fluoro-4-methanesulfonyl-phenyl)thieno[3,2-d]pyrimidin-4-yloxy)piperidin-1-yl)-1,2,4-oxadiazole;
63) 7-(2-fluoro-4-methanesulfonyl-phenyl)-4-[1-(3-cyclopropyl-[1,2,4]oxadiazol-5-yl)piperidin-4-yloxy]thieno[3,2-d]pyrimidine;
64) 5-(4-(7-(2-fluoro-4-methanesulfonyl-phenyl)thieno[3,2-d]pyrimidin-4-yloxy)piperidin-1-yl)-3-phenyl-1,2,4-oxadiazole;
65) 5-(4-(7-(2-fluoro-4-methanesulfonyl-phenyl)thieno[3,2-d]pyrimidin-4-yloxy)piperidin-1-yl)-3-(4-fluorophenyl)-1,2,4-oxadiazole;
66) 5-(4-(7-(2-fluoro-4-methanesulfonyl-phenyl)thieno[3,2-d]pyrimidin-4-yloxy)piperidin-1-yl)-3-(pyridin-4-yl)-1,2,4-oxadiazole;
67) 5-(4-(7-(2-fluoro-4-methanesulfonyl-phenyl)thieno[3,2-d]pyrimidin-4-yloxy)piperidin-1-yl)-3-(pyridin-3-yl)-1,2,4-oxadiazole;
68) 5-(4-(7-(2-fluoro-4-methanesulfonyl-phenyl)thieno[3,2-d]pyrimidin-4-yloxy)piperidin-1-yl)-3-(pyrazin-2-yl)-1,2,4-oxadiazole;
69) 7-(2-fluoro-4-methanesulfonyl-phenyl)-4-[1-(3-cyclopropylmethyl-[1,2,4]oxadiazol-5-yl)piperidin-4-yloxy]thieno[3,2-d]pyrimidine;
70) 7-(2-fluoro-4-methanesulfonyl-phenyl)-4-[1-(3-cyclopentyl-[1,2,4]oxadiazol-5-yl)piperidin-4-yloxy]thieno[3,2-d]pyrimidine;
71) 7-(2-fluoro-4-methanesulfonyl-phenyl)-4-[1-(3-t-butyl-[1,2,4]oxadiazol-5-yl)piperidin-4-yloxy]thieno[3,2-d]pyrimidine;
72) tert-butyl 4-(7-(2-fluoro-4-methanesulfonyl-phenyl)thieno[3,2-d]pyrimidin-4-yloxy)piperidin-1-carboxylate;
73) isopropyl 4-(7-(2-fluoro-4-methanesulfonyl-phenyl)thieno[3,2-d]pyrimidin-4-yloxy)piperidine-1-carboxylate;
74) 7-(2-fluoro-4-methanesulfonyl-phenyl)-4-[1-methylpiperidin-4-yloxy]thieno[3,2-d]pyrimidine;
75) 4-(7-(2-fluoro-4-methanesulfonyl-phenyl)thieno[3,2-d]pyrimidin-4-yloxy)piperidin-1-carbonitrile;
76) 7-(2-fluoro-4-methanesulfonyl-phenyl)-4-[piperidin-4-yloxy]thieno[3,2-d]pyrimidine;
77) 2-(4-(7-(2-fluoro-4-methanesulfonyl-phenyl)thieno[3,2-d]pyrimidin-4-yloxy)piperidin-1-yl)benzo[d]oxazole;
78) 7-(2-fluoro-4-methanesulfonyl-phenyl)-4-[1-(3-isobutyl-[1,2,4]oxadiazol-5-yl)piperidin-4-yloxy]thieno[3,2-d]pyrimidine;
79) 7-(2-fluoro-4-methanesulfonyl-phenyl)-4-[1-(3-cyclohexyl-[1,2,4]oxadiazol-5-yl)piperidin-4-yloxy]thieno[3,2-d]pyrimidine;
80) 7-(2-fluoro-4-methanesulfonyl-phenyl)-4-[1-(3-bicyclo[2,2,1]heptan-2-yl[1,2,4]oxadiazol-5-yl)piperidin-4-yloxy]thieno[3,2-d]pyrimidine;
81) 4-[1-(5-ethyl-pyrimidin-2-yl)-piperidin-4-yloxy]-7-(2-fluoro-4-methanesulfonyl-phenyl)-thieno[3,2-d]pyrimidine;
82) 7-(2-fluoro-4-methanesulfonyl-phenyl)-4-[1-(5-trifluoromethyl-pyrimidin-2-yl)-piperidin-4-yloxy]-thieno[3,2-d]pyrimidine;
83) 7-(2-fluoro-4-methanesulfonyl-phenyl)-4-[1-(5-propyl-pyrimidin-2-yl)-piperidin-4-yloxy]-thieno[3,2-d]pyrimidine;
84) 7-(2-fluoro-4-methanesulfonyl-phenyl)-4-[1-(5-cyclopropyl-pyrimidin-2-yl)-piperidin-4-yloxy]-thieno[3,2-d]pyrimidine;
85) 7-(2-fluoro-4-methanesulfonyl-phenyl)-4-(1-pyrimidin-2-yl-piperidin-4-yloxy)-thieno[3,2-d]pyrimidine;
86) 7-(2-fluoro-4-methanesulfonyl-phenyl)-4-{1-[5-(4-isopropylphenyl)-pyrimidin-2-yl)-piperidin-4-yloxy]-thieno[3,2-d]pyrimidine;
87) 1-(4-(7-(2-fluoro-4-methanesulfonyl-phenyl)thieno[3,2-d]pyrimidin-4-yloxy)piperidin-1-yl)ethanone;
88) 1-(4-(7-(2-fluoro-4-methanesulfonyl-phenyl)thieno[3,2-d]pyrimidin-4-yloxy)piperidin-1-yl)-2,2-dimethylpropan-1-one;
89) {4-[7-(2-fluoro-4-methanesulfonyl-phenyl)-thieno[3,2-d]pyrimidin-4-yloxy]-piperidin-1-yl}phenyl-methanone;
90) {4-[7-(2-fluoro-4-methanesulfonyl-phenyl)-thieno[3,2-d]pyrimidin-4-yloxy]-piperidin-1-yl}pyridin-3-yl-methanone;
91) 4-(1-benzylpiperidin-4-yloxy]-7-(2-fluoro-4-methanesulfonyl-phenyl) thieno[3,2-d]pyrimidine;
92) 4-(4-bromo-1-benzyl-piperidin-4-yloxy]-7-(2-fluoro-4-methanesulfonyl-phenyl)thieno[3,2-d]pyrimidine;
93) 7-(2-fluoro-4-methanesulfonyl-phenyl)-4-[1-(4-isopropyl-thiazol-2-yl)piperidin-4-yloxy]-thieno[3,2-d]pyrimidine;
94) 7-(2-fluoro-4-methanesulfonyl-phenyl)-4-(1-(2-isopropyl-2H-tetrazol-5-yl)piperidin-4-yloxy)thieno[3,2-d]pyrimidine;

95) 7-(2-fluoro-4-methanesulfonyl-phenyl)-4[1-(5-isopropyl-[1,2,4]oxadiazol-3-yl)-piperidin-4-yloxy]-thieno[3,2-d]pyrimidine;
96) 5-(4-(7-(2-chloro-4-methoxyphenyl)thieno[3,2-d]pyrimidin-4-yloxy)piperidin-1-yl)-3-isopropyl-1,2,4-oxadiazole;
97) 4-[1-(3-isopropyl-[1,2,4]oxadiazol-5yl)-piperidin-4-yloxy]-7-(2,3,4-trifluoro-phenyl)-thieno[3,2-d]pyrimidine;
98) 7-(3-fluoro-4-methoxy-phenyl)-4-[1-(3-isopropyl-[1,2,4]oxadiazol-5-yl)-piperidin-4-yloxy]-thieno[3,2-d]pyrimidine;
99) 4-[1-(3-isopropyl-[1,2,4]oxadiazol-5yl)-piperidin-4-yloxy]-7-(4-trifluoromethoxy-phenyl)-thieno[3,2-d]pyrimidine;
100) 4-[1-(3-isopropyl-[1,2,4]oxadiazol-5yl)-piperidin-4-yloxy]-7-(4-trifluoromethylsulfanyl-phenyl)-thieno[3,2-d]pyrimidine;
101) 7-(2-fluoro-4-trifluoro(methanesulfonyl)phenyl)-4-[1-(3-isopropyl-[1,2,4]oxadiazol-5-yl)-piperidin-4-yloxy]-thieno[3,2-d]pyrimidine;
102) 4-{4-[1-(3-isopropyl-[1,2,4]oxadiazol-5yl)-piperidin-4-yloxy-]thieno[3,2-d]pyrimidin-7-yl}-benzoic acid methyl ester;
103) 1-(4-{4-[1-(3-isopropyl-[1,2,4]oxadiazol-5yl)-piperidin-4-yloxy]-thieno[3,2-d]pyrimidin-7-yl}-phenyl)-ethanone;
104) 7-(4-cyclopropylsulfonyl-phenyl)-4-[1-(3-isopropyl-[1,2,4]oxadiazol-5yl)-piperidin-4-yloxy]-thieno[3,2-d]pyrimidine;
105) 4-[1-(3-isopropyl-[1,2,4]oxadiazol-5yl)-piperidin-4-yloxy]-7-(4-isopropylsulfonyl-phenyl)-thieno[3,2-d]pyrimidine;
106) 4-[1-(3-isopropyl-[1,2,4]oxadiazol-5yl)-piperidin-4-yloxy]-7-(4-propylsulfonyl-phenyl)-thieno[3,2-d]pyrimidine;
107) 7-(2-fluoro-(4-propylsulfonyl)-phenyl)-4-[1-(3-isopropyl-[1,2,4]oxadiazol-5-yl)-piperidin-4-yloxy]-thieno[3,2-d]pyrimidine;
108) 7-(4-cyclopentylsulfonyl-phenyl)-4-[1-(3-isopropyl-[1,2,4]oxadiazol-5-yl)-piperidin-4-yloxy]-thieno[3,2-d]pyrimidine;
109) tert-butyl 4-(7-(4-methanesulfonyl-phenyl)thieno[3,2-d]pyrimidin-4-ylamino)piperidin-1-carboxylate;
110) 7-(4-methanesulfonyl-phenyl)-N-(piperidin-4-yl)thieno[3,2-d]pyrimidin-4-amine;
111) N-(1-(5-ethylpyrimidin-2-yl)piperidin-4-yl)-7-(4-methanesulfonyl-phenyl)thieno[3,2-d]pyrimidin-4-amine;
112) tert-butyl 4-(methyl(7-(4-methanesulfonyl-phenyl)thieno[3,2-d]pyrimidin-4-yl)amino)piperidin-1-carboxylate;
113) N-(1-(5-isopropyl-1,2,4-oxadiazol-3-yl)piperidin-4-yl)-N-methyl-7-(4-methanesulfonyl-phenyl)thieno[3,2-d]pyrimidin-4-amine;
114) [1-(5-ethylpyrimidin-2-yl)-piperidin-4-yl]-[7-(4-methanesulfonyl-phenyl)-thieno[3,2-d]pyrimidin-4-yl]-methylamine;
115) ethyl-[7-(4-methanesulfonyl-phenyl)-thieno[3,2-d]pyrimidin-4-yl]-(5'-trifluoromethyl-3,4,5,6-tetrahydro-2H-[1,2']bipyridinyl-4-yl)amine;
116) tert-butyl 4-(5-methyl-7-(4-methanesulfonyl-phenyl)-5H-pyrrolo[3,2-d]pyrimidin-4-ylamino)piperidin-1-carboxylate;
117) 3-isopropyl-5-(1-(5-methyl-7-(4-methanesulfonyl-phenyl)-5H-pyrrolo[3,2-d]pyrimidin-4-yl)piperidin-4-yl)-1,2,4-oxadiazole;
118) 5-(1-(7-(4-(1H-tetrazol-1-yl)phenyl)thieno[3,2-d]pyrimidin-4-yl)piperidin-4-yl)-3-isopropyl-1,2,4-oxadiazole;
119) 5-(4-(7-(4-(1H-1,2,4-triazol-1-yl)phenyl)thieno[3,2-d]pyrimidin-4-yloxy)piperidin-1-yl)-3-tert-butyl-1,2,4-oxadiazole;
120) tert-butyl 4-(7-(4-(1H-tetrazol-1-yl)phenyl)-5-methyl-5H-pyrrolo[3,2-d]pyrimidin-4-yloxy)piperidin-1-carboxylate;
121) 4-(4-(1-(5-ethylpyrimidin-2-yl)piperidin-4-yloxy)-5-methyl-5H-pyrrolo[3,2-d]pyrimidin-7-yl)benzeneamine;
122) 7-(4-(1H-tetrazol-1-yl)phenyl)-4-(1-(5-ethylpyrimidin-2-yl)piperidin-4-yloxy)-5-methyl-5H-pyrrolo[3,2-d]pyrimidine;
123) 7-(4-(1H-tetrazol-1-yl)phenyl)-5-methyl-4-(1-(5-(trifluoromethyl)pyrimidin-2-yl)piperidin-4-yloxy)-5H-pyrrolo[3,2-d]pyrimidine;
124) (S)-tert-butyl 3-[5-methyl-7-(4-amino-phenyl)-5H-pyrrolo[3,2-d]pyrimidin-4-yloxy)pyrrolidin-1-carboxylate; and
125) (S)-tert-butyl 3-[5-methyl-7-(4-tetrazol-1-yl-phenyl)-5H-pyrrolo[3,2-d]pyrimidin-4-yloxy)pyrrolidin-1-carboxylate.

The compound of formula (I) according to the present invention may be prepared by any one of conventionally known methods.

The pharmaceutically acceptable salt of the inventive compound of formula (I) also may be prepared based on conventionally known methods, and it may be preferably salts with inorganic or organic acids.

The novel compound of formula (I) according to the present invention, the pharmaceutically acceptable salt thereof, the hydrate thereof, and the solvate thereof are useful for therapy and prophylaxis of diseases associated with the modulation of G protein-coupled receptors, particularly GPR119 G protein-coupled receptors ("GPR119"), such as obesity, metabolic syndrome, and diabetes. Functioning to elevate the intracellular level of cyclic AMP (cAMP), in addition, the compounds according to the present invention can be used to stimulate the secretion of insulin, glucagon-like peptide I (GLP-1), and glucose-dependent insulinotropic polypeptide (GIP) in mammals, particularly humans. Furthermore, compounds of the present invention can reduce blood glucose levels when administered to a subject in need thereof. The expression of GPR119 in the pancreas, the small intestine, the colon and adipose tissue reveals the potential utility of the compounds of the present invention in therapy for obesity and diabetes.

Accordingly, the present invention provides a use of the compound selected from the group consisting of the compound of formula (I), the pharmaceutically acceptable salt thereof, the hydrate thereof, and the solvate thereof for the manufacture of a medicament for preventing or treating diseases associated with the modulation of G protein-coupled receptors, particularly GPR119 G protein-coupled receptors.

In addition, the present invention provides a pharmaceutical composition for preventing or treating diseases associated with the modulation of G protein-coupled receptors, particularly GPR119 G protein-coupled receptors, which comprises the inventive compound as an active ingredient.

Further, the present invention provides a method for preventing or treating diseases associated with the modulation of G protein-coupled receptors, particularly GPR119 G protein-coupled receptors, which comprises administering the inventive compound to a mammal in need thereof.

Concrete examples of the diseases associated with the modulation of GPR119 G protein-coupled receptors include diabetes, hyperglycemia, glucose tolerance impairment, insulin resistance, hyperinsulinemia, retinopathy, neuropathy, nephropathy, retarded wound healing, atherosclerosis and a sequela thereof, abnormal heart function, myocardial ischemia, stroke, metabolic syndrome, hypertension, obesity, dyslipidemia, hyperlipidemia, hypertriglyceridemia, hypercholesterolemia, low HDL, high HDL, non-cardiac ischemia, infection, cancer, restenosis, pancreatitis, neuropathic diseases, lipid disorders, cognitive dysfunction and dementia, cerebropathy, HIV protease-associated lipodystrophy, and glaucoma, but are not limited thereto.

Also, the inventive pharmaceutical composition comprises the compound of formula (I), its pharmaceutically acceptable salt, its solvate, or its hydrate as an active ingredient. It may be formulated with a pharmaceutical acceptable carrier, adjuvant or excipient, in accordance with any of the conventional methods in the form of tablets, capsules, troches, aqueous solutions or suspensions for oral administration or parenteral administration.

The excipient employed in the pharmaceutical composition of the present invention comprises a sweetening agent, a binder, a dissolvent, a dissolving adjuvant, a wetting agent, an emulsifier, an isotonic agent, an adsorption agent, a disintegrating agent, an antioxidant, a preservative, a lubricant, a filler, a freshener, and the like. Representative examples of the excipient include lactose, dextrose, sucrose, mannitol, sorbitol, cellulose, glycine, silica, talc, stearic acid, sterin, magnesium stearate, magnesium aluminium sillicate, starch, gelatin, tragacanth gum, alginic acid, sodium alginate, methylcellulose, sodium carboxylmethylcellulose, agar, water, ethanol, polyethylene glycol, polyvinylpyrrolidone, sodium chloride, potassium chloride, orange essence, strawberry essence, vanilla favor, and a mixture thereof.

Representative examples of the carrier employed in the pharmaceutical composition of the present invention include distilled water, a saline solution, a glucose solution, a glucose-like solution, alcohol, glycol ether (e.g., polyethylene glycol 400), oil, fatty acid, fatty acid ester, glyceride, a surfactant, a suspension agent, an emulsifier, and a mixture thereof.

A proposed daily dose of the inventive pharmaceutical composition for administration to a mammal including a human may be in the range of 0.01 and 200 mg/kg (a body weight), preferably of 30 and 100 mg/kg (a body weight) per day. The inventive pharmaceutical composition may be administered in a single dose or in divided doses per day. It is understood that the daily dose should be determined in light of various relevant factors including the condition, age, body weight and sex of the subject to be treated, administration route, and disease severity; and, therefore, the dosage suggested above should not be construed to limit the scope of the present invention in anyway.

The present invention is explained in detail with reference to the Examples described below, which are given for the purpose of illustration only, and are not intended to limit the scope of the invention.

EXAMPLE

Hereinafter, a compound of Preparation Example 1 was prepared by the procedure shown in Reaction Scheme 1 below:

[Reaction Scheme 1]

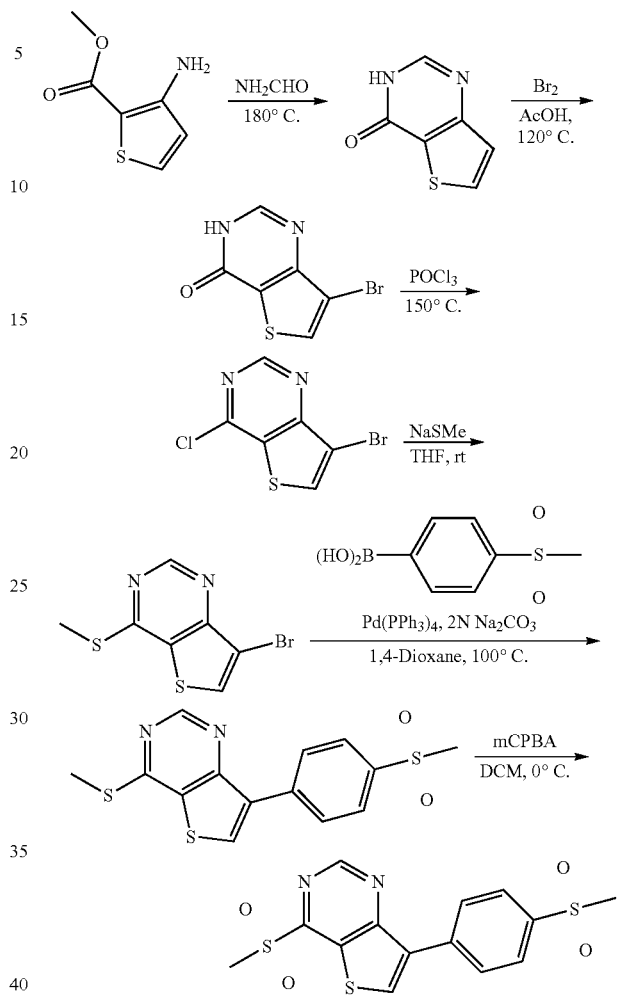

Preparation Example 1

4-methanesulfonyl-7-(4-methanesulfonyl-phenyl)thieno[3,2-d]pyrimidine

Step 1-1) 3H-thieno[3,2-d]pyrimidin-4-one

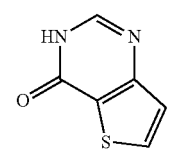

Methyl-3-aminothiophene-2-carboxylate (15 g, 98.6 mmol) (Matrix, Cat #018289, CAS [22288-78-4]) was dissolved in formamide (50 mL) and stirred at 180° C. for 5 hours. The reaction mixture was further stirred at room temperature for 2 hours and the solid thus obtained was filtered to obtain the title compound.

$^1$H NMR (300 MHz, DMSO-d$_6$): δ 12.48 (br, 1H), 8.18 (d, J=5.1 Hz, 1H), 8.14 (s, 1H), 7.40 (d, J=5.1 Hz, 1H).

Step 1-2) 7-bromo-3H-thieno[3,2-d]pyrimidin-4-one

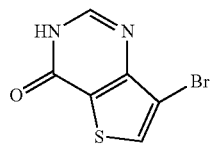 [SMILES: O=c1[nH]cnc2c(Br)csc12]

Thieno[3,2-d]pyrimidin-4(3H)-one (12.5 g) was dissolved in acetic acid (52 mL), and bromine (13 mL) was added thereto. The reaction mixture was stirred at 120° C. for 12 hours in a hermetically sealed reactor. The reaction mixture was cooled to room temperature and distilled under reduced pressure to remove acetic acid. The reaction mixture was placed in ice water, and the solid thus obtained was filtered and washed with ether, and dried to obtain the title compound (7.8 g).
$^1$H NMR (300 MHz, DMSO-d$_6$): δ 12.75 (brs, 1H), 8.36 (s, 1H), 8.24 (s, 1H).

Step 1-3) 7-bromo-4-chlorothieno[3,2-d]pyrimidine

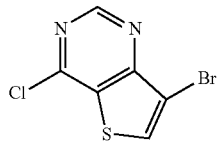 [SMILES: Clc1ncnc2c(Br)csc12]

7-bromothieno[3,2-d]pyrimidin-4(3H)-one (5.9 g) was dissolved in POCl$_3$ (20 mL) and the reaction mixture was stirred at 150° C. for 3 hours. The reaction mixture was cooled to room temperature, and remaining POCl$_3$ was concentrated and placed in ice water. The solid thus obtained was washed with sodium bicarbonate and dried using nitrogen gas. The resulting compound was further dried over anhydrous sodium sulfate, and filtered and distilled under reduced pressure to obtain the title compound (1.0 g, 39%).
$^1$H NMR (300 MHz, DMSO-d$_6$): δ 9.16 (s, 1H), 8.79 (s, 1H).

Step 1-4) 7-bromo-4-methylsulfanylthieno[3,2-d]pyrimidine

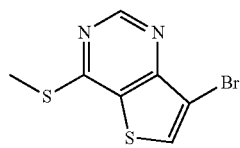

7-bromo-4-chlorothieno[3,2-d]pyrimidine (1 g, 4.0 mmol) was added to tetrahydrofuran (30 mL), and NaSMe (638 mg, 4.8 mmol) was added thereto at room temperature while stirring. After 12 hours, the reaction mixture was cooled to below 10° C. and stirred for 1 hour. The solid thus obtained was washed with water. The resulting compound as a white solid was air-dried at 45° C. for 12 hours to obtain the title compound (800 mg).

$^1$H NMR (300 MHz, DMSO-d$_6$): δ 9.08 (s, 1H), 8.57 (s, 1H), 2.77 (s, 3H).

Step 1-5) 7-(4-methanesulfonyl-phenyl)-4-methylsulfanylthieno[3,2-d]pyrimidine

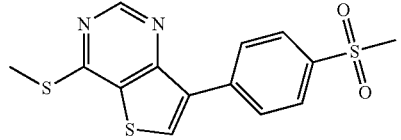

7-bromo-4-methylsulfanylthieno[3,2-d]pyrimidine (270 mg, 1.0 mmol) was added to 1,4-dioxane (10 mL), and 4-methanesulfonyl-phenylboronic acid (310 mg, 1.6 mmol), tetrakis(triphenylphosphine)palladium(0) (71 mg, 0.062 mmol), and 2N aqueous sodium carbonate (3.1 mL, 3.1 mmol) were sequentially added thereto. The air present in the reaction mixture was removed using a nitrogen balloon, and the reaction mixture was heated to 100° C. and stirred for 4 hours. The reaction was terminated by addition of sodium bicarbonate, and the reaction mixture was extracted twice with ethyl acetate. The collected organic layer was dried over anhydrous magnesium sulfate and concentrated under reduced pressure to obtain a foamy residue. The residue was crystallized in the presence of diethyl ether to obtain the title compound (260 mg) as a yellowish solid.
$^1$H NMR (300 MHz, DMSO-d$_6$): δ 9.13 (s, 1H), 8.85 (s, 1H), 8.38 (d, 2H), 8.06 (d, 2H), 3.27 (s, 3H), 2.73 (s, 3H).

Step 1-6) 4-(methanesulfonyl)-7-(4-methanesulfonyl-phenyl)thieno[3,2-d]pyrimidine

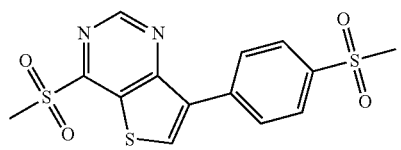

7-(4-methanesulfonyl-phenyl)-4-methylsulfanyl-thieno[3,2-d]pyrimidine (160 mg) was added to dichloromethane (5 mL) and cooled to an internal temperature of 0° C. Then, 3-chlorobenzenecarboperoxalic acid (100 mg) was slowly added thereto and stirred for 1 hour. The reaction mixture was heated to room temperature and neutralized with sodium bicarbonate. The organic layer was separated and the aqueous layer was extracted again with dichloromethane. The organic layer was collected, dried over anhydrous magnesium sulfate, and concentrated under reduced pressure to obtain a foamy residue. The residue was crystallized in the presence of diethyl ether to obtain the title compound (160 mg) as a yellowish solid.
$^1$H NMR (300 MHz, DMSO-d$_6$): δ 9.40 (s, 1H), 9.09 (s, 1H), 8.36 (d, 2H), 8.10 (d, 2H), 3.26 (s, 3H), 3.07 (s, 3H).

Hereinafter, a compound of Preparation Example 2 was prepared by the procedure shown in Reaction Scheme 2 below:

Reaction Scheme 2

Preparation Example 2

2-(2-fluoro-4-methanesulfonyl-phenyl)-4,4,5,5-tetramethyl-1,3,2-dioxaborolane

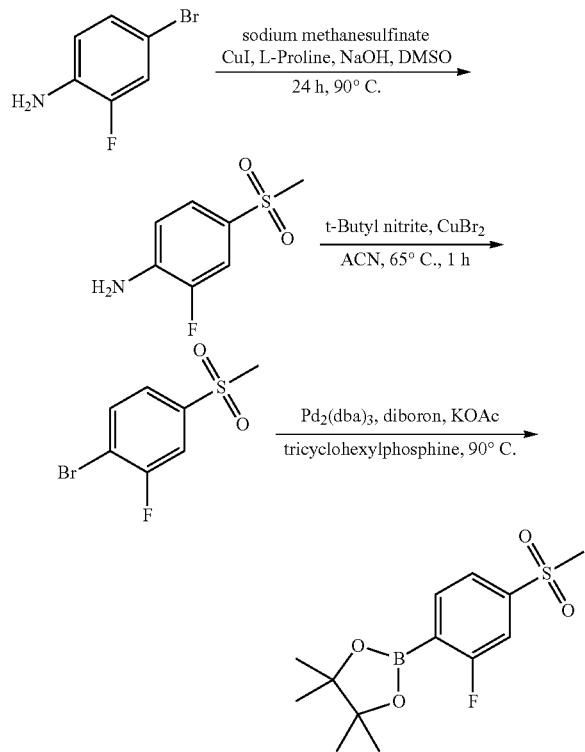

Step 2-1) 2-fluoro-4-(methanesulfonyl)benzenamine 4-bromo-2-fluoroaniline (10.0 g, 52.62 mmol, 1.0 eq), sodium methansulfinate (9.5 g, 1.5 eq), copper(I) iodide (1.0 g, 0.1 eq), L-Proline (1.2 g, 0.2 eq) and sodium hydroxide (0.4 g, 0.2 eq) were placed in a sealed tube, and dimethylsulfoxide (100 mL) was added thereto. The reaction mixture was stirred at 90° C. for 24 hours. After completion of the reaction, the reaction mixture was cooled to room temperature and water was added thereto, followed by extraction three times with ethyl acetate. The extract was dried over anhydrous sodium sulfate and concentrated under reduced pressure. The resulting compound was purified using column chromatography (MC:MeOH=50:1) to obtain the title compound (9.9 g).

$^1$H NMR (300 MHz, DMSO-d$_6$): δ 7.42 (m, 2H), 6.85 (t, 1H), 6.18 (s, NH2), 3.09 (s, 3H)

Step 2-2) 1-bromo-2-fluoro-4-(methanesulfonyl)benzene

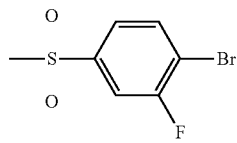

To 2-fluoro-4-(methanesulfonyl)benzenamine 9.9 g (52.62 mmol, 1.0 eq) obtained in Step 2-1, t-butyl nitrite (9.4 mL, 1.5 eq) and copper(II) bromide (17.6 g, 1.5 eq) were added, and acetonitrile (200 mL) was further added thereto. The reaction mixture was stirred at 65° C. for 1 hour and cooled to room temperature, and the reaction was terminated by addition of 1N HCl. Then, the reaction mixture was mixed with water, extracted three times with ethyl acetate, and dried over anhydrous sodium sulfate, followed by concentration under reduced pressure. The resulting compound was purified using column chromatography (dichloromethane) to obtain the title compound (10 g).

$^1$H NMR (300 MHz, DMSO-d$_6$): δ 8.05 (t, 1H), 7.96 (m, 1H), 7.70 (m, 1H), 3.28 (s, 3H)

Step 2-3) 2-(2-fluoro-4-methanesulfonyl-phenyl)-4,4,5,5-tetramethyl-1,3,2-dioxaborolane

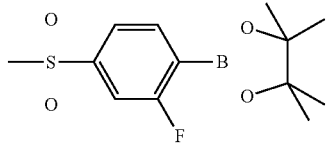

To 1-bromo-2-fluoro-4-(methanesulfonyl)benzene (10.0 g, 39.51 mmol) obtained in Step 2-2, tricyclohexyl phosphine (1.1 g, 0.1 eq), Diboron (20.0 g, 2 eq), Pd$_2$(dba)$_3$ (1.8 g, 0.05 eq) and KOAc (7.7 g, 2 eq) were added, and 1,4-dioxane (100 mL) was further added thereto. The reaction mixture was stirred at 90° C. for 4 hours. After completion of the reaction, the mixture was cooled to room temperature. Then, the reaction mixture was mixed with water, extracted three times with ethyl acetate, and dried over anhydrous sodium sulfate, followed by concentration under reduced pressure. The resulting compound was purified using column chromatography (MC:MeOH=50: 1) to obtain the title compound (10 g).

$^1$H NMR (300 MHz, DMSO-d$_6$): δ 7.90 (m, 1H), 7.73 (m, 2H), 3.28 (s, 3H), 1.31 (s, 12H)

Hereinafter, a compound of Preparation Example 3 was prepared by the procedure shown in Reaction Scheme 3 below.

[Reaction Scheme 3]

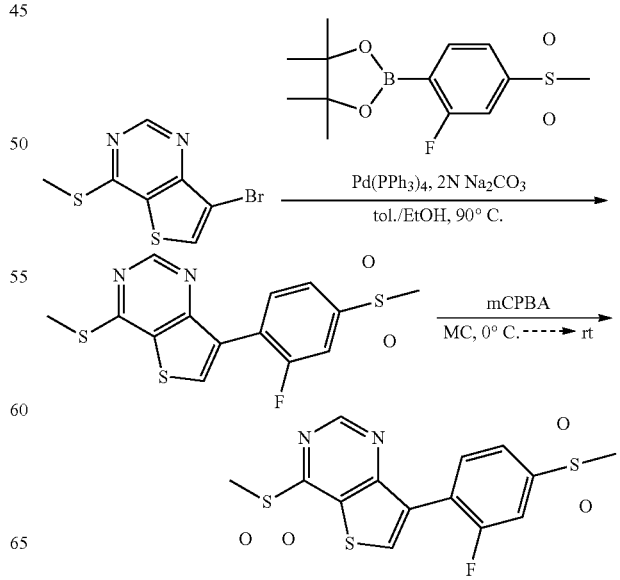

Preparation Example 3

7-(2-fluoro-4-methanesulfonyl-phenyl)-4-(methanesulfonyl)thieno[3,2-d]pyrimidine

Step 3-1) 7-(2-fluoro-4-methanesulfonyl-phenyl)-4-(methylthio)thieno[3,2-d]pyrimidine

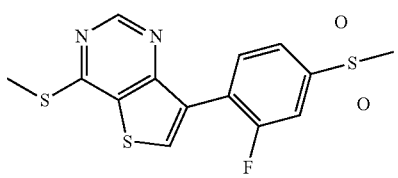

7-bromo-4-methylsulfanylthieno[3,2-d]pyrimidine (270 mg, 1.03 mmol) was added to 1,4-dioxane (10 mL), and 2-(2-fluoro-4-methanesulfonyl-phenyl)-4,4,5,5-tetramethyl-1,3,2-dioxaborolane (1.5 eq), tetrakis(triphenylphosphine)palladium(0) (71 mg, 0.06 eq), 2N aqueous sodium carbonate (3.1 mL, 3 eq) were sequentially added thereto while stirring. The reaction mixture was degassed with Ar(g), heated to 100° C., and stirred at 100° C. for 4 hours. After completion of the reaction using sodium bicarbonate, the reaction mixture was extracted twice with ethyl acetate. The collected organic layer was dried over anhydrous magnesium sulfate, dried, and concentrated under reduced pressure to obtain a foamy residue. The residue was crystallized in the presence of diethyl ether to obtain the title compound as a yellowish solid.

$^1$H NMR (300 MHz, DMSO-$d_6$): δ 9.08 (s, 1H), 8.57 (s, 1H), 2.77 (s, 3H).

Step 3-2) 7-(2-fluoro-4-methanesulfonyl-phenyl)-4-methanesulfonyl-thieno[3,2-d]pyrimidine

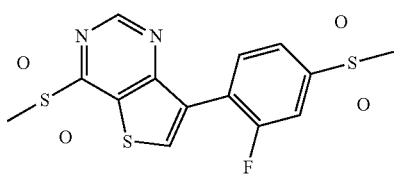

7-(2-fluoro-4-methanesulfonyl-phenyl)-4-methylsulfanyl-thieno[3,2-d]pyrimidine (160 mg) was added to dichloromethane (5 mL), and cooled to an internal temperature of 0° C. Then, 3-chloroperbenzoic acid (100 mg) was slowly added thereto and stirred for 1 hour. The reaction mixture was heated to room temperature and neutralized with sodium bicarbonate. The organic layer was separated and the aqueous layer was extracted again with dichloromethane. The organic layer was collected, dried over anhydrous magnesium sulfate, and concentrated under reduced pressure to obtain a foamy residue. The residue was crystallized in the presence of diethyl ether to obtain the title compound as a yellowish solid (160 mg).

$^1$H NMR (300 MHz, DMSO-$d_6$): δ 9.08 (s, 1H), 8.57 (s, 1H), 2.77 (s, 3H).

Hereinafter, a compound of Preparation Example 4 was prepared by the procedure shown in Reaction Scheme 4 below.

[Reaction Scheme 4]

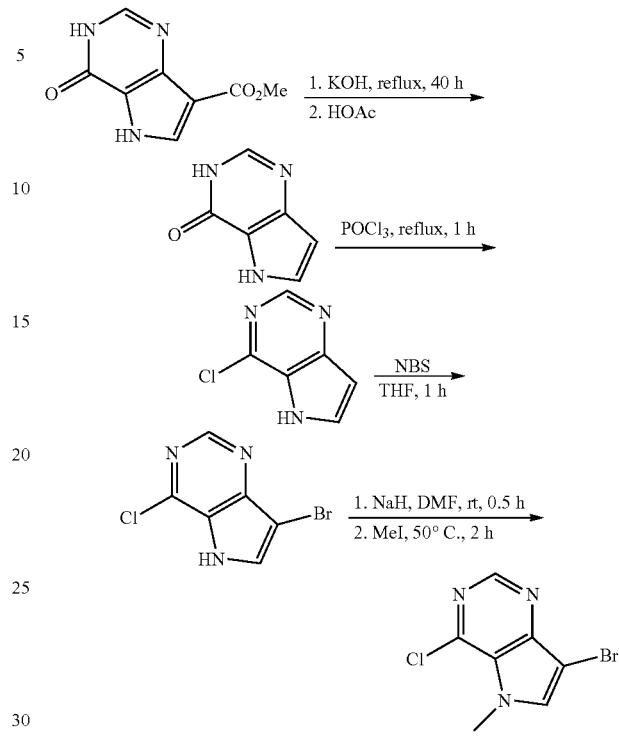

Preparation Example 4

7-bromo-4-chloro-5-methyl-5H-pyrrolo[3,2-d]pyrimidine

Step 4-1) 3,5-dihydropyrrolo[3,2-d]pyrimidin-4-one

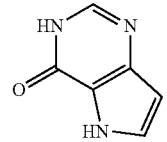

To methyl 4-oxo-4,5-dihydro-3H-pyrrolo[3,2-d]pyrimidine-7-carboxylate synthesized by the known method (Organic Process Research & Development 2009, 13, 928-932), 10% potassium hydroxide (240 mL) was added, and refluxed for 40 hours while stirring. After completion of the reaction, the reaction mixture was cooled to room temperature and neutralized with acetic acid to a pH of 6.5-7.5. The solid thus obtained was filtered and dried to obtain the title compound.

$^1$H NMR (300 MHz, DMSO-$d_6$): δ 12.05 (bs, 1H), 11.82 (bs, 1H), 7.77 (s, 1H), 7.36 (s, 1H), 6.35 (s, 1H).

Step 4-2) 4-chloro-5H-pyrrolo[3,2-d]pyrimidine

To 3,5-dihydropyrrolo[3,2-d]pyrimidin-4-one (1.8 g), POCl₃ (5 mL) was added, and refluxed while stirring. After completion of the reaction, the reaction mixture was distilled under reduced pressure to remove POCl₃. Then, the reaction mixture was mixed with ethyl acetate, washed with saturated sodium bicarbonate and washed with a saline solution. The washed mixture was dried over anhydrous sodium sulfate, and filtered and distilled under reduced pressure to obtain the title compound.

$^1$H NMR (300 MHz, DMSO-$d_6$): δ 12.43 (s, 1H), 8.61 (s, 1H), 7.97 (dd, 1H), 6.72 (dd, 1H), to obtain the title compound as a yellowish solid (160 mg).

Step 4-3)
7-bromo-4-chloro-5H-pyrrolo[3,2-d]pyrimidine

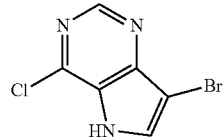 [SMILES: Clc1ncnc2c(Br)c[nH]c12]

To 4-chloro-5H-pyrrolo[3,2-d]pyrimidine (100 mg), tetrahydrofuran (5 mL) was added, and N-bromosuccinimide (116 mg) was further added thereto, followed by stirring for 1 hour. After completion of the reaction, the reaction mixture was mixed with ethyl acetate and washed with water. The washed mixture was dried over anhydrous sodium sulfate, and filtered and distilled under reduced pressure to obtain the title compound.

$^1$H NMR (300 MHz, DMSO-$d_6$): δ 12.95 (s, 1H), 8.71 (s, 1H), 8.24 (d, 1H).

Step 4-4) 7-bromo-4-chloro-5-methyl-5H-pyrrolo[3,2-d]pyrimidine

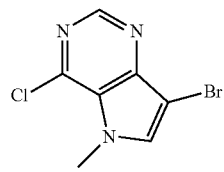

To 7-bromo-4-chloro-5H-pyrrolo[3,2-d]pyrimidine (147 mg), N,N-dimethylformamide (10 mL) was added, and NaH (36 mg) was further added thereto, followed by stirring for 30 min. Subsequently, methyl iodide was added thereto, and the reaction mixture was heated to 50° C. and stirred for 2 hours. After completion of the reaction, the reaction mixture was mixed with ethyl acetate and washed with water. The washed mixture was dried over anhydrous sodium sulfate, and filtered and distilled under reduced pressure to obtain the title compound.

$^1$H NMR (300 MHz, DMSO-$d_6$): δ 8.68 (s, 1H), 8.22 (s, 1H), 4.11 (s, 3H).

Hereinafter, a compound of Preparation Example 5 was prepared by the procedure shown in Reaction Scheme 5 below.

[Reaction Scheme 5]

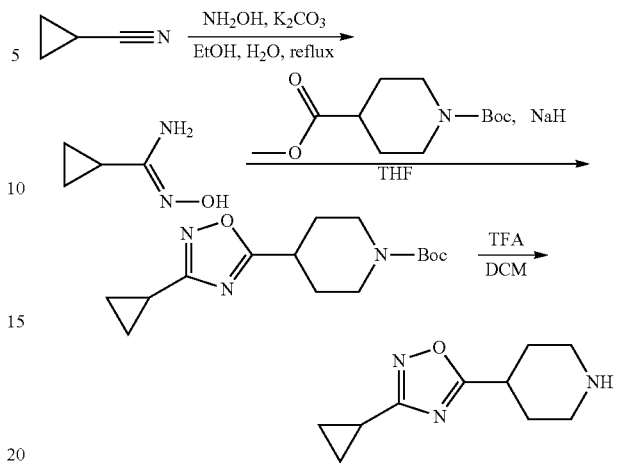

Preparation Example 5

3-cyclopropyl-5-(piperidin-4-yl)-1,2,4-oxadiazole

Step 5-1) N-hydroxycyclopropylamidine

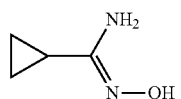

Cyclopropylcyanide (3 g, 44.7 mmol) was added to a solution of ethanol and water (30 mL, respectively), and potassium carbonate (6 g, 44.7 mmol) was further added thereto while stirring. Then, a solution of hydroxyamine hydrochloride (6.2 g, 89.4 mmol) in water was dropwise added thereto and refluxed for 12 hours while stirring. The reaction mixture was distilled under reduced pressure to remove ethanol, and extracted three times with ethyl acetate. The organic layer was dried over anhydrous magnesium sulfate, and filtered and distilled under reduced pressure to obtain the title compound (2.7 g) as colorless and transparent oil.

$^1$H NMR (300 MHz, DMSO-$d_6$): δ 8.68 (s, 1H), 5.18 (s, 2H), 1.33-1.30 (m, 1H), 0.66-0.55 (m, 4H).

Step 5-2) tert-butyl-4-(3-cyclopropyl-[1,2,4]oxadiazol-5-yl)piperidine

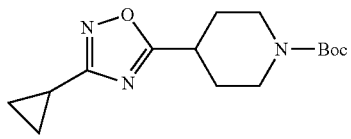 [SMILES: CC(C)(C)OC(=O)N1CCC(c2nc(C3CC3)no2)CC1]

N-hydroxycyclopropylamidine (1 g, 10.1 mmol) was added to tetrahydrofuran (20 mL), and NaH (880 mg, 20.2 mmol) was further added thereto while stirring. The mixture was heated to 50° C., and stirred for 3 hours. Then, a solution of 1-tert-butyl-4-methylpiperidin-1,4-dicarboxylate (1.22 g, 5.04 mmol) in tetrahydrofuran (3 mL) was added thereto at the same temperature and refluxed for 3 hours. The reaction mixture was cooled to room temperature, neutralized with 1N aqueous hydrochloric acid, and extracted with ethyl acetate. The organic layer was dried over anhydrous magnesium sulfate, and concentrated under reduced pressure to obtain an oily residue. The residue was purified using column chromatography to obtain the title compound (1.1 g) as colorless and transparent oil.

$^1$H NMR (300 MHz, DMSO-d$_6$): δ 3.91-3.87 (m, 2H), 3.22-3.18 (m, 1H), 2.50 (m, 2H), 2.00 (m, 1H), 1.99 (m, 2H), 1.56-1.51 (m, 2H), 1.40 (s, 9H), 1.05-1.01 (m, 2H), 0.89-0.84 (m, 2H).

Step 5-3) 3-cyclopropyl-5-(piperidin-4-yl)-1,2,4-oxadiazole

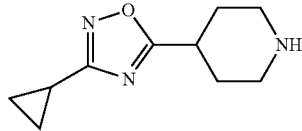 [SMILES: C1CC(c2nc(C3CC3)no2)CCN1]

Tert-butyl-4-(3-cyclopropyl-[1,2,4]oxadiazol-5-yl)piperidine-1-carboxylate (1.1 g, 3.8 mmol) was dissolved in dichloromethane (10 mL), and trifluoroacetic acid (4 mL) was further added thereto. The reaction mixture was stirred at room temperature for 1 hour, neutralized with sodium bicarbonate, and extracted with dichloromethane two times. The organic layer was dried over anhydrous magnesium sulfate, and concentrated under reduced pressure to obtain the title compound (600 mg) as yellowish and transparent oil.

$^1$HNMR (300 MHz, DMSO-d$_6$): δ 3.08-2.98 (m, 3H), 2.63 (m, 2H), 2.12-2.09 (m, 1H), 2.02-1.98 (m, 2H), 1.63 (m, 2H), 1.09-1.03 (m, 2H), 0.91-0.87 (m, 2H).

Preparation of Intermediate 1

4-(3-ethyl-[1,2,4]oxadiazol-5-yl)piperidine

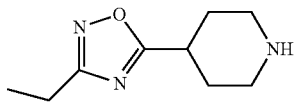

The procedure of Preparation Example 5 was repeated except for using propionitrile instead of cyclopropylcyanide in step 5-1) to obtain the title compound.

$^1$H NMR (300 MHz, DMSO-d$_6$): δ 3.94-3.89 (d, 1H), 3.22-3.07 (m, 3H), 2.79-2.64 (m, 4H), 2.01-1.98 (m, 2H), 1.74-1.67 (m, 2H), 1.22 (t, 3H).

Preparation of Intermediate 2

4-(3-isopropyl-[1,2,4]oxadiazol-5-yl)piperidine

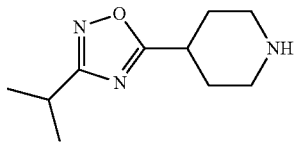

The procedure of Preparation Example 5 was repeated except for using isobutyronitrile instead of cyclopropylcyanide in step 5-1) to obtain the title compound.

$^1$H NMR (300 MHz, DMSO-d$_6$): δ 4.00-3.99 (m, 1H), 3.92-3.86 (d, 2H), 3.24-3.05 (m, 3H), 2.79-2.64 (m, 2H), 2.01-1.98 (m, 2H), 1.74-1.67 (m, 2H), 1.05-1.00 (d, 6H).

Preparation of Intermediate 3

4-(3-cyclopentyl-[1,2,4]oxadiazol-5-yl)piperidine

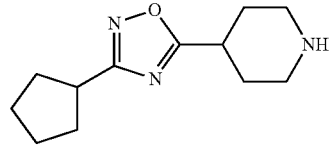 [SMILES: C1CCC(c2noc(C3CCNCC3)n2)C1]

The procedure of Preparation Example 5 was repeated except for using cyclopentanecarbonitrile instead of cyclopropylcyanide in step 5-1) to obtain the title compound.

$^1$H NMR (300 MHz, DMSO-d$_6$): δ 8.51 (s, 1H), 3.38-3.35 (m, 2H), 3.15 (m, 1H), 3.04-2.99 (m, 2H), 2.18-2.13 (m, 2H), 1.96-1.82 (m, 4H), 1.70-1.61 (m, 6H).

Preparation of Intermediate 4

4-(3-cyclohexyl-[1,2,4]oxadiazol-5-yl)piperidine

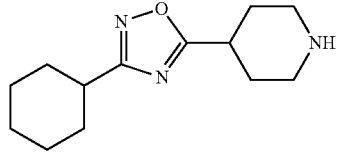 [SMILES: C1CCC(c2noc(C3CCNCC3)n2)CC1]

The procedure of Preparation Example 5 was repeated except for using cyclohexanecarbonitrile instead of cyclopropylcyanide in step 5-1) to obtain the title compound.

$^1$H NMR (300 MHz, DMSO-d$_6$): δ 3.31 (m, 3H), 3.00 (m, 2H), 2.77 (m, 1H), 2.15 (m, 2H), 1.91 (m, 4H), 1.71 (m, 4H), 1.41 (m, 6H).

Preparation of Intermediate 5

4-(3-phenyl-[1,2,4]oxadiazol-5-yl)piperidine

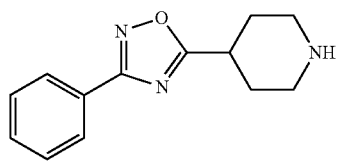 [SMILES: c1ccc(-c2noc(C3CCNCC3)n2)cc1]

The procedure of Preparation Example 5 was repeated except for using phenylcarbonitrile instead of cyclopropylcyanide in step 5-1) to obtain the title compound.

$^1$H NMR (300 MHz, DMSO-d$_6$): δ 8.36 (m, 2H), 7.61 (m, 3H), 3.46 (m, 1H), 3.39 (m, 2H), 3.03 (m, 2H), 2.25 (m, 2H), 1.91 (m, 2H).

Hereinafter, a compound of Example 1 was prepared by the procedure shown in Reaction Scheme 6 below.

[Reaction Scheme 6]

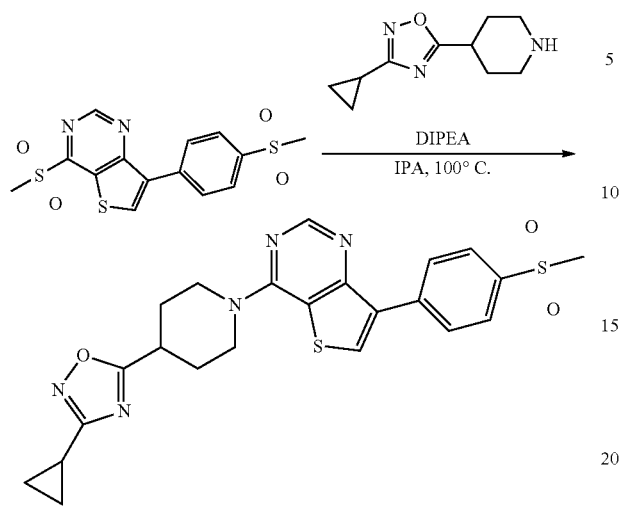

Example 1

3-cyclopropyl-5-(1-(7-(4-methanesulfonyl-phenyl)thieno[3,2-d]pyrimidin-4-yl)piperidin-4-yl)-1,2,4-oxadiazole To isopropyl alcohol (2 mL), 4-methanesulfonyl-7-(4-methanesulfonyl-phenyl)thieno[3,2-d]pyrimidine (50 mg, 0.14 mmol) obtained in Preparation Example 1, 4-(3-cyclopropyl-[1,2,4]oxadiazol-5-yl)piperidine (40 mg, 0.203 mmol) obtained in Preparation Example 5 and diisopropyl ethylamine (47 µL, 0.270 mmol) were added, and stirred at 100° C. for 12 hours. The reaction mixture was concentrated under reduced pressure, and the resulting residue was dissolved in dichloromethane (1 mL), followed by a thin layer chromatography to obtain the title compound (25 mg) as a white solid.

$^1$H NMR (300 MHz, DMSO-$d_6$): δ 8.66 (s, 1H), 8.63 (s, 1H), 8.30 (d, 2H), 8.03 (d, 2H), 4.78-4.65 (m, 2H), 3.26 (s, 3H), 2.27-2.18 (m, 2H), 2.11-2.08 (m, 1H), 1.82-1.78 (m, 2H), 1.06-1.02 (m, 2H), 0.88 (m, 2H).

Example 2

7-(4-methanesulfonyl-phenyl)-4-(pyrrolidin-1-yl)thieno[3,2-d]pyrimidine

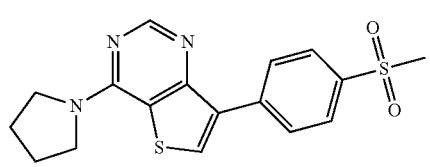 [SMILES: CS(=O)(=O)c1ccc(-c2csc3c(N4CCCC4)ncnc23)cc1]

The procedure of Example 1 was repeated except for using pyrrolidine instead of 4-(3-cyclopropyl-[1,2,4]oxadiazol-5-yl)piperidine to obtain the title compound.

$^1$H NMR (300 MHz, DMSO-$d_6$): δ 8.65 (s, 1H), 8.42 (s, 1H), 8.35 (d, 2H), 8.01 (d, 2H), 3.86 (m, 4H), 3.24 (s, 3H), 2.01 (m, 4H).

Example 3

7-(4-methanesulfonyl-phenyl)-4-(piperidin-1-yl)thieno[3,2-d]pyrimidine

The procedure of Example 1 was repeated except for using piperidine instead of 4-(3-cyclopropyl-[1,2,4]oxadiazol-5-yl)piperidine to obtain the title compound.

$^1$H NMR (300 MHz, DMSO-$d_6$): δ 8.72 (s, 1H), 8.57 (s, 1H), 8.32 (d, 2H), 8.02 (d, 2H), 3.96 (m, 4H), 3.21 (s, 3H), 1.66-1.70 (m, 6H).

Example 4

3-ethyl-5-(1-(7-(4-methanesulfonyl-phenyl)thieno[3,2-d]pyrimidin-4-yl)piperidin-4-yl)-1,2,4-oxadiazole

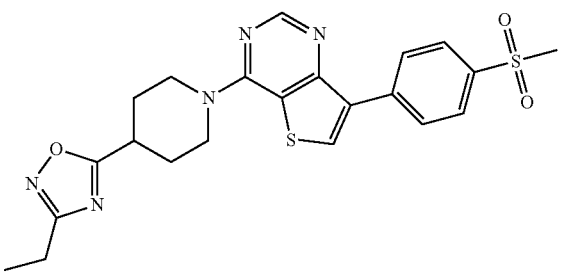 [SMILES: CCc1noc(C2CCN(c3ncnc4c(-c5ccc(S(C)(=O)=O)cc5)csc34)CC2)n1]

The procedure of Example 1 was repeated except for using 4-(3-ethyl-[1,2,4]oxadiazol-5-yl)piperidine instead of 4-(3-cyclopropyl-[1,2,4]oxadiazol-5-yl)piperidine to obtain the title compound.

$^1$H NMR (300 MHz, DMSO-$d_6$): δ 8.65 (s, 1H), 8.58 (s, 1H), 8.32 (d, 2H), 8.01 (d, 2H), 4.71-4.68 (m, 2H), 3.58 (m, 2H), 3.24 (s, 3H), 2.89 (q, 2H), 2.03-2.00 (m, 2H), 1.74 (m, 1H), 1.67-1.54 (m, 2H), 1.04 (t, 3H).

Example 5

3-isopropyl-5-(1-(7-(4-methanesulfonyl-phenyl)thieno[3,2-d]pyrimidin-4-yl)piperidin-4-yl)-1,2,4-oxadiazole

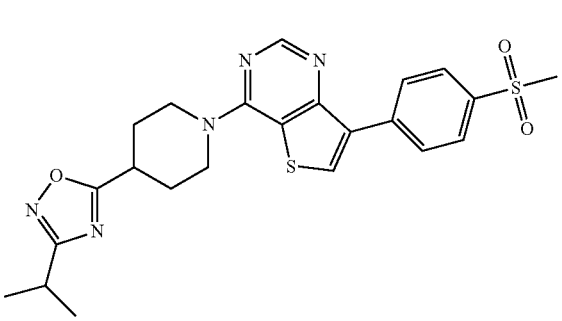 [SMILES: CC(C)c1noc(C2CCN(c3ncnc4c(-c5ccc(S(C)(=O)=O)cc5)csc34)CC2)n1]

The procedure of Example 1 was repeated except for using 4-(3-isopropyl-[1,2,4]oxadiazol-5-yl)piperidine instead of 4-(3-cyclopropyl-[1,2,4]oxadiazol-5-yl)piperidine to obtain the title compound.

$^1$H NMR (300 MHz, DMSO-$d_6$): δ 8.64 (s, 1H), 8.61 (s, 1H), 8.31 (d, 2H), 8.01 (d, 2H), 4.70-4.65 (m, 2H), 3.55-3.51 (m, 2H), 3.24 (s, 3H), 3.06-2.99 (m, 1H), 223-2.19 (m, 2H), 1.87-1.80 (m, 2H), 1.23 (d, 6H).

Example 6

3-cyclopentyl-5-(1-(7-(4-methanesulfonyl-phenyl) thieno[3,2-d]pyrimidin-4-yl)piperidin-4-yl)-1,2,4-oxadiazole

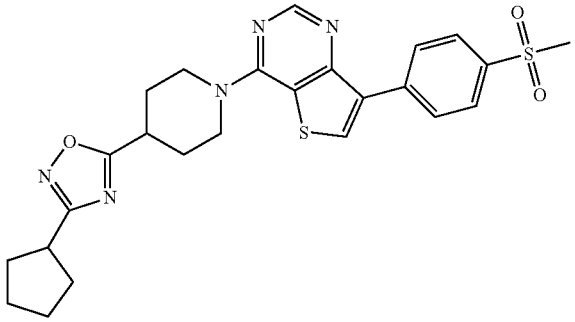 [SMILES: CS(=O)(=O)c1ccc(-c2csc3c(N4CCC(c5nc(C6CCCC6)no5)CC4)ncnc23)cc1]

The procedure of Example 1 was repeated except for using 4-(3-cyclopentyl-[1,2,4]oxadiazol-5-yl)piperidine instead of 4-(3-cyclopropyl-[1,2,4]oxadiazol-5-yl)piperidine to obtain the title compound.

$^1$H NMR (300 MHz, DMSO-$d_6$): δ 8.66 (s, 1H), 8.60 (s, 1H), 8.29 (d, 2H), 8.00 (d, 2H), 4.68-4.64 (m, 2H), 3.53-3.46 (m, 3H), 3.23 (s, 3H), 3.14 (m, 1H), 2.21-2.18 (m, 2H), 1.96-1.94 (m, 2H), 1.85-1.78 (m, 2H), 1.68-1.60 (m, 6H).

Example 7

3-cyclohexyl-5-(1-(7-(4-methanesulfonyl-phenyl) thieno[3,2-d]pyrimidin-4-yl)piperidin-4-yl)-1,2,4-oxadiazole

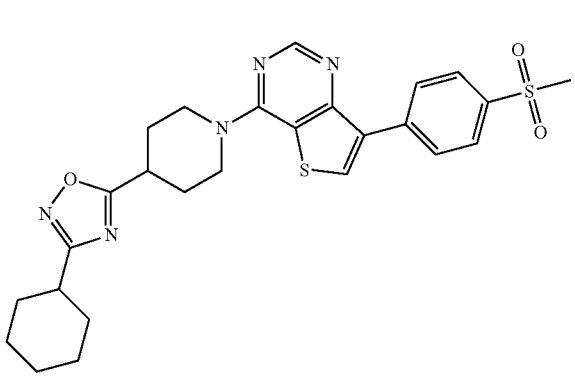 [SMILES: CS(=O)(=O)c1ccc(-c2csc3c(N4CCC(c5nc(C6CCCCC6)no5)CC4)ncnc23)cc1]

The procedure of Example 1 was repeated except for using 4-(3-cyclohexyl-[1,2,4]oxadiazol-5-yl)piperidine instead of 4-(3-cyclopropyl-[1,2,4]oxadiazol-5-yl)piperidine to obtain the title compound.

$^1$H NMR (300 MHz, DMSO-$d_6$): δ 8.69 (s, 1H), 8.63 (s, 1H), 8.33 (d, 2H), 8.03 (d, 2H), 4.68 (m, 2H), 3.53 (m, 3H), 3.26 (s, 3H), 2.75 (m, 1H), 2.22 (m, 2H), 1.77 (m, 7H), 1.37 (m, 5H).

Example 8

5-(1-(7-(4-(methanesulfonylphenyl)phenyl)thieno[3,2-d]pyrimidin-4-yl)piperidin-4-yl)-3-phenyl-1,2,4-oxadiazole

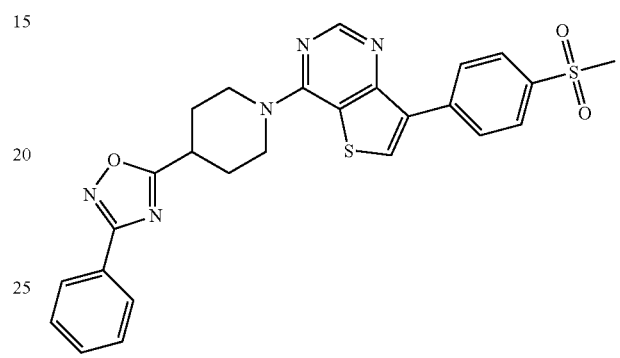

The procedure of Example 1 was repeated except for using 4-(3-phenyl-[1,2,4]oxadiazol-5-yl)piperidine instead of 4-(3-cyclopropyl-[1,2,4]oxadiazol-5-yl)piperidine to obtain the title compound.

$^1$H NMR (300 MHz, DMSO-$d_6$): δ 8.70 (s, 1H), 8.65 (s, 1H), 8.34 (d, 2H), 8.01 (m, 4H), 7.58 (m, 3H), 4.74 (m, 2H), 3.59 (m, 3H), 3.26 (s, 3H), 2.32 (m, 2H), 1.96 (m, 2H).

Example 9

3-isopropyl-5-(4-(7-(4-methanesulfonyl-phenyl) thieno[3,2-d]pyrimidin-4-yl)piperazin-1-yl)-1,2,4-oxadiazole

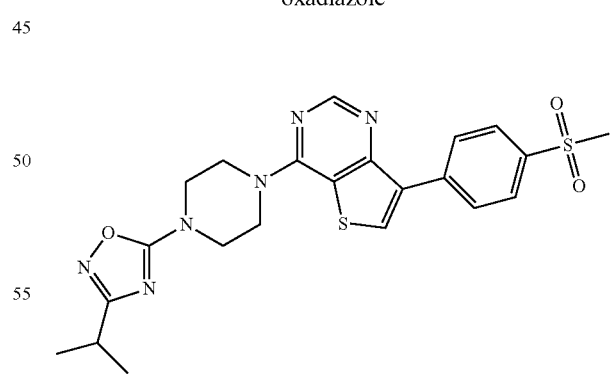

The procedure of Example 1 was repeated except for using 1-(3-isopropyl-[1,2,4]oxadiazol-5-yl)piperazine instead of 4-(3-cyclopropyl-[1,2,4]oxadiazol-5-yl)piperidine to obtain the title compound.

$^1$H NMR (300 MHz, DMSO-$d_6$): δ 8.73 (s, 1H), 8.66 (s, 1H), 8.32 (d, 2H), 8.03 (d, 2H), 4.16-4.15 (m, 4H), 3.77-3.76 (m, 4H), 3.26 (s, 3H), 2.88-2.83 (m, 1H), 2.21 (d, 6H).

Example 10 tert-butyl 4-(7-(4-methanesulfonyl-phenyl)thieno[3,2-d]pyrimidin-4-yl)piperazine-1-carboxylate

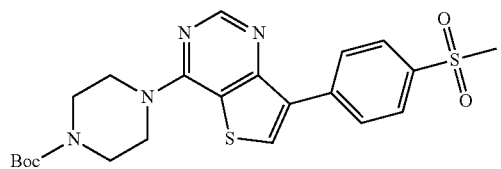 [SMILES: CC(C)(C)OC(=O)N1CCN(c2ncnc3c(-c4ccc(S(C)(=O)=O)cc4)csc23)CC1]

The procedure of Example 1 was repeated except for using piperazine-1-carboxylic acid-tert-butyl ester instead of 4-(3-cyclopropyl-[1,2,4]oxadiazol-5-yl)piperidine to obtain the title compound.

$^1$H NMR (300 MHz, DMSO-$d_6$): δ 8.69 (s, 1H), 8.62 (s, 1H), 8.32 (d, 2H), 8.02 (d, 2H), 4.03-3.97 (m, 4H), 3.59-3.49 (m, 4H), 3.32 (s, 3H), 1.43 (s, 9H).

Example 11

4-(4-(5-ethylpyrimidin-2-yl)piperazin-1-yl)-7-(4-methanesulfonyl-phenyl)thieno[3,2-d]pyrimidine

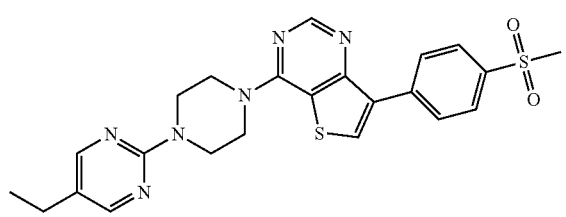 [SMILES: CCc1cnc(N2CCN(c3ncnc4c(-c5ccc(S(C)(=O)=O)cc5)csc34)CC2)nc1]

The compound obtained in Example 10 was deprotected as in Step 5-3), and subjected to a reaction with 2-chloro-5-ethylpyrimidine under conditions similar to Example 1 to obtain the title compound.

$^1$H NMR (300 MHz, DMSO-$d_6$): δ 8.68 (s, 1H), 8.64 (s, 1H), 8.34 (d, 2H), 8.31 (s, 2H), 8.03 (d, 2H), 4.10 (m, 4H), 3.92 (m, 4H), 3.26 (s, 3H), 2.45 (m, 2H), 1.25 (m, 3H).

Hereinafter, a compound of Example 12 was prepared by the procedure shown in Reaction Scheme 7 below.

[Reaction Scheme 7]

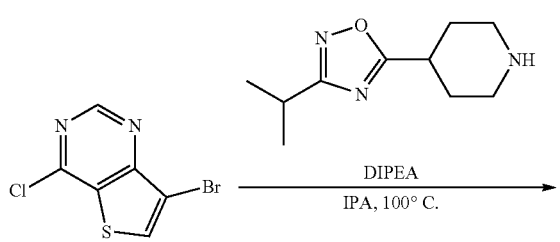

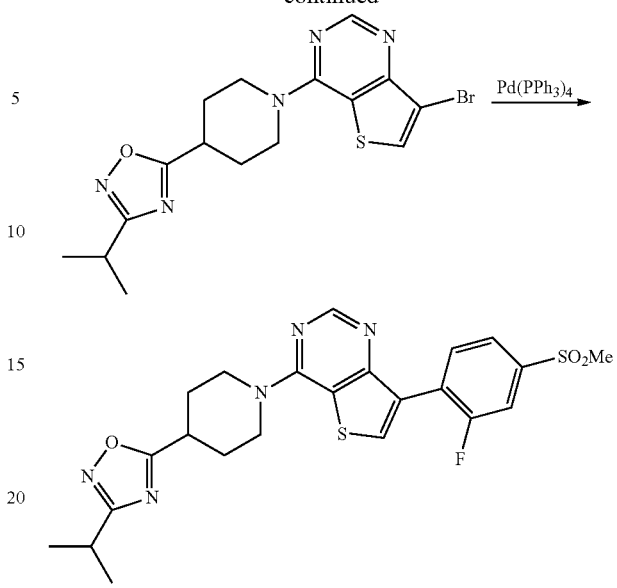

Example 12

7-(2-fluoro-4-methanesulfonyl-phenyl)-4-[4-(3-isopropyl-[1,2,4]oxadiazol-5-yl)-piperidin-4-yl]-thieno[3,2-d]pyrimidine Step 12-1) 7-bromo-4-[4-(3-isopropyl-[1,2,4]oxadiazol-5-yl)-piperidin-1-yl]-thieno[3,2-d]pyrimidine

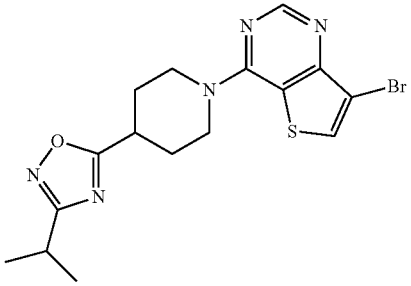 [SMILES: CC(C)c1noc(C2CCN(c3ncnc4c(Br)csc34)CC2)n1]

7-bromo-4-chlorothieno[3,2-d]pyrimidine (100 mg) was added to isopropyl alcohol (3 mL), and 4-(3-isopropyl-[1,2,4]-oxadiazol-5-yl)piperidine (100 mg) and diisopropylethylamine (200 µL) were further added thereto. The reaction mixture was stirred at 100° C. for 12 hours. Then, the reaction mixture was mixed with saturated ammonium hydroxide solution and extracted twice with ethyl acetate. The organic layer was washed with water, dried over anhydrous magnesium sulfate, and concentrated under reduced pressure to obtain a foamy residue. The residue was crystallized in the presence of diethyl ether to obtain the title compound (100 mg) as a whitish solid.

$^1$H NMR (300 MHz, DMSO-$d_6$): δ 8.57 (s, 1H), 8.44 (s, 1H), 4.63-4.59 (m, 2H), 3.48 (m, 3H), 3.00 (m, 1H), 2.21-2.16 (m, 2H), 1.80-1.76 (m, 2H), 1.21 (d, 6H).

Step 12-2) 7-(2-fluoro-4-methanesulfonyl-phenyl)-4-[4-(3-isopropyl-[1,2,4]oxadiazol-5-yl)-piperidin-4-yl]-thieno[3,2-d]pyrimidine

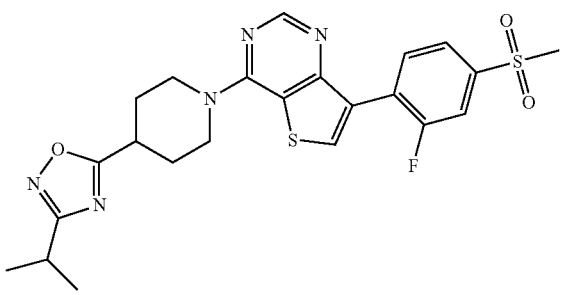 [SMILES: CC(C)c1noc(C2CCN(c3ncnc4c(-c5ccc(S(C)(=O)=O)cc5F)csc34)CC2)n1]

7-bromo-4-[4-(3-isopropyl-[1,2,4]oxadiazol-5-yl)-piperidin-1-yl]-thieno[3,2-d]pyrimidine (50 mg) was dissolved in 1,4-dioxane (1 mL), and 2-(2-fluoro-4-methanesulfonyl-phenyl)-4,4,5,5-tetramethyl-[1,3,2]dioxaborolane (35 mg), triphosphine palladium tetrakis (10 mg) and 2N sodium carbonate solution (1 μL) were sequentially added thereto, followed by degassing with nitrogen gas. The reaction mixture was stirred at 100° C. for 12 hours, cooled to room temperature, and mixed with water. The reaction mixture was extracted with ethyl acetate, dried over anhydrous magnesium sulfate; and concentrated under reduced pressure to obtain a foamy residue. The residue was crystallized in the presence of diethyl ether to obtain the title compound (20 mg) as a whitish solid.

$^1$H NMR (300 MHz, DMSO-d$_6$): δ 8.57 (s, 1H), 8.56 (s, 1H), 8.17 (m, 1H), 7.90 (m, 2H), 4.70 (m, 2H), 3.48 (m, 3H), 3.33 (s, 3H), 3.03 (m, 1H), 2.24 (m, 2H), 1.85 (m, 2H), 1.25 (d, 6H).

Example 13

7-(3-fluoro-4-methanesulfonyl-phenyl)-4-[4-(3-isopropyl-[1,2,4]oxadiazol-5-yl)-piperidin-4-yl]-thieno[3,2-d]pyrimidine

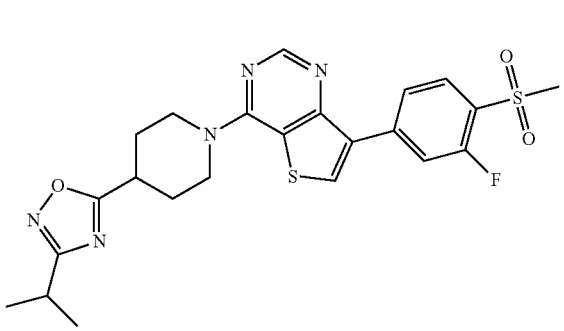 [SMILES: CC(C)c1noc(C2CCN(c3ncnc4c(-c5ccc(S(C)(=O)=O)c(F)c5)csc34)CC2)n1]

The procedure of Example 12 was repeated except for using 2-(3-fluoro-4-methanesulfonyl-phenyl)-4,4,5,5-tetramethyl-[1,3,2]dioxaborolane instead of 2-(2-fluoro-4-methanesulfonyl-phenyl)-4,4,5,5-tetramethyl-[1,3,2]dioxaborolane in Step 12-2 to obtain the title compound.

$^1$H NMR (300 MHz, DMSO-d$_6$): δ 8.57 (s, 1H), 8.56 (s, 1H), 8.32 (m, 1H), 8.00 (m, 2H), 4.70 (m, 2H), 3.48 (m, 3H), 3.33 (s, 3H), 3.03 (m, 1H), 2.24 (m, 2H), 1.85 (m, 2H), 1.26 (d, 6H).

Example 14

4-[4-(3-isopropyl-[1,2,4]oxadiazol-5-yl)-piperidin-1-yl]-7-(4-nitro-phenyl)-thieno[3,2-d]pyrimidine

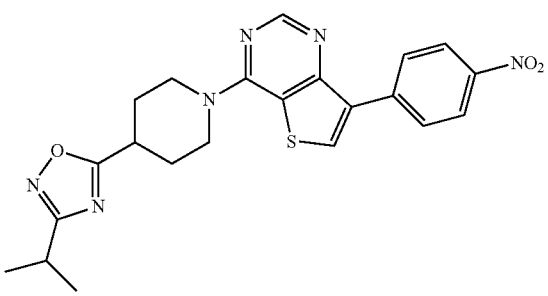 [SMILES: CC(C)c1noc(C2CCN(c3ncnc4c(-c5ccc([N+](=O)[O-])cc5)csc34)CC2)n1]

The procedure of Example 12 was repeated except for using 4-nitrophenylboronic acid instead of 2-(2-fluoro-4-methanesulfonyl-phenyl)-4,4,5,5-tetramethyl-[1,3,2]oxaborolane in Step 12-2 to obtain the title compound.

$^1$H NMR (300 MHz, DMSO-d$_6$): δ 8.78 (s, 1H), 8.65 (s, 1H), 8.42-8.33 (dd, 4H), 4.72-4.61 (m, 2H), 3.56-3.46 (m, 2H), 3.08-2.99 (m, 1H), 2.26-2.21 (m, 2H), 1.89-1.82 (m, 2H), 1.24 (d, 6H).

Example 15

4-{4-[4-(3-isopropyl-[1,2,4]oxadiazol-5-yl)-piperidin-1-yl]-thieno[3,2-d]pyrimidin-7-yl}-benzoic acid

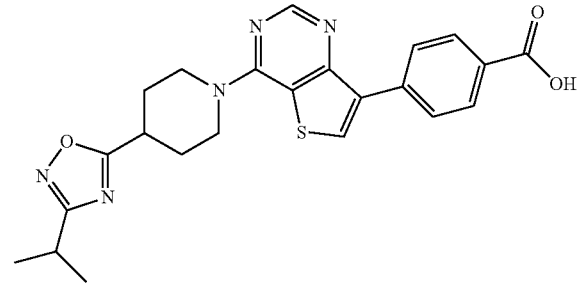 [SMILES: CC(C)c1noc(C2CCN(c3ncnc4c(-c5ccc(C(=O)O)cc5)csc34)CC2)n1]

The procedure of Example 12 was repeated except for using 4-carboxyphenylboronic acid instead of 2-(2-fluoro-4-methanesulfonyl-phenyl)-4,4,5,5-tetramethyl-[1,3,2]dioxaborolane in Step 12-2 to obtain the title compound.

$^1$H NMR (300 MHz, DMSO-d$_6$): δ 8.57 (s, 1H), 8.56 (s, 1H), 8.32 (d, 2H), 7.98 (d, 2H), 4.66 (m, 2H), 3.48 (m, 3H), 3.03 (m, 1H), 2.24 (m, 2H), 1.85 (m, 2H), 1.22 (d, 6H).

Example 16

4-{4-[4-(3-isopropyl-[1,2,4]oxadiazol-5-yl)-piperidin-1-yl]-thieno[3,2-d]pyrimidin-7-yl}-benzoic acid methyl ester

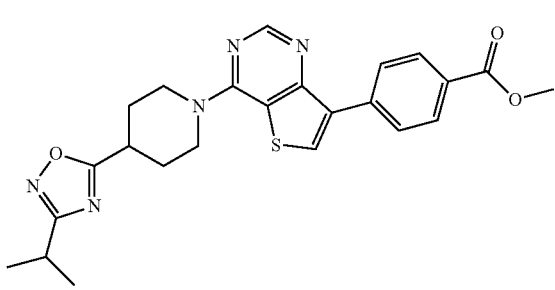 [SMILES: COC(=O)c1ccc(-c2csc3c(N4CCC(c5nc(C(C)C)no5)CC4)ncnc23)cc1]

The procedure of Example 12 was repeated except for using 4-methoxycarbonylphenylboronic acid instead of 2-(2-fluoro-4-methanesulfonyl-phenyl)-4,4,5,5-tetramethyl-[1,3,2]dioxaborolane in Step 12-2 to obtain the title compound.

$^1$H NMR (300 MHz, DMSO-d$_6$): δ 8.57 (s, 1H), 8.56 (s, 1H), 8.32 (d, 2H), 7.98 (d, 2H), 4.66 (m, 2H), 3.66 (s, 3H), 3.48 (m, 3H), 3.03 (m, 1H), 2.24 (m, 2H), 1.85 (m, 2H), 1.22 (d, 6H).

Example 17

4-[4-(3-tert-butyl-[1,2,4]oxadiazol-5-yl)-piperidin-1-yl]-7-(2-fluoro-4-methanesulfonyl-phenyl)-thieno[3,2-d]pyrimidine

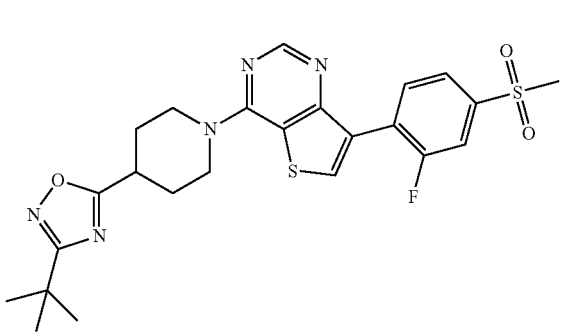 [SMILES: CC(C)(C)c1noc(C2CCN(c3ncnc4c(-c5ccc(S(C)(=O)=O)cc5F)csc34)CC2)n1]

The procedure of Example 12 was repeated except for using 4-(3-tert-butyl-[1,2,4]-oxadiazol-5-yl)piperidine instead of 4-(3-isopropyl-[1,2,4]-oxadiazol-5-yl)piperidine in Step 12-1 to obtain the title compound.

$^1$H NMR (300 MHz, DMSO-d$_6$): δ 8.65 (s, 1H), 8.56 (s, 1H), 8.17 (t, 1H), 7.94 (t, 2H), 4.67 (d, 2H), 3.41 (t, 3H), 3.32 (s, 3H), 2.23 (d, 2H), 2.15 (m, 3H), 1.77 (m, 2H), 1.29 (s, 6H).

Example 18

4-[4-(3-cyclopropyl-[1,2,4]oxadiazol-5-yl)-piperidin-1-yl]-7-(2-fluoro-4-methanesulfonyl-phenyl)-thieno[3,2-d]pyrimidine

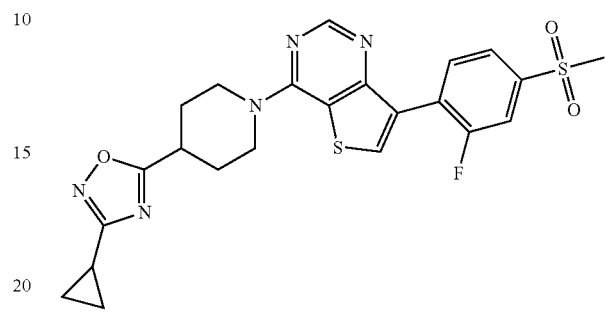

The procedure of Example 1 was repeated except for using 7-(2-fluoro-4-methanesulfonyl-phenyl)-4-methanesulfonyl-thieno[3,2-d]pyrimidine instead of 4-methanesulfonyl-7-(4-methanesulfonyl-phenyl)thieno[3,2-d]pyrimidine to obtain the title compound.

$^1$H NMR (300 MHz, DMSO-d$_6$): δ 8.67 (s, 1H), 8.47 (s, 1H), 8.13 (t, 1H), 7.94 (t, 2H), 4.65 (d, 2H), 3.39 (t, 3H), 2.23 (m, 3H), 1.77 (m, 2H), 1.26 (m, 3H), 1.15 (m, 2H), 0.99 (m, 2H).

Example 19

4-[4-(3-cyclopentyl-[1,2,4]oxadiazol-5-yl)-piperidin-1-yl]-7-(2-fluoro-4-methanesulfonyl-phenyl)-thieno[3,2-d]pyrimidine

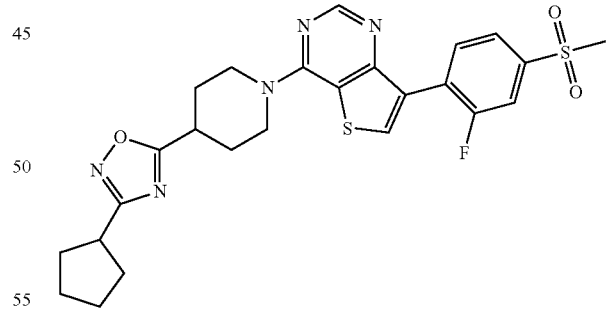

The procedure of Example 18 was repeated except for using 4-(3-cyclopentyl-[1,2,4]oxadiazol-5-yl)-piperidine instead of 4-(3-cyclopropyl-[1,2,4]oxadiazol-5-yl)-piperidine to obtain the title compound.

$^1$H NMR (300 MHz, DMSO-d$_6$): δ 8.46 (s, 1H), 8.45 (s, 1H), 7.92 (t, 1H), 7.74 (t, 2H), 4.54 (m, 2H), 3.55 (m, 2H), 3.17 (s, 3H), 3.03 (m 2H), 2.06 (m, 2H), 1.81-1.29 (m, 10H).

Hereinafter, a compound of Example 20 was prepared by the procedure shown in Reaction Scheme 8 below.

[Reaction Scheme 8]

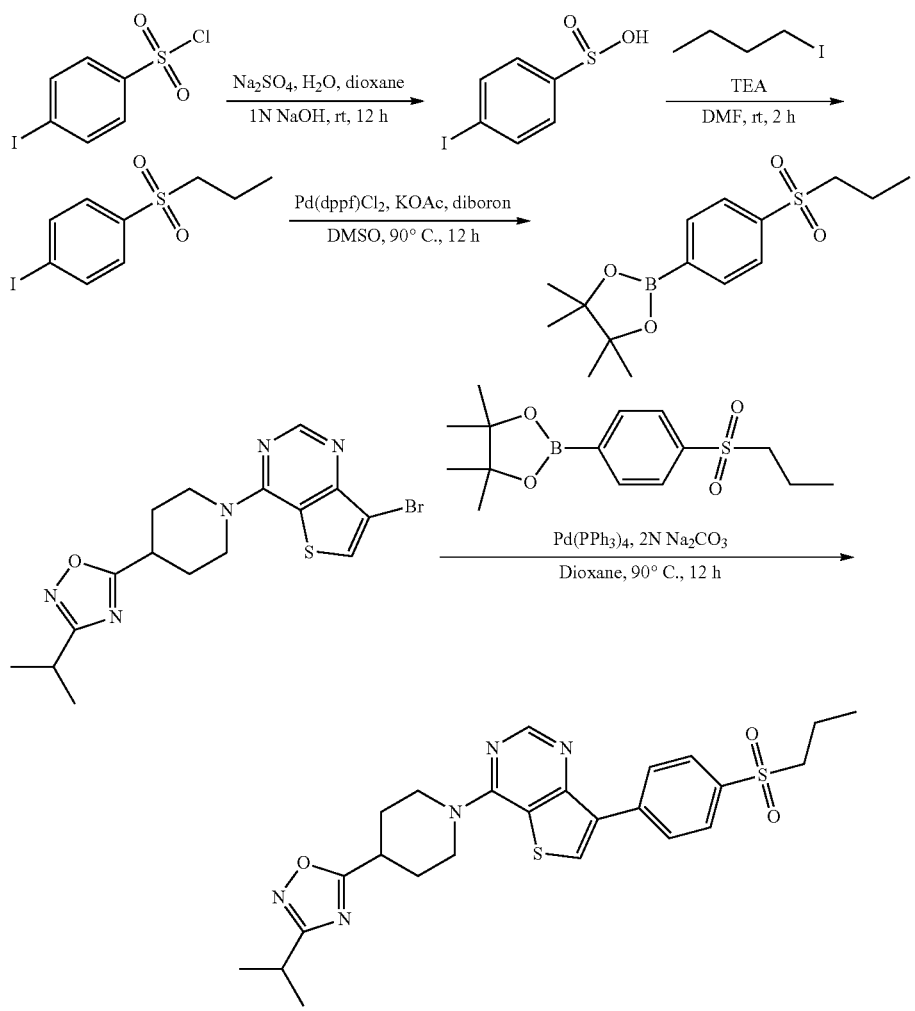

Example 20

4-[4-(3-isopropyl-[1,2,4]oxadiazol-5-yl)-piperidin-1-yl]-7-(4-(propylsulfonyl)phenyl)-thieno[3,2-d]pyrimidine Step 20-1) 4-iodo-benzenesulfinic acid

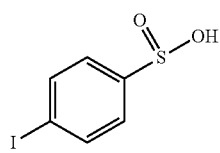

A solution of sodium carbonate (9.4 g, 74.375 mmol) in water (30 mL, 10 v/w) was dropwise added to a solution of 4-iodo-benzenesulfonyl chloride (3 g, 9.917 mmol) in 1,4-dioxane (15 mL, 5 v/w) at room temperature, followed by stirring at room temperature for 30 min. Then, 1N aqueous sodium hydroxide was dropwise added thereto so as to adjust the pH of the reaction mixture to 14, followed by stirring at room temperature for 12 hours. The reaction mixture was cooled to 0° C., and conc. $H_2SO_4$ solution was dropwise to adjust the pH of the reaction mixture to 1. The reaction mixture was extracted three times with ethyl acetate, and the organic layer thus obtained was washed with water. The washed layer was dried over anhydrous sodium sulfate, filtered, and concentrated under reduced pressure to obtain the title compound (2.5 g).

$^1$H NMR (300 MHz, DMSO-$d_6$): δ 7.95 (d, 2H), 7.45 (d, 2H), 3.38 (br, 1H)

Step 20-2) 4-iodo-4-(propane-1-sulfonyl)benzene

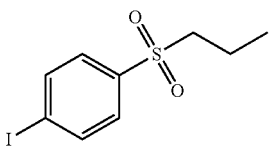

4-iodo-benzenesulfinic acid (250 mg, 0.933 mmol) obtained in Step 20-1 was dissolved in dimethylformamide (3 mL), and triethylamine (0.2 mL, 1.21 mmol) and 1-iodopropane (0.3 mL, 2.33 mmol) was sequentially added thereto, followed by stirring at room temperature for 2 hours. After completion of the reaction, the reaction mixture was mixed with water and extracted three times with ethyl acetate, and the organic layer thus obtained was sequentially washed with water and a saline solution. The washed organic layer was dried over anhydrous sodium sulfate, filtered, and concentrated under reduced pressure, followed by purification using column chromatography (Hex:EA=5:1) to obtain the title compound (200 mg).

$^1$H NMR (300 MHz, DMSO-d$_6$): δ 8.06 (d, 2H), 7.63 (d, 2H), 3.29 (t, 2H), 1.53 (m, 2H), 0.88 (t, 3H).

Step 20-3) 4,4,5,5-tetramethyl-2-[4-(propane-1-sulfonyl)-phenyl]-[1,3,2]dioxaborolane

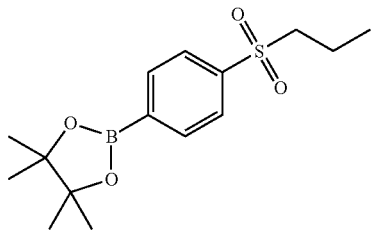 [SMILES: CCCS(=O)(=O)c1ccc(B2OC(C)(C)C(C)(C)O2)cc1]

4-iodo-4-(propane-1-sulfonyl)benzene (200 mg, 0.645 mmol) obtained in Step 20-2, Pd(dppf)Cl$_2$ (53 mg, 0.065 mmol), KOAc (190 mg, 1.935 mmol), pinacoldiborone (180 mg, 0.710 mmol) and dimethylsulfoxide (4 mL) were mixed together, and the internal air was replaced with argon gas. The reaction mixture was heated to 90° C., stirred for 14 hours, and cooled to room temperature. Then, the reaction mixture was mixed with water and extracted three times with ethyl acetate, and the organic layer thus obtained was washed with water and a saline solution. The washed organic layer was dried over anhydrous sodium sulfate, filtered, and concentrated under reduced pressure. The crystal obtained by adding hexane was filtered and concentrated to obtain the title compound (180 mg).

$^1$H NMR (300 MHz, DMSO-d$_6$): δ 7.91 (s, 4H), 3.28 (m, 2H), 1.53 (m, 2H), 1.32 (s, 12H), 0.92 (t, 3H)

Step 20-4) 4-[4-(3-isopropyl-[1,2,4]oxadiazol-5-yl)-piperidin-1-yl]-7-(4-(propylsulfonyl)phenyl)-thieno[3,2-d]pyrimidine

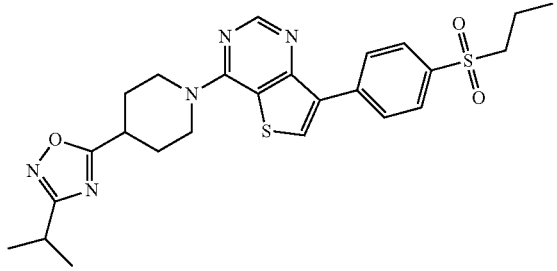 [SMILES: CCCS(=O)(=O)c1ccc(-c2csc3c(N4CCC(c5nc(C(C)C)no5)CC4)ncnc23)cc1]

The procedure of Example 12 was repeated except for using 4-(propylsulfonyl)phenyl-4,4,5,5-tetramethyl-[1,3,2]dioxaborolane instead of 2-(2-fluoro-4-methanesulfonyl-phenyl)-4,4,5,5-tetramethyl-[1,3,2]dioxaborolane in Step 12-2 to obtain the title compound.

$^1$H NMR (300 MHz, DMSO-d$_6$): δ 8.58 (s, 1H), 8.54 (s, 1H), 8.34 (d, 2H), 7.99 (d, 2H), 4.66 (m, 2H), 3.64 (s, 3H), 3.03 (m, 1H), 2.24 (m, 4H), 1.85 (m, 2H), 1.22 (m, 2H), 1.15 (t, 3H), 1.11 (d, 6H).

Example 21

7-(4-(cyclopropylsulfonyl)phenyl)-4-[4-(3-isopropyl-[1,2,4]oxadiazol-5-yl)-piperidin-1-yl]-thieno[3,2-d]pyrimidine

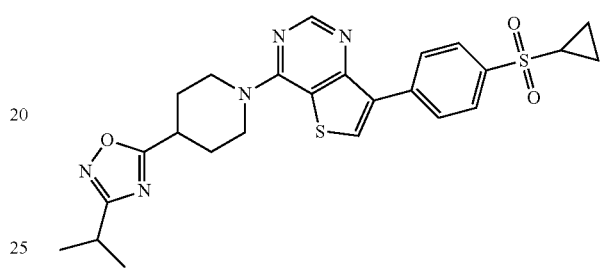

The procedure of Example 12 was repeated except for using 4-(cyclopropylsulfonyl)phenyl-4,4,5,5-tetramethyl-[1,3,2]dioxaborolane instead of 2-(2-fluoro-4-methanesulfonyl-phenyl)-4,4,5,5-tetramethyl-[1,3,2]dioxaborolane in Step 12-2 to obtain the title compound.

$^1$H NMR (300 MHz, DMSO-d$_6$): δ 8.57 (s, 1H), 8.56 (s, 1H), 8.32 (d, 2H), 7.98 (d, 2H), 4.66 (m, 2H), 3.03 (m, 1H), 2.24 (m, 2H), 1.85 (m, 2H), 1.22 (m, 2H), 1.11 (m, 2H), 0.99 (d, 6H), 0.86 (m, 2H), 0.77 (m, 2H).

Example 22

4-[4-(3-isopropyl-[1,2,4]oxadiazol-5-yl)-piperidin-1-yl]-7-(4-(isopropylsulfonyl)phenyl)-thieno[3,2-d]pyrimidine

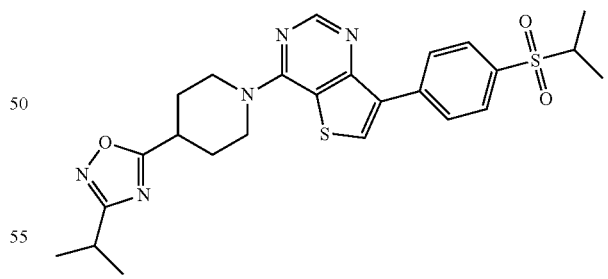

The procedure of Example 12 was repeated except for using 4-(isopropylsulfonyl)phenyl-4,4,5,5-tetramethyl-[1,3,2]dioxaborolane instead of 2-(2-fluoro-4-methanesulfonyl-phenyl)-4,4,5,5-tetramethyl-[1,3,2]dioxaborolane in Step 12-2 to obtain the title compound.

$^1$H NMR (300 MHz, DMSO-d$_6$): δ 8.57 (s, 1H), 8.56 (s, 1H), 8.32 (d, 2H), 7.98 (d, 2H), 4.66 (m, 2H), 3.66 (s, 3H), 3.03 (m, 1H), 2.24 (m, 2H), 1.85 (m, 3H), 1.22 (d, 6H), 1.11 (d, 6H).

Example 23

7-(4-(cyclopentylsulfonyl)phenyl)-4-[4-(3-isopropyl-[1,2,4]oxadiazol-5-yl)-piperidin-1-yl]-thieno[3,2-d]pyrimidine

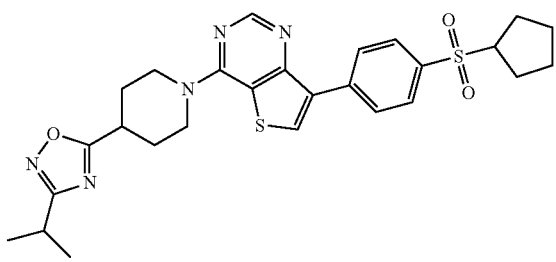 [SMILES: CC(C)c1noc(C2CCN(c3ncnc4c(-c5ccc(S(=O)(=O)C6CCCC6)cc5)csc34)CC2)n1]

The procedure of Example 12 was repeated except for using 4-(cyclopentylsulfonyl)phenyl-4,4,5,5-tetramethyl-[1,3,2]dioxaborolane instead of 2-(2-fluoro-4-methanesulfonyl-phenyl)-4,4,5,5-tetramethyl-[1,3,2]dioxaborolane in Step 12-2 to obtain the title compound.

$^1$H NMR (300 MHz, DMSO-d$_6$): δ 8.58 (s, 1H), 8.54 (s, 1H), 8.34 (d, 2H), 7.99 (d, 2H), 4.66 (m, 2H), 3.03 (m, 1H), 2.24 (m, 2H), 1.85 (m, 2H), 1.22 (d, 6H), 1.15 (m, 10H).

Example 24

7-4-(2-fluoro-(4-propylsulfonyl)phenyl)-4-[4-(3-isopropyl-[1,2,4]oxadiazol-5-yl)-piperidin-1-yl]-thieno[3,2-d]pyrimidine

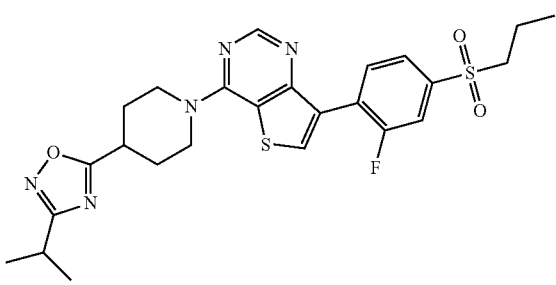 [SMILES: CCCS(=O)(=O)c1ccc(-c2csc3c(N4CCC(c5nc(C(C)C)no5)CC4)ncnc23)c(F)c1]

The procedure of Example 12 was repeated except for using 2-(2-fluoro-4-(propanesulfonyl)phenyl)-4,4,5,5-tetramethyl-[1,3,2]dioxaborolane instead of 2-(2-fluoro-4-methanesulfonyl-phenyl)-4,4,5,5-tetramethyl-[1,3,2]dioxaborolane in Step 12-2 to obtain the title compound.

$^1$H NMR (300 MHz, DMSO-d$_6$): δ 8.58 (s, 1H), 8.54 (s, 1H), 8.34 (t, 1H), 7.99 (t, 2H), 4.66 (m, 2H), 3.64 (s, 3H), 3.03 (m, 1H), 2.24 (m, 4H), 2.22 (m, 2H), 1.85 (m, 2H), 1.22 (d, 6H), 1.15 (t, 3H).

Preparation of Intermediate 6

7-bromo-4-chloro-5-ethyl-5H-pyrrolo[3,2-d]pyrimidine

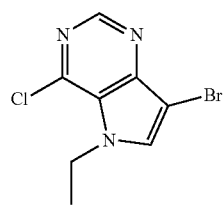

The procedure of Preparation Example 4 was repeated except for using ethyl iodide instead of methyl iodide in Step 4-4) to obtain the title compound.

$^1$H NMR (300 MHz, CDCl$_3$): δ 8.78 (s, 1H), 8.76 (s, 1H), 4.55 (q, 2H), 1.53 (t, 3H).

Preparation of Intermediate 7

1-isopropyl-piperidin-4-ol

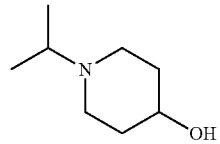

4-piperidinol (2.13 g, 21.1 mmol) was added to methanol (21 mL), and potassium carbonate (5.83 g, 42.2 mmol) and 2-bromopropane (11.2 g, 90.7 mmol) were further added thereto, followed by refluxing for 12 hours while stirring. Then, the reaction mixture was mixed with 2M HCl (40 mL) and extracted three times with dichloromethane (50 mL). The organic layer thus obtained was dried over anhydrous magnesium sulfate, and filtered and distilled under reduced pressure to obtain the title compound (2.2 g) as oil.

$^1$H NMR (300 MHz, CDCl$_3$): δ 3.65 (m, 1H), 2.76 (m, 2H), 2.26 (m, 3H), 1.92 (m, 2H), 1.56 (m, 2H), 1.02 (d, 6H).

Preparation of Intermediate 8

1-(4-hydroxy-piperidin-1-yl)-2,2-dimethyl-propan-1-one

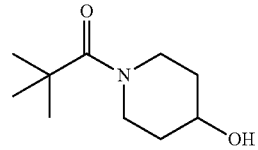

4-piperidinol (2 g, 19.8 mmol) was added to dichloromethane (20 mL), and cooled to an internal temperature of 0-5° C. Then, triethylamine (3.31 mL, 23.7 mmol) was added thereto and stirred for 30 min. Pivaloyl chloride (2.62 g, 21.8 mmol) was dropwise added thereto and heated to room temperature. The reaction mixture was stirred at room temperature for 5 hours. After completion of the reaction, the reaction mixture was mixed with a saturated aqueous solution of ammonium (50 mL) and extracted twice with dichloromethane (50 mL). The organic layer thus obtained was dried over anhydrous magnesium sulfate, and filtered and distilled under reduced pressure to obtain the title compound (3.9 g).

$^1$H NMR (300 MHz, CDCl$_3$): δ 4.09 (m, 2H), 4.03 (m, 1H), 3.26 (m, 2H), 2.25 (bs, 1H), 1.88 (m, 2H), 1.50 (m, 2H), 1.20 (s, 9H).

Hereinafter, a compound of Preparation Example 6 was prepared by the procedure shown in Reaction Scheme 9 below.

[Reaction Scheme 9]

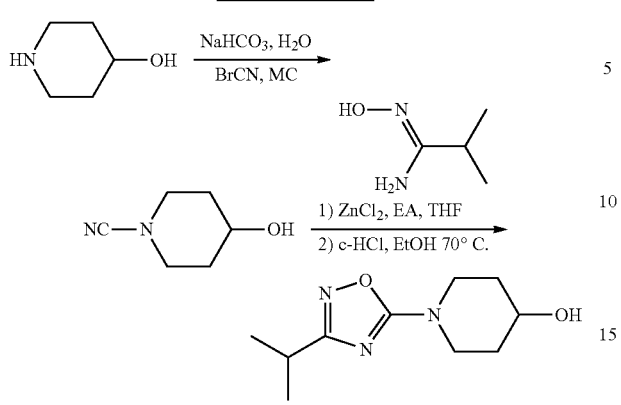

Preparation Example 6

1-(3-isopropyl-1,2,4-oxadiazol-5-yl)piperidin-4-ol

Step 6-1) 4-hydroxypiperidine-1-carbonitrile

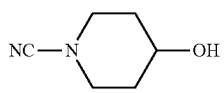

Sodium bicarbonate was dissolved in water, and a solution of 4-hydroxypiperidine in dichloromethane and BrCN were added thereto at 0° C. The reaction mixture was stirred at 0° C. for 30 min and further stirred at room temperature for 2 hours. After completion of the reaction, the reaction mixture was extracted twice with dichloromethane. The organic layer thus obtained was dried over anhydrous sodium sulfate, and concentrated under reduced pressure to obtain the title compound.

$^1$H NMR (300 MHz, DMSO-d$_6$): δ 3.90 (m, 1H), 3.46 (m, 2H), 3.09 (m, 2H), 1.94 (m, 2H), 1.67 (m, 2H).

Step 6-2) 1-(3-isopropyl-1,2,4-oxadiazol-5-yl)piperidin-4-ol

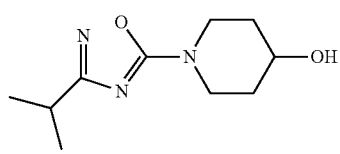

4-hydroxypiperidin-1-carbonitrile, N-hydroxyisopropylamidine ethyl acetate and tetrahydrofuran were mixed together, and ZnCl$_2$ was added thereto. After stirring for 2 hours, the resulting solid was filtered and washed with a solvent of ethyl acetate and hydrofuran (1:1). The solid was mixed with ethanol and 12N hydrochloric acid, and stirred at 70° C. overnight. After completion of the reaction, ethanol was removed by distillation under reduced pressure, and ethyl acetated was added thereto. Then, the mixture was neutralized with sodium bicarbonate, and the organic layer was dried over anhydrous sodium sulfate, followed by concentration under reduced pressure to obtain the title compound.

$^1$H NMR (300 MHz, DMSO-d$_6$): δ 4.81 (m, 1H), 3.73 (m, 2H), 3.30 (m, 2H), 2.77 (m, 2H), 1.77 (m, 2), 1.41 (m, 2H), 1.15 (d, 6H).

Preparation of Intermediate 9

1-(3-isopropyl-[1,2,4]oxadiazol-5-yl)pyrrolidin-3-ol

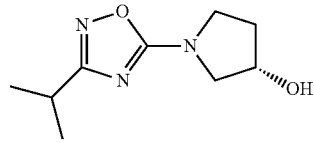

The procedure of Preparation Example 6 was repeated except for using (S)-pyrrolidin-3-ol instead of 4-hydroxypiperidine to obtain the title compound.

$^1$H NMR (300 MHz, CDCl$_3$): δ 4.62-4.59 (m, 1H), 3.76-3.57 (m, 4H), 2.96-2.85 (m, 1H), 2.13-2.06 (m, 2H), 1.29 (d, 6H).

Preparation of Intermediate 10

1-(3-isopropyl-1,2,4-oxadiazol-5-yl)piperidin-4-ol

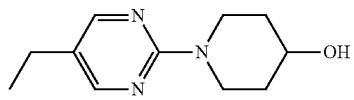

4-hydroxypiperidine was dissolved in acetonitrile, and 2-chloro-5-ethylpyrimidine and DIPEA were added thereto, followed by refluxing overnight. Then, the reaction was terminated by addition of sodium bicarbonate, and the reaction mixture was extracted twice with ethyl acetate. The organic layer thus obtained was dried over anhydrous sodium sulfate, and concentrated under reduced pressure to obtain the title compound.

$^1$H NMR (300 MHz, DMSO-d$_6$): δ 8.22 (s, 2H), 4.22 (m, 2H), 3.71 (m, 1H), 3.18 (m, 2H), 2.41 (dd, 2H), 1.75 (m, 2H), 1.27 (m, 2H), 1.12 (t, 3H).

Preparation of Intermediate 11

4-hydroxy-piperidine-1-carboxylic acid tert-butylamide

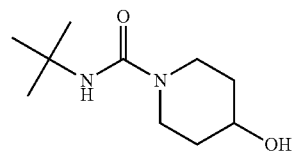

Piperidin-4-ol (1 g) was dissolved in dichloromethane, and tert-butyl isocyanate was added thereto. Then, triethylamine was added thereto at room temperature, and the reaction mixture was stirred for 2 hours. After completion of the reaction, the reaction mixture was concentrated under reduced pressure to remove the solvent, crystallized in the presence of ether 50 mL, and filtered to obtain the title compound (1.8 g) as a white solid.

$^1$H NMR (300 MHz, DMSO-d$_6$): δ 5.67 (s, 1H), 4.60 (d, 1H), 3.68-3.61 (m, 2H), 3.57-3.53 (m, 1H), 2.82-2.74 (m, 2H), 1.66-1.61 (m, 2H), 1.23 (s, 9H).

Hereinafter, a compound of Example 25 was prepared by the procedure shown in Reaction Scheme 10 below.

[Reaction Scheme 10]

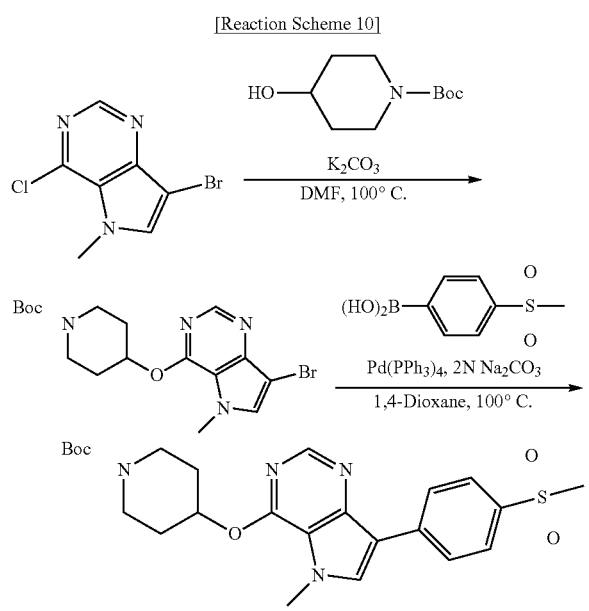

Example 25 tert-butyl 4-(5-methyl-7-(4-methanesulfonyl-phenyl)-5H-pyrrolo[3,2-d]pyrimidin-4-yloxy)piperidine-1-carboxylate Step 25-1) tert-butyl 4-(7-bromo-5-methyl-5H-pyrrolo[3,2-d]pyrimidin-4-yloxy)piperidine-1-carboxylate

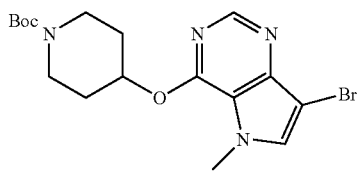 [SMILES: Cn1cc(Br)c2ncnc(OC3CCNCC3)c21]

To 7-bromo-4-chloro-5-methyl-5H-pyrrolo[3,2-d]pyrimidine (200 mg) obtained in Step 4-4 of Preparation Example 4, t-butyl 4-hydroxypiperidine-1-carboxylate (180 mg), K$_2$CO$_3$ (168 mg) and N,N-dimethylformamide (4 ml) were added, and stirred at 100° C. for 12 hours in a hermetically sealed reactor. The reaction mixture was cooled to room temperature, extracted with ethyl acetate and distilled water, and the organic layer thus obtained was washed with water and a saline solution. Subsequently, the washed organic layer was dried over anhydrous sodium sulfate and concentrated under reduced pressure to obtain the title compound.

$^1$H NMR (300 MHz, DMSO-d$_6$): δ 8.41 (s, 1H), 7.88 (s, 1H), 5.54 (m, 1H), 4.00 (s, 3H), 3.56 (m, 2H), 3.40 (m, 2H), 1.96 (m, 2H), 1.77 (m, 2H), 1.41 (s, 9H).

Step 25-2) tert-butyl 4-(5-methyl-7-(4-methanesulfonyl-phenyl)-5H-pyrrolo[3,2-d]pyrimidin-4-yloxy)piperidine-1-carboxylate

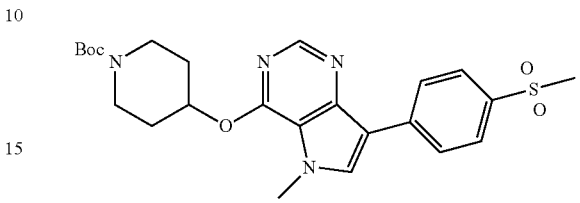

tert-butyl 4-(7-bromo-5-methyl-5H-pyrrolo[3,2-d]pyrimidin-4-yloxy)piperidine-1-carboxylate (15 mg), 4-methanesulfonyl-phenylboronic acid (33 mg), Pd(PPh$_3$)$_4$ (7.5 mg) and 2N Na$_2$CO$_3$ (0.33 mL) were mixed with 1,4-dioxane (2 mL), and stirred at 100° C. for 12 hours in a hermetically sealed reactor. The reaction mixture was cooled to room temperature, extracted with ethyl acetate and distilled water, and the organic layer thus obtained was washed with water and a saline solution. Subsequently, the washed organic layer was dried over anhydrous sodium sulfate and concentrated under reduced pressure to obtain the title compound (15 mg).

$^1$H NMR (300 MHz, DMSO-d$_6$): δ 8.53 (s, 1H), 8.47 (s, 1H), 8.41 (d, 2H), 7.95 (d, 2H), 5.57 (m, 1H), 4.09 (s, 3H), 3.59 (m, 2H), 3.46 (m, 2H), 3.22 (s, 3H), 1.98 (m, 2H), 1.80 (m, 2H), 1.43 (s, 9H).

Example 26

5-methyl-7-(4-methanesulfonyl-phenyl)-4-(piperidin-4-yloxy)-5H-pyrrolo[3,2-d]pyrimidine

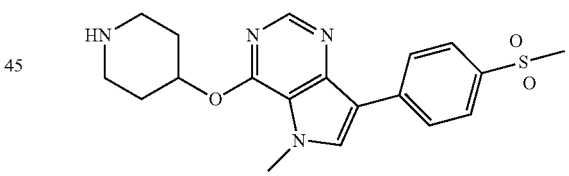

To tert-butyl 4-(5-methyl-7-(4-methanesulfonyl-phenyl)-5H-pyrrolo[3,2-d]pyrimidin-4-yloxy)piperidine-1-carboxylate obtained in Example 25, dichloromethane (1 mL) and trifluoroacetic acid (1 mL) were added, and stirred for 1 hour. After completion of the reaction, the reaction was terminated with saturated sodium bicarbonate, and dichloromethane layer was extracted and washed with a saline solution. Subsequently, the washed layer was dried over anhydrous sodium sulfate, and filtered and distilled under reduced pressure to obtain the title compound.

$^1$H NMR (300 MHz, DMSO-d$_6$): δ 8.51 (s, 1H), 8.44 (d, 2H), 8.38 (s, 1H), 7.94 (d, 2H), 5.44 (m, 1H), 4.09 (s, 3H), 3.21 (s, 3H), 2.99 (m, 2H), 2.64 (m, 2H), 2.02 (m, 2H), 1.71 (m, 2H).

Hereinafter, a compound of Example 27 was prepared by the procedure of Reaction Scheme 11 below.

[Reaction Scheme 11]

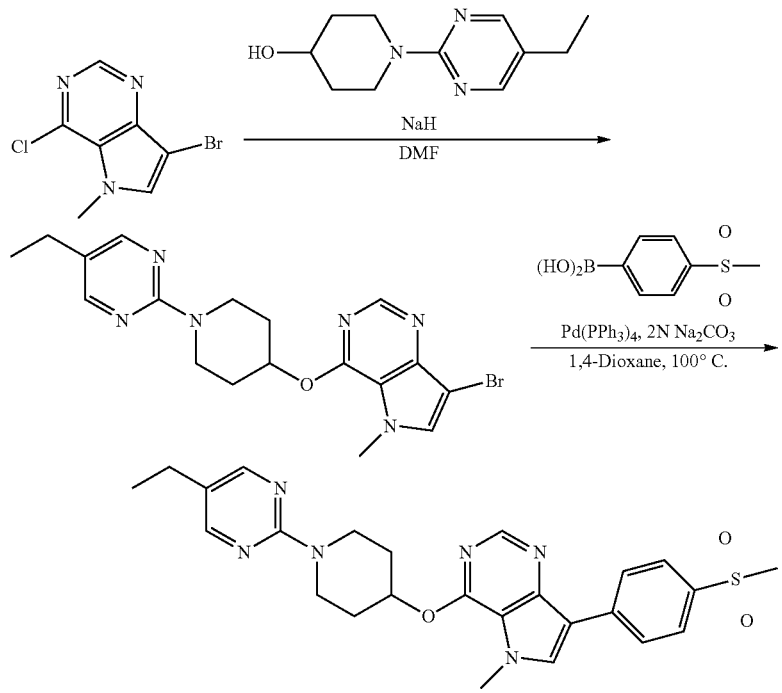

Example 27

4-(1-(5-ethylpyrimidin-2-yl)piperidin-4-yloxy)-5-methyl-7-(4-methanesulfonyl-phenyl)-5H-pyrrolo[3,2-d]pyrimidine

Step 27-1) 7-bromo-4-(1-(5-ethylpyrimidin-2-yl)piperidin-4-yloxy)-5-methyl-5H-pyrrolo[3,2-d]pyrimidine

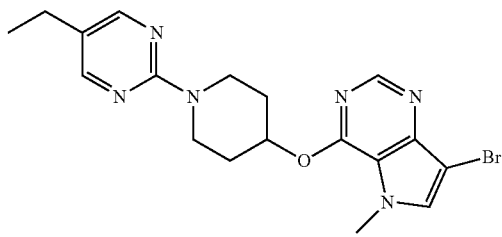 [SMILES: CCc1cnc(N2CCC(Oc3ncnc4c(Br)cn(C)c34)CC2)nc1]

1-(5-ethylpyrimidin-2-yl)piperidin-4-ol (93 mg) was added to DMF (5 mL), and cooled to 0° C. Then, NaH (27 mg) was added thereto, and stirred for 30 min. 7-bromo-4-chloro-5-methyl-5H-pyrrolo[3,2-d]pyrimidine (100 mg) was added thereto, and stirred at room temperature for 12 hours. The reaction mixture was extracted with ethyl acetate and distilled water, and the organic layer thus obtained was washed with water and a saline solution. Subsequently, the washed organic layer was dried over anhydrous sodium sulfate, and concentrated under reduced pressure to obtain the title compound.

$^1$H NMR (300 MHz, DMSO-$d_6$): δ 8.42 (s, 1H), 8.27 (s, 2H), 7.87 (s, 1H), 5.62 (m, 1H), 4.04 (s, 3H), 4.00 (m, 2H), 3.79 (m, 2H), 2.44 (dd, 2H), 2.03 (m, 2H), 1.77 (m, 2H), 1.36 (t, 3H).

Step 27-2) 4-(1-(5-ethylpyrimidin-2-yl)piperidin-4-yloxy)-5-methyl-7-(4-methanesulfonyl-phenyl)-5H-pyrrolo[3,2-d]pyrimidine

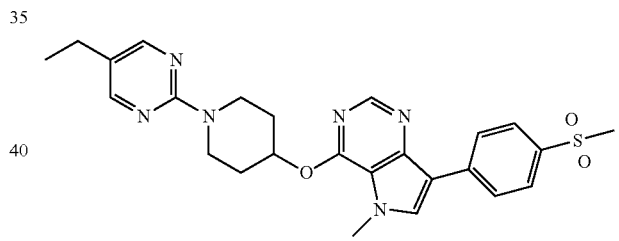

The procedure of Example 25 was repeated except for using 7-bromo-4-(1-(5-ethylpyrimidin-2-yl)piperidin-4-yloxy)-5-methyl-5H-pyrrolo[3,2-d]pyrimidine instead of tert-butyl 4-(7-bromo-5-methyl-5H-pyrrolo[3,2-d]pyrimidin-4-yloxy)piperidine-1-carboxylate in Step 25-2 to obtain the title compound.

$^1$H NMR (300 MHz, DMSO-$d_6$): δ 8.54 (s, 1H), 8.45 (s, 1H), 8.41 (d, 2H), 8.27 (s, 2H), 7.94 (d, 2H), 5.65 (m, 1H), 4.08 (s, 3H), 4.02 (m, 2H), 3.83 (m, 2H), 3.22 (s, 3H), 2.44 (dd, 2H), 2.06 (m, 2H), 1.84 (m, 2H), 1.14 (t, 3H).

Example 28

5-methyl-7-(4-methanesulfonyl-phenyl)-4-(1-(5-(trifluoromethyl)pyrimidin-2-yl)piperidin-4-yloxy)-5H-pyrrolo[3,2-d]pyrimidine

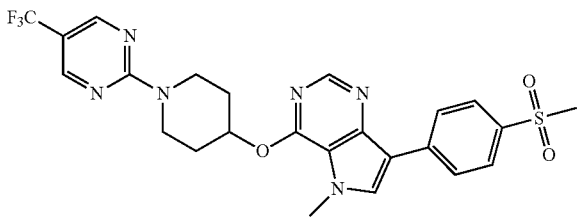

The procedure of Example 27 was repeated except for using 1-(5-(trifluoromethyl)pyrimidin-2-yl)piperidin-4-ol instead of 1-(5-ethylpyrimidin-2-yl)piperidin-4-ol in Step 27-1 to obtain the title compound.

$^1$H NMR (300 MHz, DMSO-$d_6$): δ 8.70 (s, 2H), 8.53 (s, 1H), 8.43 (s, 1H), 8.39 (d, 2H), 7.93 (d, 2H), 5.66 (m, 1H), 4.07 (s, 3H), 4.02 (m, 4H), 3.20 (s, 3H), 2.12 (m, 2H), 1.91 (m, 2H).

Example 29

4-(1-(5-ethylpyrimidin-2-yl)piperidin-4-yloxy)-7-(2-fluoro-4-methanesulfonyl-phenyl)-5-methyl-5H-pyrrolo[3,2-d]pyrimidine

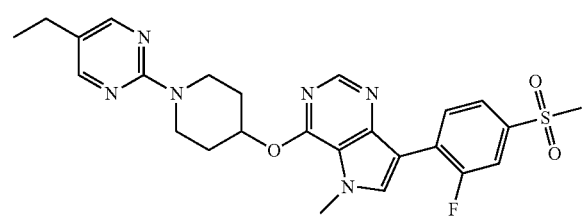 [SMILES: CCc1cnc(N2CCC(Oc3ncnc4c(-c5ccc(S(C)(=O)=O)cc5F)cn(C)c34)CC2)nc1]

The procedure of Example 27 was repeated except for using 2-(2-fluoro-4-methanesulfonyl-phenyl)-4,4,5,5-tetramethyl-[1,3,2]dioxaborolane instead of 4-methanesulfonyl-phenyl-4,4,5,5-tetramethyl-[1,3,2]dioxaborolane in Step 27-2 to obtain the title compound.

$^1$H NMR (300 MHz, DMSO-$d_6$): δ 9.04 (t, 1H), 8.56 (s, 1H), 8.28 (s, 2H), 8.27 (d, 1H), 7.87 (s, 1H), 7.84 (m, 1H), 5.64 (m, 1H), 4.12 (s, 3H), 4.03 (m 2H), 3.81 (m, 2H), 3.29 (s, 3H), 2.49 (q, 2H), 2.07 (m, 2H), 1.84 (m, 2H), 1.14 (t, 3H).

Example 30

7-(2-fluoro-4-(methanesulfonyl(phenyl)-5-methyl-4-(1-(5-propylpyrimidin-2-yl)piperidin-4-yloxy)-5H-pyrrolo[3,2-d]pyrimidine

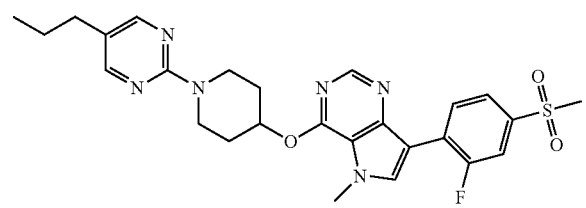 [SMILES: CCCc1cnc(N2CCC(Oc3ncnc4c(-c5ccc(S(C)(=O)=O)cc5F)cn(C)c34)CC2)nc1]

The procedure of Example 29 was repeated except for using 1-(5-propylpyrimidin-2-yl)piperidin-4-ol instead of 1-(5-ethylpyrimidin-2-yl)piperidin-4-ol to obtain the title compound.

$^1$H NMR (300 MHz, DMSO-$d_6$): δ 9.09 (t, 1H), 8.26 (m, 3H), 7.87 (s, 1H), 7.83 (m, 1H), 5.64 (m, 1H), 4.12 (s, 3H), 4.03 (m, 2H), 3.82 (m, 2H), 2.38 (t, 2H), 2.11 (m, 2H), 1.88 (m, 2H), 1.53 (q, 2H), 0.88 (t, 3H).

Example 31

7-(2-fluoro-4-methanesulfonyl-phenyl)-5-methyl-4-(1-(5-(trifluoromethyl)pyrimidin-2-yl)piperidin-4-yloxy)-5H-pyrrolo[3,2-d]pyrimidine

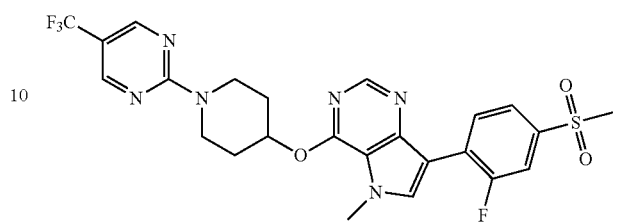

The procedure of Example 28 was repeated except for using 2-(2-fluoro-4-methanesulfonyl-phenyl)-4,4,5,5-tetramethyl-[1,3,2]dioxaborolane instead of 4-methanesulfonyl-phenyl-4,4,5,5-tetramethyl-[1,3,2]dioxaborolane to obtain the title compound.

$^1$H NMR (300 MHz, DMSO-$d_6$): δ 9.09 (t, 1H), 8.73 (s, 2H), 8.57 (s, 1H), 8.27 (d, 2H), 7.88 (s, 1H), 7.84 (m, 1H), 5.71 (m, 1H), 4.14 (s, 3H), 4.05 (m, 4H), 3.29 (s, 3H), 2.11 (m, 2H), 1.94 (m, 2H).

Example 32

5-ethyl-4-(1-(5-ethylpyrimidin-2-yl)piperidin-4-yloxy)-7-(4-methanesulfonyl-phenyl)-5H-pyrrolo[3,2-d]pyrimidine

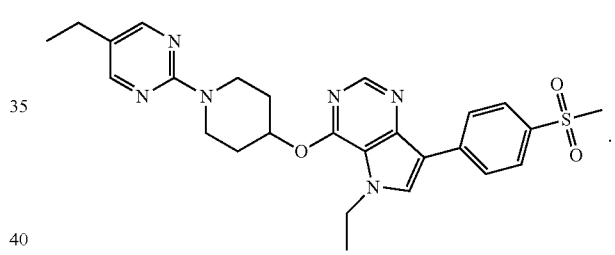

The procedure of Example 27 was repeated except for using 7-bromo-4-chloro-5-ethyl-5H-pyrrolo[3,2-d]pyrimidine instead of 7-bromo-4-chloro-5-methyl-5H-pyrrolo[3,2-d]pyrimidine to obtain the title compound.

$^1$H NMR (300 MHz, DMSO-$d_6$): δ 8.59 (s, 1H), 8.2 (m, 3H), 7.96 (d, 2H), 7.66 (s, 2H), 5.74 (m, 1H), 4.45 (m, 2H), 4.20 (m, 2H), 3.77 (m, 2H), 3.00 (s, 3H), 2.47 (q, 2H), 2.18 (m, 2H), 1.93 (m, 2H), 1.50 (t, 3H), 1.20 (t, 3H).

Example 33

5-ethyl-4-(1-(5-ethylpyrimidin-2-yl)piperidin-4-yloxy)-7-(2-fluoro-4-methanesulfonyl-phenyl)-5H-pyrrolo[3,2-d]pyrimidine

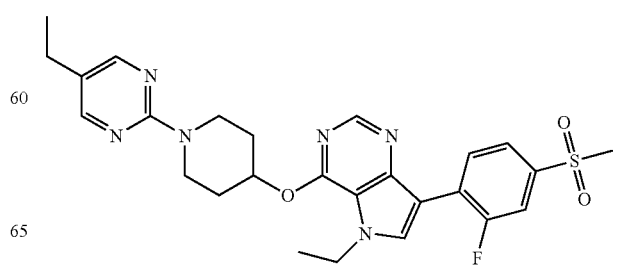

The procedure of Example 32 was repeated except for using 2-(2-fluoro-4-methanesulfonyl-phenyl)-4,4,5,5-tetramethyl-1,3,2-dioxaborolane instead of 4-methanesulfonyl-phenyl-4,4,5,5-tetramethyl-[1,3,2]dioxaborolane to obtain the title compound.

¹H NMR (300 MHz, DMSO-d₆): δ 9.09 (m, 1H), 8.58 (s, 1H), 8.33 (d, 2H), 8.28 (s, 2H), 7.87 (s, 1H), 7.56 (m, 1H), 5.68 (m, 1H), 4.49 (q, 2H), 4.04 (m, 2H), 3.80 (m, 2H), 3.28 (s, 3H), 2.45 (q, 2H), 2.09 (m, 2H), 1.86 (m, 2H), 1.44 (t, 3H), 1.12 (t, 3H)

Example 34

5-ethyl-7-(2-fluoro-4-methanesulfonyl-phenyl)-4-(1-(5-propylpyrimidin-2-yl)piperidin-4-yloxy)-5H-pyrrolo[3,2-d]pyrimidine

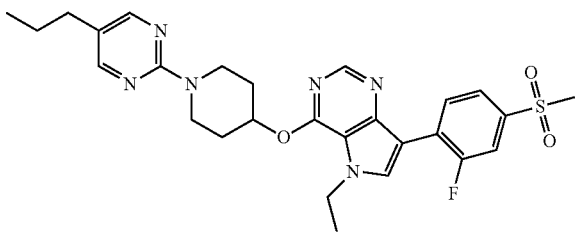 [SMILES: CCCc1cnc(N2CCC(Oc3ncnc4c(-c5ccc(S(C)(=O)=O)cc5F)cn(CC)c34)CC2)nc1]

The procedure of Example 33 was repeated except for using 1-(5-propylpyrimidin-2-yl)piperidin-4-ol instead of 1-(5-ethylpyrimidin-2-yl)piperidin-4-ol to obtain the title compound.

¹H NMR (300 MHz, DMSO-d₆): δ 9.09 (t, 1H), 8.58 (s, 1H), 8.34 (d, 1H), 8.25 (s, 2H), 7.87 (s, 1H), 7.85 (m, 1H), 5.68 (m, 1H), 4.49 (q, 2H), 4.03 (m, 2H), 3.83 (m, 2H), 3.29 (s, 3H), 2.39 (t, 3H), 2.09 (m, 2H), 1.86 (m, 2H), 1.52 (q, 2H), 1.43 (t, 3H), 0.89 (t, 3H).

Example 35

3-isopropyl-5-(4-(5-methyl-7-(4-methanesulfonyl-phenyl)-5H-pyrrolo[3,2-d]pyrimidin-4-yloxy)piperidin-1-yl)-1,2,4-oxadiazole

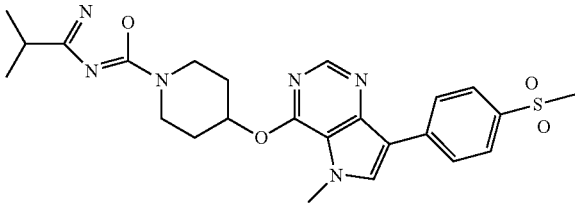

The procedure of Example 27 was repeated except for using 1-(3-isopropyl-1,2,4-oxadiazol-5-yl)piperidin-4-ol instead of 1-(5-ethylpyrimidin-2-yl)piperidin-4-ol to obtain the title compound.

¹H NMR (300 MHz, DMSO-d₆): δ 8.53 (s, 1H), 8.42 (d, 2H), 8.41 (s, 1H), 7.94 (d, 2H), 5.62 (m, 1H), 4.09 (s, 3H), 3.72 (m, 4H), 3.20 (s, 3H), 2.80 (m, 1H), 2.12 (m, 2H), 1.99 (m, 2H), 1.14 (dd, 6H).

Example 36

5-(4-(7-(2-fluoro-4-methanesulfonyl-phenyl)-5-methyl-5H-pyrrolo[3,2-d]pyrimidin-4-yloxy)piperidin-1-yl)-3-isopropyl-1,2,4-oxadiazole

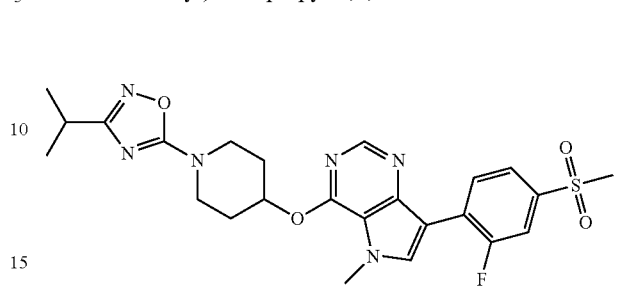

The procedure of Example 35 was repeated except for using 2-(2-fluoro-4-methanesulfonyl-phenyl)-4,4,5,5-tetramethyl-[1,3,2]dioxaborolane instead of 4-methanesulfonyl-phenylboronic acid to obtain the title compound.

¹H NMR (300 MHz, DMSO-d₆): δ 9.08 (t, 1H), 8.56 (s, 1H), 8.27 (d, 1H), 7.87 (s, 1H), 7.84 (m, 1H), 5.63 (m, 1H), 4.13 (s, 3H), 3.74 (m, 4H), 3.28 (s, 3H), 2.83 (m, 1H), 2.11 (m, 2H), 1.98 (m, 2H), 1.20 (d, 6H).

Example 37

5-(4-(5-ethyl-7-(2-fluoro-4-methanesulfonyl-phenyl)-5H-pyrrolo[3,2-d]pyrimidin-4-yloxy)piperidin-1-yl)-3-isopropyl-1,2,4-oxadiazole

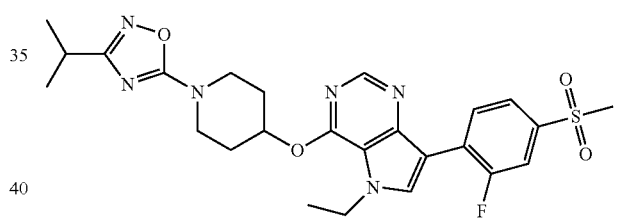

The procedure of Example 36 was repeated except for using 7-bromo-4-chloro-5-ethyl-5H-pyrrolo[3,2-d]pyrimidine instead of 7-bromo-4-chloro-5-methyl-5H-pyrrolo[3,2-d]pyrimidine to obtain the title compound.

¹H NMR (300 MHz, DMSO-d₆): δ 9.07 (t, 1H), 8.57 (s, 1H), 8.33 (d, 2H), 7.87 (s, 1H), 7.83 (m, 1H), 5.66 (m, 1H), 4.47 (q, 2H), 3.71 (m, 4H), 3.28 (s, 3H), 2.82 (m, 1H), 2.15 (m, 2H), 1.93 (m, 2H), 1.43 (t, 3H), 1.19 (d, 6H).

Example 38

4-[1-(3-isopropyl-[1,2,4]oxadiazol-5-yl)-pyrrolidin-3-yloxy]-7-(4-methanesulfonyl-phenyl)-5-methyl-5H-pyrrolo[3,2-d]pyrimidine

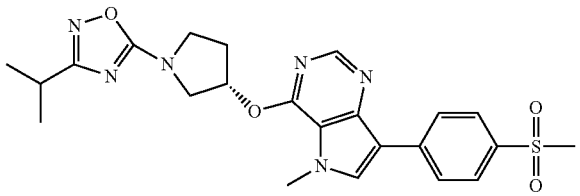 [SMILES: CC(C)c1noc(N2CC[C@H](Oc3ncnc4c(-c5ccc(S(C)(=O)=O)cc5)cn(C)c34)C2)n1]

The procedure of Example 27 was repeated except for using 1-(3-isopropyl-[1,2,4]oxadiazol-5-yl)pyrrolidin-3-ol instead of 1-(5-ethylpyrimidin-2-yl)piperidin-4-ol to obtain the title compound.

$^1$H NMR (300 MHz, CDCl$_3$): δ 8.58 (s, 1H), 8.23 (d, 2H), 7.96 (d, 2H), 7.59 (s, 1H), 6.02 (s, 1H), 4.04 (s, 3H), 4.00-3.80 (m, 4H), 3.06 (s, 3H), 2.91 (m, 1H), 2.45 (q, 2H), 1.30-1.25 (m, 7H).

Example 39

4-[1-(5-ethylpyrimidin-2-yl)-pyrrolidin-3-yloxy]-7-(4-methanesulfonyl-phenyl)-5-methyl-5H-pyrrolo[3,2-d]pyrimidine

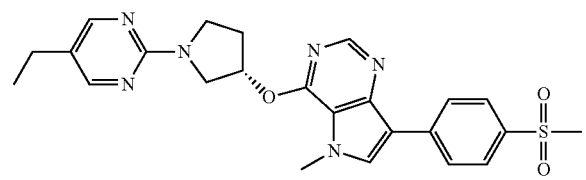 [SMILES: CCc1cnc(N2CC[C@H](Oc3ncnc4c(-c5ccc(S(C)(=O)=O)cc5)cn(C)c34)C2)nc1]

The procedure of Example 27 was repeated except for using (S)-1-(5-ethylpyrimidin-2-yl)-pyrrolidin-3-ol instead of 1-(5-ethylpyrimidin-2-yl)piperidin-4-ol to obtain the title compound.

$^1$H NMR (300 MHz, DMSO-d$_6$): δ 8.57 (s, 1H), 8.42 (d, 2H), 8.36 (s, 1H), 7.94 (d, 2H), 5.92 (s, 1H), 3.96 (s, 3H), 3.87 (s, 2H), 3.80-3.79 (m, 1H), 3.68-3.65 (m, 1H), 3.21 (s, 3H), 2.42 (q, 2H), 1.11 (t, 3H).

Example 40

4-[7-(4-methanesulfonyl-phenyl)-5-methyl-5H-pyrrolo[3,2-d]pyrimidin-4-yloxy]piperidin-1-carboxylic acid tert-butylamide

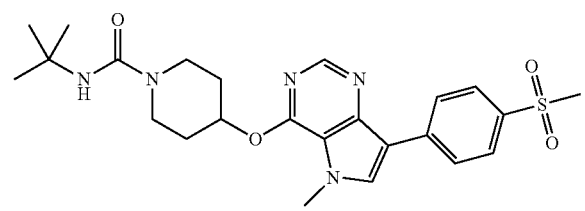 [SMILES: Cn1cc(-c2ccc(S(C)(=O)=O)cc2)c2ncnc(OC3CCN(C(=O)NC(C)(C)C)CC3)c21]

The procedure of Example 27 was repeated except for using 4-hydroxy-piperidin-1-carboxylic acid tert-butylamide instead of 1-(5-ethylpyrimidin-2-yl)piperidin-4-ol to obtain the title compound.

$^1$H NMR (300 MHz, CDCl$_3$): δ 8.56 (s, 1H), 8.24 (d, 2H), 7.97 (d, 2H), 7.59 (s, 1H), 5.62 (s, 1H), 4.11 (s, 3H), 3.67-3.60 (m, 2H), 3.37-3.30 (m, 2H), 3.06 (s, 3H), 2.17-2.10 (m, 2H), 1.93-1.86 (m, 2H), 1.37 (s, 9H).

Example 41

4-(4-(1-(3-isopropyl-1,2,4-oxadiazol-5-yl)piperidin-4-yloxy)-5-methyl-5H-pyrrolo[3,2-d]piperidin-7-yl)benzenamine

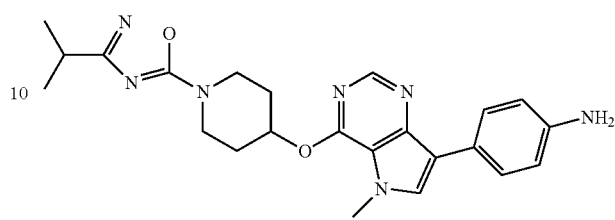

The procedure of Example 27 was repeated except for using 7-bromo-4-(1-(3-isopropyl-1,2,4-oxadiazol-5-yl)piperidin-4-yloxy)-5-methyl-5H-pyrrolo[3,2-d]pyrimidine and 4-aminophenylboronic acid instead of 7-bromo-4-(1-(5-ethylpyrimidin-2-yl)piperidin-4-yloxy)-5-methyl-5H-pyrrolo[3,2-d]pyrimidine and 4-methanesulfonyl-phenylboronic acid in Step 27-2 to obtain the title compound.

$^1$H NMR (300 MHz, DMSO-d$_6$): δ 8.39 (s, 1H), 7.87 (s, 1H), 7.77 (d, 2H), 6.59 (d, 2H), 5.56 (m, 1H), 5.01 (s, NH2), 4.09 (s, 3H), 3.55 (m, 2H), 3.44 (m, 2H), 2.69 (m, 1H), 2.01 (m, 2H), 1.83 (m, 2H), 1.06 (dd, 6H).

Example 42

3-isopropyl-5-(4-(5-methyl-7-(4-nitrophenyl)-5H-pyrrolo[3,2-d]pyrimidin-4-yloxy)piperidin-1-yl)-1,2,4-oxadiazole

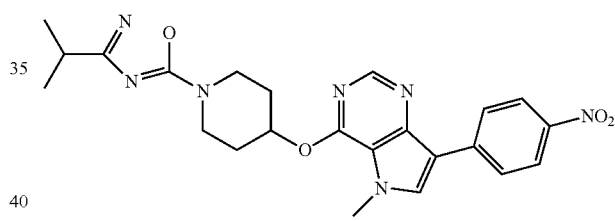

The procedure of Example 27 was repeated except for using 7-bromo-4-(1-(3-isopropyl-1,2,4-oxadiazol-5-yl)piperidin-4-yloxy)-5-methyl-5H-pyrrolo[3,2-d]pyrimidine and 4-nitrophenylboronic acid instead of 7-bromo-4-(1-(5-ethylpyrimidin-2-yl)piperidin-4-yloxy)-5-methyl-5H-pyrrolo[3,2-d]pyrimidine and 4-methanesulfonyl-phenylboronic acid in Step 27-2 to obtain the title compound.

$^1$H NMR (300 MHz, DMSO-d$_6$): δ 8.53 (s, 1H), 7.79 (d, 2H), 7.35 (s, 1H), 6.77 (d, 2H), 5.63 (m, 1H), 3.94 (m, 2H), 3.70 (m, 2H), 2.38 (m, 1H), 2.03 (m, 2H), 1.88 (m, 2H), 1.21 (d, 6H).

Example 43

4-{4-[1-(5-ethylpyrimidin-2-yl)-piperidin-4-yloxy]-5-methyl-5H-pyrrolo[3,2-d]pyrimidin-7-yl}-benzonitrile

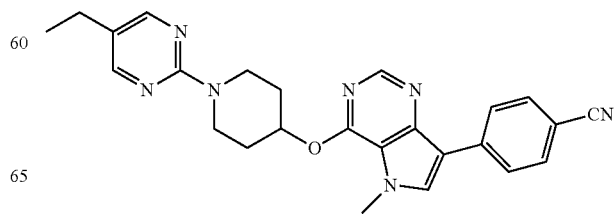

The procedure of Example 27 was repeated except for using 4-cyanophenylboronic acid instead of 4-methanesulfonyl-phenylboronic acid in Step 27-2 to obtain the title compound.

$^1$H NMR (300 MHz, DMSO-d$_6$): δ 8.57 (s, 1H), 8.2 (s, 2H), 8.15 (d, 2H), 7.63 (d, 2H), 7.51 (s, 1H), 5.69 (m, 1H), 4.21 (m, 2H), 4.07 (s, 3H), 3.76 (m, 2H), 2.49 (q, 2H), 2.17 (m, 2H), 1.93 (m, 2H), 1.20 (t, 3H).

Example 44

1-(4-{4-[1-(5-ethylpyrimidin-2-yl)-piperidin-4-yloxy]-5-methyl-5H-pyrrolo[3,2-d]pyrimidin-7-yl}-phenyl)-ethanone

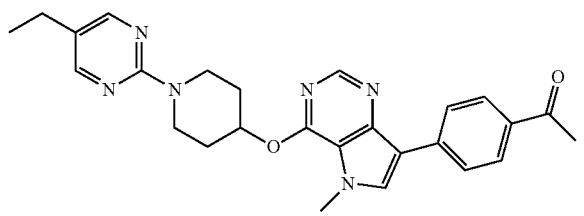 [SMILES: CCc1cnc(N2CCC(Oc3ncnc4c(-c5ccc(C(C)=O)cc5)cn(C)c34)CC2)nc1]

The procedure of Example 27 was repeated except for using 4-acetylphenylboronic acid instead of 4-methanesulfonyl-phenylboronic acid in Step 27-2 to obtain the title compound.

$^1$H NMR (300 MHz, DMSO-d$_6$): δ 8.59 (s, 1H), 8.2 (s, 2H), 8.15 (d, 2H), 8.01 (d, 2H), 7.55 (s, 1H), 5.71 (m, 1H), 4.21 (m, 2H), 4.09 (s, 3H), 3.78 (m, 2H), 2.61 (s, 3H), 2.47 (q, 2H), 2.18 (m, 2H), 1.93 (m, 2H), 1.20 (t, 3H).

Example 45

4-(1-isopropyl-piperidin-4-yloxy)-7-(4-methanesulfonyl-phenyl)-5-methyl-5H-pyrrolo[3,2-d]pyrimidine

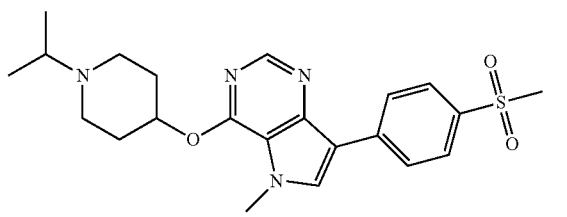 [SMILES: CC(C)N1CCC(Oc2ncnc3c(-c4ccc(S(C)(=O)=O)cc4)cn(C)c23)CC1]

The procedure of Example 27 was repeated except for using 1-isopropyl-piperidin-4-ol instead of 1-(5-ethylpyrimidin-2-yl)piperidin-4-ol to obtain the title compound.

$^1$H NMR (300 MHz, DMSO-d$_6$): δ 8.57 (s, 1H), 8.23 (d, 2H), 7.97 (d, 2H), 7.57 (s, 1H), 5.45 (m, 1H), 3.07 (s, 3H), 2.81 (m, 3H), 2.54 (m, 2H), 2.17 (m, 2H), 1.96 (m, 2H), 1.09 (d, 6H).

Example 46

1-{4-[7-(4-methanesulfonyl-phenyl)-5-methyl-5H-pyrrolo[3,2-d]pyrimidin-4-yloxy]-piperidin-1-yl}-2,2-dimethynyl-propan-1-one

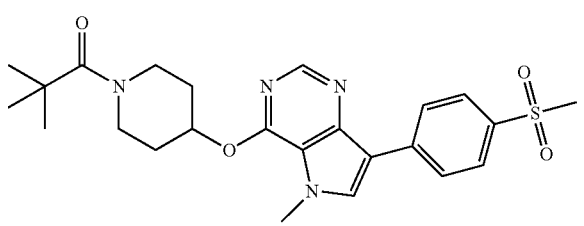 [SMILES: Cn1cc(-c2ccc(S(C)(=O)=O)cc2)c2ncnc(OC3CCN(C(=O)C(C)(C)C)CC3)c21]

The procedure of Example 27 was repeated except for using 1-(4-hydroxy-piperidin-1-yl)-2,2-dimethyl-propan-1-one instead of t-butyl 4-hydroxypiperidine-1-carboxylate to obtain the title compound.

$^1$H NMR (300 MHz, DMSO-d$_6$): δ 8.56 (s, 1H), 8.23 (d, 2H), 7.96 (d, 2H), 7.59 (s, 1H), 5.67 (m, 1H), 4.11 (s, 3H), 3.98 (m, 2H), 3.59 (m, 2H), 3.00 (s, 3H), 2.16 (m, 2H), 1.89 (m, 2H), 1.32 (d, 9H).

Example 47 tert-butyl 4-(7-(6-fluoropyridin-3-yl)-5-methyl-5H-pyrrolo[3,2-d]pyrimidin-4-yloxy)piperidine-1-carboxylate

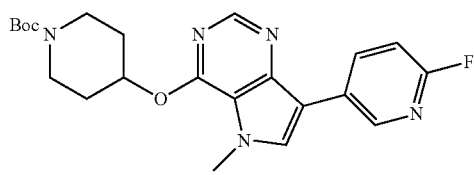 [SMILES: Cn1cc(-c2ccc(F)nc2)c2ncnc(OC3CCNCC3)c21]

The procedure of Example 25 was repeated except for using 2-fluoro-5-(4,4,5,5-tetramethyl-1,3,2-dioxaborolan-2-yl)pyridine instead of 4-methanesulfonyl-phenylboronic acid in Step 25-2 to obtain the title compound.

$^1$H NMR (300 MHz, DMSO-d$_6$): δ 8.97 (d, 1H), 8.67 (m, 1H), 8.49 (s, 1H), 8.23 (s, 1H), 7.26 (dd, 1H), 5.57 (m, 1H), 4.07 (s, 3H), 3.59 (m, 2H), 3.45 (m, 2H), 3, 1.99 (m, 2H), 1.77 (m, 2H), 1.42 (s, 9H).

Example 48

4-(1-(5-ethylpyrimidin-2-yl)piperidin-4-yloxy)-7-(6-fluoropyridin-3-yl)-5-methyl-5H-pyrrolo[3,2-d]pyrimidine

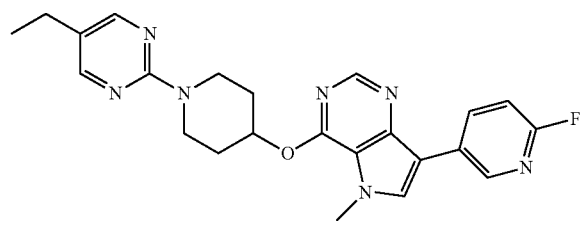 [SMILES: CCc1cnc(N2CCC(Oc3ncnc4c(-c5ccc(F)nc5)cn(C)c34)CC2)nc1]

The procedure of Example 27 was repeated except for using 2-fluoro-5-(4,4,5,5-tetramethyl-1,3,2-dioxaborolan-2-yl)pyridine instead of 4-methanesulfonyl-phenylboronic acid in Step 27-2 to obtain the title compound.

$^1$H NMR (300 MHz, DMSO-d$_6$): δ 8.97 (d, 1H), 8.67 (m, 1H), 8.49 (s, 1H), 8.23 (s, 1H), 7.26 (dd, 1H), 5.65 (m, 1H), 4.08 (s, 3H), 4.02 (m, 2H), 3.83 (m, 2H), 3.22 (s, 3H), 2.44 (dd, 2H), 2.06 (m, 2H), 1.84 (m, 2H), 1.14 (t, 3H).

Example 49

4-((1-(5-ethylpyrimidin-2-yl)piperidin-4-yl)methoxy)-5-methyl-7-(4-methanesulfonyl-phenyl)-5H-pyrrolo[3,2-d]pyrimidine

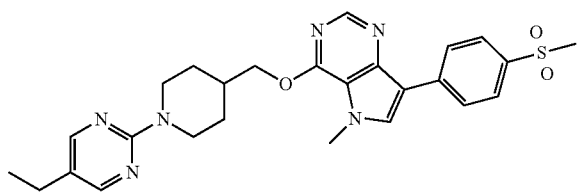

The procedure of Example 25 was repeated except for using 7-bromo-4-((1-(5-ethylpyrimidin-2-yl)piperidin-4-yl)methoxy)-5-methyl-5H-pyrrolo[3,2-d]pyrimidine instead of tert-butyl 4-(7-bromo-5-methyl-5H-pyrrolo[3,2-d]pyrimidin-4-yloxy)piperidine-1-carboxylate to obtain the title compound.

$^1$H NMR (300 MHz, DMSO-$d_6$): δ 8.53 (s, 1H), 8.44 (d, 2H), 8.39 (s, 1H), 8.24 (s, 2H), 7.95 (d, 2H), 4.69 (m, 2H), 4.43 (d, 2H), 4.04 (s, 3H), 3.21 (s, 3H), 2.90 (m, 2H), 2.43 (dd, 2H), 2.18 (m, 1H), 1.87 (m, 2H), 1.33 (m, 2H), 1.14 (t, 3H).

Hereinafter, a compound of Example 50 was prepared by the procedure shown in Reaction Scheme 12 below.

[Reaction Scheme 12]

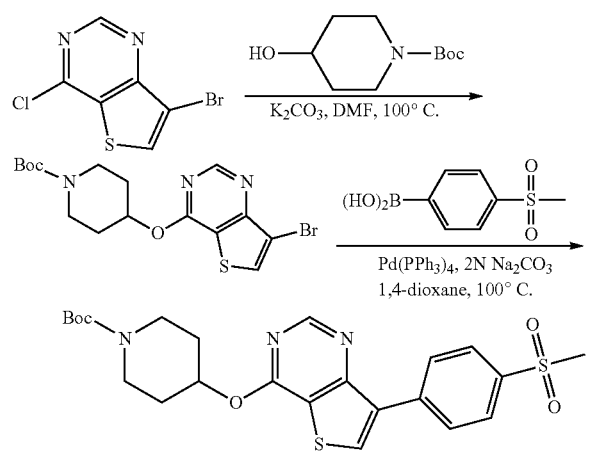

Example 50 tert-butyl 4-(7-(4-methanesulfonyl-phenyl)thieno[3,2-d]pyrimidin-4-yloxy)piperidine-1-carboxylate Step 50-1) tert-butyl 4-(7-bromothieno[3,2-d]pyrimidin-4-yloxy)piperidine-1-carboxylate

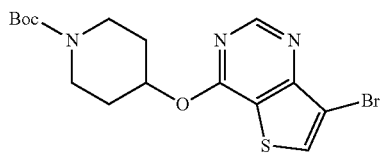 [SMILES: CC(C)(C)OC(=O)N1CCC(Oc2ncnc3c(Br)csc23)CC1]

To 7-bromo-4-chlorothieno[3,2-d]pyrimidine obtained in Step 1-3) of Preparation Example 1, t-butyl 4-hydroxypiperidine-1-carboxylate, K$_2$CO$_3$ and N,N-dimethylformamide were added, and stirred at 100° C. for 12 hours in a hermetically sealed reactor. The reaction mixture was cooled to room temperature, extracted with ethyl acetate and distilled water, and the organic layer thus obtained was washed with water and a saline solution. Subsequently, the washed organic layer was dried over anhydrous sodium sulfate, and concentrated under reduced pressure to obtain the title compound.

$^1$H NMR (300 MHz, DMSO-$d_6$): δ 8.41 (s, 1H), 7.88 (s, 1H), 5.54 (m, 1H), 3.56 (m, 2H), 3.40 (m, 2H), 1.96 (m, 2H), 1.77 (m, 2H), 1.41 (s, 9H).

Step 50-2) tert-butyl 4-(7-(4-methanesulfonyl-phenyl)thieno[3,2-d]pyrimidin-4-yloxy)piperidine-1-carboxylate

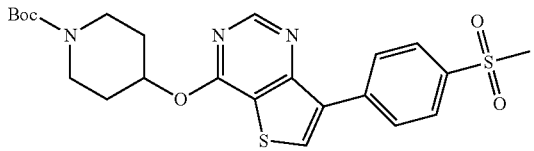 [SMILES: CC(C)(C)OC(=O)N1CCC(Oc2ncnc3c(-c4ccc(S(C)(=O)=O)cc4)csc23)CC1]

Tert-butyl 4-(7-bromothieno[3,2-d]pyrimidin-4-yloxy)piperidine-1-carboxylate (100 mg), 4-methanesulfonyl-phenylboronic acid (72 mg), Pd(PPh$_3$)$_4$ (17 mg) and 2N Na$_2$CO$_3$ (0.72 mL) were added to 1,4-dioxane (2 mL), and stirred at 100° C. for 12 hours in a hermetically sealed reactor. The reaction mixture was cooled to room temperature, extracted with ethyl acetate and distilled water, and the organic layer thus obtained was washed with water and a saline solution. Subsequently, the washed organic layer was dried over anhydrous sodium sulfate, and concentrated under reduced pressure to obtain the title compound (25 mg).

$^1$H NMR (300 MHz, DMSO-$d_6$): δ 8.89 (s, 1H), 8.83 (s, 1H), 8.38 (d, 2H), 8.05 (d, 2H), 5.56 (m, 1H), 3.70 (m, 2H), 3.26 (s, 3H), 3.29 (m, 2H), 2.06 (m, 2H), 1.73 (m, 2H), 1.42 (s, 9H).

Example 51

3-isopropyl-5-(4-(5-methyl-7-(4-methanesulfonyl-phenyl)-5H-thieno[3,2-d]pyrimidin-4-yloxy)piperidin-1-yl)-1,2,4-oxadiazole

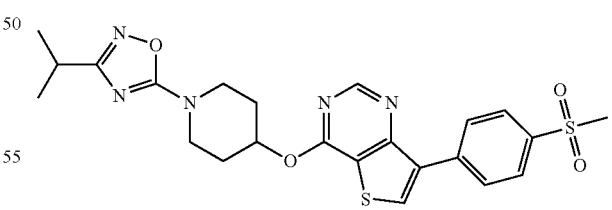

The procedure of Example 50 was repeated except for using 1-(3-isopropyl-1,2,4-oxadiazol-5-yl)piperidin-4-ol instead of 4-hydroxypiperidine-1-carboxylate to obtain the title compound.

$^1$H NMR (300 MHz, DMSO-$d_6$): δ 9.00 (s, 1H), 8.85 (s, 1H), 8.39 (d, 2H), 8.06 (d, 2H), 5.67 (m, 1H), 3.83 (m, 2H), 3.61 (m. 2H), 3.27 (s, 3H), 2.81 (m, 1H), 2.18 (m, 2H), 1.92 (m, 2H), 1.21 (d, 6H).

Example 52

3-(cyclopropylmethyl)-5-(4-(7-(4-methanesulfonyl-phenyl)thieno[3,2-d]pyrimidin-4-yloxy)piperidin-1-yl)-1,2,4-oxadiazole

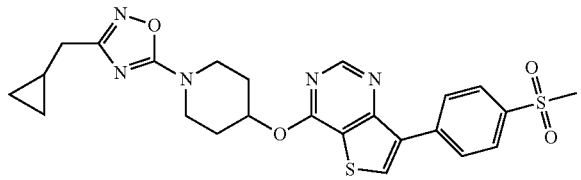 [SMILES: CS(=O)(=O)c1ccc(-c2csc3c(OC4CCN(c5nc(CC6CC6)no5)CC4)ncnc23)cc1]

The procedure of Example 50 was repeated except for using 1-(3-cyclopropylmethyl)-1,2,4-oxadiazol-5-yl)piperidin-4-ol instead of 4-hydroxypiperidine-1-carboxylate to obtain the title compound.

$^1$H NMR (300 MHz, DMSO-d$_6$): δ 8.91 (s, 1H), 8.84 (s, 1H), 8.39 (d, 2H), 8.06 (d, 2H), 5.65 (m, 1H), 3.82 (m, 2H), 3.59 (m, 2H), 3.27 (s, 3H), 2.39 (d, 2H), 2.18 (m, 2H), 1.92 (m, 2H), 1.17 (m, 1H), 0.48 (m 2H), 0.19 (m, 2H).

Example 53

3-tert-butyl-5-(4-(7-(4-methanesulfonyl-phenyl)thieno[3,2-d]pyrimidin-4-yloxy)piperidin-1-yl)-1,2,4-oxadiazole

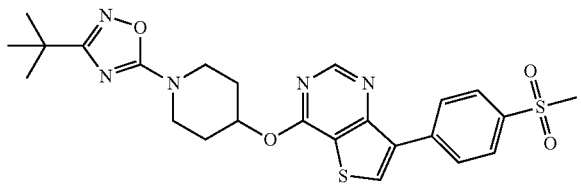 [SMILES: CC(C)(C)c1noc(N2CCC(Oc3ncnc4c(-c5ccc(S(C)(=O)=O)cc5)csc34)CC2)n1]

The procedure of Example 50 was repeated except for using 1-(3-tert-butyl-1,2,4-oxadiazol-5-yl)piperidin-4-ol instead of 4-hydroxypiperidine-1-carboxylate to obtain the title compound.

$^1$H NMR (300 MHz, DMSO-d$_6$): δ 9.10 (s, 1H), 8.94 (s, 1H), 8.39 (d, 2H), 8.06 (d, 2H), 5.66 (m, 1H), 3.85 (m, 2H), 3.58 (m, 2H), 3.27 (s, 3H), 2.20 (m, 2H), 1.91 (m, 2H), 1.25 (s, 3H).

Example 54

3-cyclobutyl-5-(4-(7-(4-methanesulfonyl-phenyl)thieno[3,2-d]pyrimidin-4-yloxy)piperidin-1-yl)-1,2,4-oxadiazole

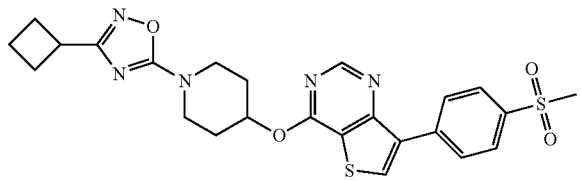 [SMILES: CS(=O)(=O)c1ccc(-c2csc3c(OC4CCN(c5nc(C6CCC6)no5)CC4)ncnc23)cc1]

The procedure of Example 50 was repeated except for using 1-(3-cyclobutyl-1,2,4-oxadiazol-5-yl)piperidin-4-ol instead of 4-hydroxypiperidine-1-carboxylate to obtain the title compound.

$^1$H NMR (300 MHz, DMSO-d$_6$): δ 8.90 (s, 1H), 8.84 (s, 1H), 8.37 (d, 2H), 8.04 (d, 2H), 5.65 (m, 1H), 3.81 (m, 2H), 3.57 (m, 2H), 3.40 (m, 1H), 3.25 (s, 3H), 2.19 (m, 6H), 1.89 (m, 4H).

Example 55

4-(1-(5-ethylpyrimidin-2-yl)piperidin-4-yloxy)-7-(4-methanesulfonyl-phenyl)thieno[3,2-d]pyrimidine

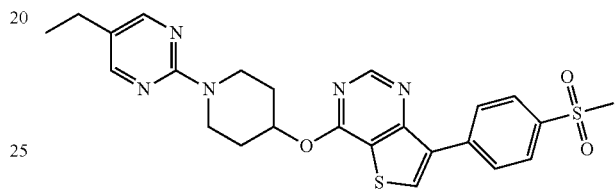

The procedure of Example 50 was repeated except for using 1-(5-ethylpyrimidin-2-yl)piperidin-4-ol instead of 4-hydroxypiperidine-1-carboxylate to obtain the title compound.

$^1$H NMR (300 MHz, DMSO-d$_6$): δ 8.90 (s, 1H), 8.82 (s, 1H), 8.37 (d, 2H), 8.26 (s, 2H), 8.04 (d, 2H), 5.66 (m, 1H), 4.20 (m, 2H), 3.57 (m, 2H), 3.26 (s, 3H), 2.48 (m, 2H), 2.11 (m, 2H), 1.77 (m, 2H), 1.13 (t, 3H).

Example 56

4-[1-(5-cyclopropyl-pyrimidin-2-yl)-piperidin-4-yloxy]-7-(4-methanesulfonyl-phenyl)-thieno[3,2-d]pyrimidine

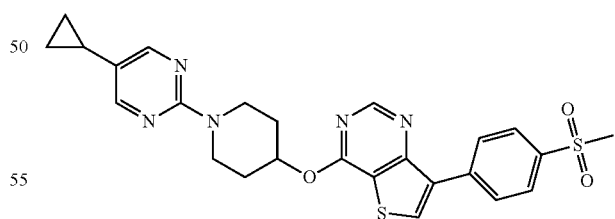

The procedure of Example 50 was repeated except for using 1-(5-cyclopropylpyrimidin-2-yl)piperidin-4-ol instead of 4-hydroxypiperidine-1-carboxylate to obtain the title compound.

$^1$H NMR (300 MHz, DMSO-d$_6$): δ 8.85 (s, 1H), 8.71 (s, 1H), 8.20 (d, 2H), 7.93 (d, 2H), 5.62 (m, 1H), 4.20 (m, 2H), 3.58 (m, 2H), 3.33 (s, 3H), 2.05 (m, 2H), 1.77 (m, 2H), 1.17 (m, 3H), 0.88 (m, 2H), 0.65 (m, 2H).

Example 57

4-[1-(5-ethylpyrimidin-2-yl)-pyrrolidin-3-yloxy]-7-(4-methanesulfonyl-phenyl)-thieno[3,2-d]pyrimidine

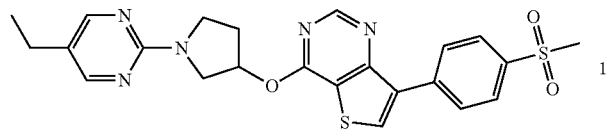

The procedure of Example 50 was repeated except for using 1-(5-ethylpyrimidin-2-yl)pyrrolidin-4-ol instead of 4-hydroxypiperidine-1-carboxylate to obtain the title compound.

$^1$H NMR (300 MHz, DMSO-d$_6$): δ 8.94 (s, 1H), 8.82 (s, 1H), 8.39 (d, 2H), 8.25 (s, 2H), 8.06 (d, 2H), 5.99 (m, 1H), 3.95-3.75 (m, 3H), 3.63 (m, 1H), 3.39 (m, 2H), 3.27 (s, 3H), 2.46 (m 2H), 1.09 (m, 3H).

Example 58

4-[1-(3-isopropyl-[1,2,4]oxadiazol-5-yl)-pyrrolidin-3-yloxy]-7-(4-methanesulfonyl-phenyl)-thieno[3,2-d]pyrimidine

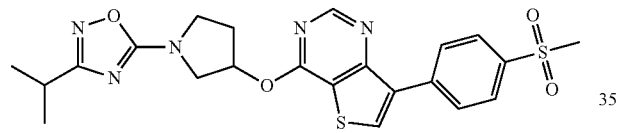

The procedure of Example 50 was repeated except for using 1-(3-isopropyl-1,2,4-oxadiazol-5-yl)pyrrolidin-4-ol instead of 4-hydroxypiperidine-1-carboxylate to obtain the title compound.

$^1$H NMR (300 MHz, DMSO-d$_6$): δ 8.94 (s, 1H), 8.85 (s, 1H), 8.40 (d, 2H), 8.07 (d, 2H), 5.99 (m, 1H), 4.02 (m, 1H), 3.83-3.67 (m, 3H), 3.27 (s, 3H), 2.87 (m, 1H), 2.45 (m, 2H), 1.11 (d, 6H).

Example 59

7-(4-((methanesulfonyl)phenyl)-4-(1-(4-(trifluoromethyl)pyrimidin-2-yl)piperidin-4-yloxy)thieno[3,2-d]pyrimidine

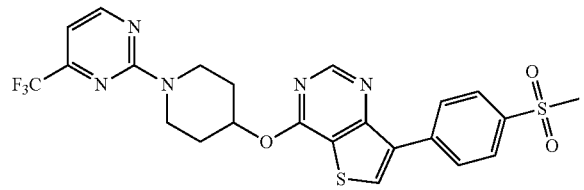 [SMILES: CS(=O)(=O)c1ccc(-c2csc3c(OC4CCN(c5nccc(C(F)(F)F)n5)CC4)ncnc23)cc1]

The procedure of Example 50 was repeated except for using 1-(4-trifluoromethyl)pyrimidin-2-yl)piperidin-4-ol instead of 4-hydroxypiperidine-1-carboxylate to obtain the title compound.

$^1$H NMR (300 MHz, DMSO-d$_6$): δ 8.92 (s, 1H), 8.84 (s, 1H), 8.71 (d, 1H), 8.39 (d, 2H), 8.06 (d, 2H), 7.04 (d, 1H), 5.71 (m, 1H), 4.24 (m, 2H), 3.69 (m, 2H), 3.27 (s, 3H), 2.20 (m, 2H), 1.85 (m, 2H).

Hereinafter, a compound of Example 60 was prepared by the procedure shown in Reaction Scheme 13 below.

[Reaction Scheme 13]

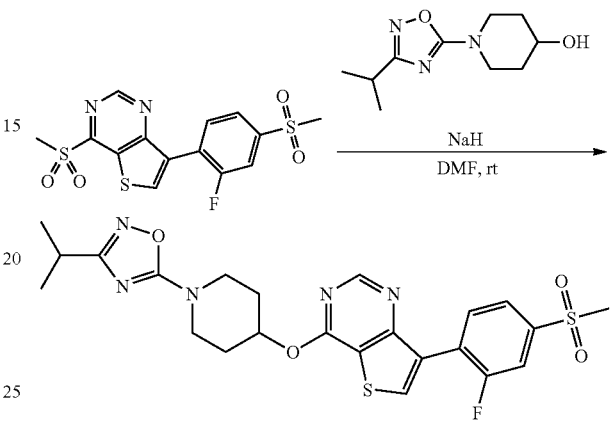

Example 60

7-(2-fluoro-4-methanesulfonyl-phenyl)-4-[1-(3-isopropyl-[1,2,4]oxadiazol-5-yl)piperidin-4-yloxy]thieno[3,2-d]pyrimidine

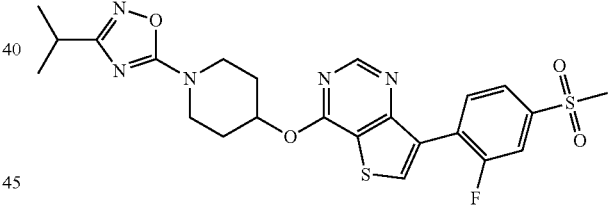

1-(3-isopropyl-1,2,4-oxadiazol-5-yl)piperidin-4-ol (30 mg) was dissolved in N,N-dimethylformamide (2 mL) and cooled to an internal temperature of 0° C. Then, NaH (9 mg) was slowly added thereto and stirred for 30 min. 7-(2-fluoro-4-methanesulfonyl-phenyl)-4-methanesulfonyl-thieno[3,2-d]pyrimidine (50 mg) synthesized in Preparation Example 2 was slowly added thereto and heated to room temperature, followed by stirring for 2 hours. Then, the reaction mixture was mixed with a saturated solution of ammonium hydroxide, and extracted twice with ethyl acetate. The organic layer thus obtained was washed with water, dried over anhydrous magnesium sulfate, and concentrated under reduced pressure to obtain a foamy residue. The residue was crystallized in the presence of diethyl ether to obtain the title compound (40 mg) as a whitish solid.

$^1$H NMR (300 MHz, DMSO-d$_6$): δ 8.71 (s, 1H), 8.50 (s, 1H), 8.25 (m, 1H), 7.92 (m, 2H), 5.64 (m, 1H), 3.84-3.80 (m, 2H), 3.60-3.54 (m, 2H), 3.33 (s, 3H), 2.82 (m, 1H), 2.25 (m, 2H), 1.97-1.89 (m, 2H), 1.77 (d, 6H).

Example 61

3-ethyl-5-(4-(7-(2-fluoro-4-methanesulfonyl-phenyl)thieno[3,2-d]pyrimidin-4-yloxy)piperidin-1-yl)-1,2,4-oxadiazole

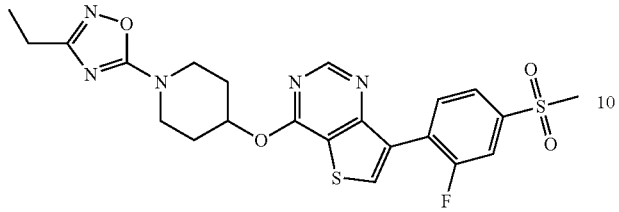

The procedure or Example 60 was repeated except for using 1-(3-ethyl-1,2,4-oxadiazol-5-yl)piperidin-4-ol instead of 1-(3-isopropyl-1,2,4-oxadiazol-5-yl)piperidin-4-ol to obtain the title compound.

$^1$H NMR (300 MHz, DMSO-d$_6$): δ 8.85 (s, 1H), 8.72 (d, 1H), 8.26 (t, 1H), 7.93 (td, 2H), 5.66-5.63 (m, 1H), 3.86-3.79 (m, 2H), 3.62-3.55 (m, 2H), 3.34 (s, 3H), 2.50 (q, 2H), 2.25-2.17 (m, 2H), 1.98-1.89 (m, 2H), 1.16 (t, 3H).

Example 62

3-sec-butyl-5-(4-(7-(2-fluoro-4-methanesulfonyl-phenyl)thieno[3,2-d]pyrimidin-4-yloxy)piperidin-1-yl)-1,2,4-oxadiazole

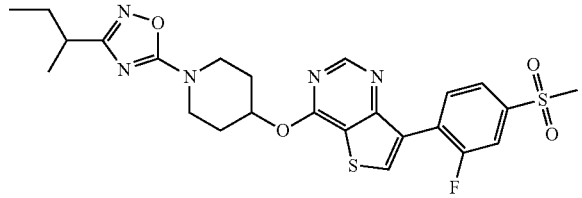 [SMILES: CCC(C)c1noc(N2CCC(Oc3ncnc4c(-c5ccc(S(C)(=O)=O)cc5F)csc34)CC2)n1]

The procedure of Example 60 was repeated except for using 1-(3-sec-butyl)-1,2,4-oxadiazol-5-yl)piperidin-4-ol instead of 1-(3-isopropyl-1,2,4-oxadiazol-5-yl)piperidin-4-ol to obtain the title compound.

$^1$H NMR (300 MHz, DMSO-d6): δ 8.85 (s, 1H), 8.72 (d, 1H), 8.26 (t, 1H), 7.93 (td, 2H), 5.66-5.63 (m, 1H), 3.86-3.81 (m, 2H), 3.61-3.55 (m, 2H), 3.34 (s, 3H), 2.62-2.60 (m, 1H), 2.25-2.17 (m, 2H), 1.94-1.90 (m, 2H), 1.64-1.52 (m, 2H), 1.17 (d, 2H), 0.84 (t, 3H).

Example 63

7-(2-fluoro-4-methanesulfonyl-phenyl)-4-[1-(3-cyclopropyl-[1,2,4]oxadiazol-5-yl)piperidin-4-yloxy]thieno[3,2]pyrimidine

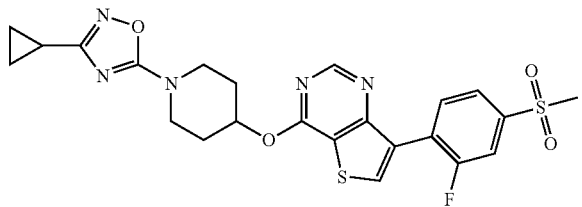 [SMILES: CS(=O)(=O)c1ccc(-c2csc3c(OC4CCN(c5nc(C6CC6)no5)CC4)ncnc23)c(F)c1]

The procedure of Example 60 was repeated except for using 1-(3-cyclopropyl-1,2,4-oxadiazol-5-yl)piperidin-4-ol instead of 1-(3-isopropyl-1,2,4-oxadiazol-5-yl)piperidin-4-ol to obtain the title compound.

$^1$H NMR (300 MHz, DMSO-d6): δ 8.85 (s, 1H), 8.72 (s, 1H), 8.26 (m, 1H), 7.93 (m, 2H), 5.64 (m, 1H), 3.84-3.80 (m, 2H), 3.60-3.54 (m, 2H), 3.33 (s, 3H), 2.25 (m, 2H), 1.97-1.89 (m, 3H) 0.95 (m, 2H), 0.83 (m, 2H).

Example 64

5-(4-(7-(2-fluoro-4-methanesulfonyl-phenyl)thieno[3,2-d]pyrimidin-4-yloxy)piperidin-1-yl)-3-phenyl-1,2,4-oxadiazole

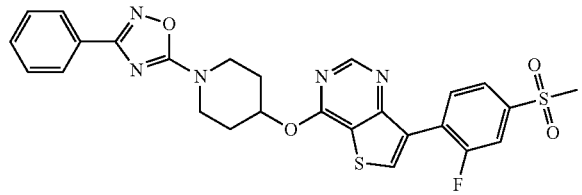 [SMILES: CS(=O)(=O)c1ccc(-c2csc3c(OC4CCN(c5nc(-c6ccccc6)no5)CC4)ncnc23)c(F)c1]

The procedure of Example 60 was repeated except for using 1-(3-phenyl-1,2,4-oxadiazol-5-yl)piperidin-4-ol instead of 1-(3-isopropyl-1,2,4-oxadiazol-5-yl)piperidin-4-ol to obtain the title compound.

$^1$H NMR (300 MHz, DMSO-d6): δ 8.86 (s, 1H), 8.72 (d; 1H), 8.27 (t, 1H), 7.97-7.90 (m, 4H), 7.53-7.49 (m, 3H), 5.73-5.65 (m, 1H), 3.96-3.91 (m, 2H), 3.73-3.70 (m, 2H), 3.34 (s, 3H), 2.26-2.22 (m, 2H), 1.98-1.93 (m, 2H).

Example 65

5-(4-(7-(2-fluoro-4-methanesulfonyl-phenyl)thieno[3,2-d]pyrimidin-4-yloxy)piperidin-1-yl)-3-(4-fluorophenyl)-1,2,4-oxadiazole

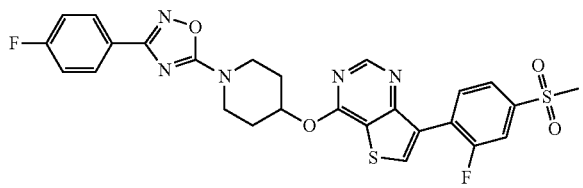 [SMILES: CS(=O)(=O)c1ccc(-c2csc3c(OC4CCN(c5nc(-c6ccc(F)cc6)no5)CC4)ncnc23)c(F)c1]

The procedure of Example 60 was repeated except for using 1-(3-(4-fluorophenyl)-1,2,4-oxadiazol-5-yl)piperidin-4-ol instead of 1-(3-isopropyl-1,2,4-oxadiazol-5-yl)piperidin-4-ol to obtain the title compound.

$^1$H NMR (300 MHz, DMSO-d6): δ 8.86 (s, 1H), 8.72 (d, 1H), 8.26 (t, 1H), 7.99-7.90 (m, 4H), 7.35 (t, 2H), 5.73-5.65 (m, 1H), 3.96-3.91 (m, 2H), 3.72-3.66 (m, 2H), 3.34 (s, 3H), 2.26-2.23 (m, 2H), 2.00-1.96 (m, 2H).

Example 66

5-(4-(7-(2-fluoro-4-methanesulfonyl-phenyl)thieno[3,2-d]pyrimidin-4-yloxy)piperidin-1-yl)-3-(pyridin-4-yl)-1,2,4-oxadiazole

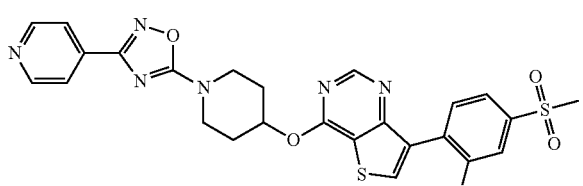

The procedure of Example 60 was repeated except for using 1-(3-(pyridin-4-yl)-1,2,4-oxadiazol-5-yl)piperidin-4-ol instead of 1-(3-isopropyl-1,2,4-oxadiazol-5-yl)piperidin-4-ol to obtain the title compound.

¹H NMR (300 MHz, DMSO-d6): δ 8.86 (s, 1H), 8.76-8.72 (m, 3H), 8.26 (t, 1H), 7.94 (t, 2H), 7.84 (d, 2H), 5.73-5.65 (m, 1H), 3.97-3.92 (m, 2H), 3.74-3.68 (m, 2H), 3.34 (s, 3H), 2.27-2.23 (m, 2H), 2.01-1.97 (m, 2H).

Example 67

5-(4-(7-(2-fluoro-4-methanesulfonyl-phenyl)thieno[3,2-d]pyrimidin-4-yloxy)piperidin-1-yl)-3-(pyridin-3-yl)-1,2,4-oxadiazole

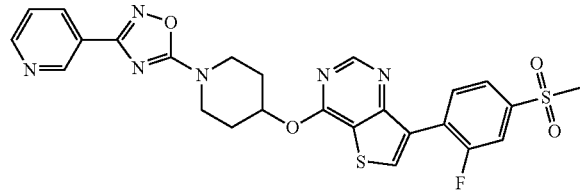 [SMILES: CS(=O)(=O)c1ccc(-c2csc3c(OC4CCN(c5nc(-c6cccnc6)no5)CC4)ncnc23)c(F)c1]

The procedure of Example 60 was repeated except for using 1-(3-(pyridin-3-yl)-1,2,4-oxadiazol-5-yl)piperidin-4-ol instead of 1-(3-isopropyl-1,2,4-oxadiazol-5-yl)piperidin-4-ol to obtain the title compound.

¹H NMR (300 MHz, DMSO-d6): δ 9.07 (s, 1H), 8.86 (s, 1H), 8.74-8.72 (m, 2H), 8.29-8.24 (m, 2H), 7.94 (t, 2H), 7.58-7.54 (m, 1H), 5.73-5.65 (m, 1H), 3.97-3.93 (m, 2H), 3.74-3.68 (m, 2H), 3.34 (s, 3H), 2.26-2.23 (m, 2H), 2.01-1.97 (m, 2H).

Example 68

5-(4-(7-(2-fluoro-4-methanesulfonyl-phenyl)thieno[3,2-d]pyrimidin-4-yloxy)piperidin-1-yl)-3-(pyrazin-2-yl)-1,2,4-oxadiazole

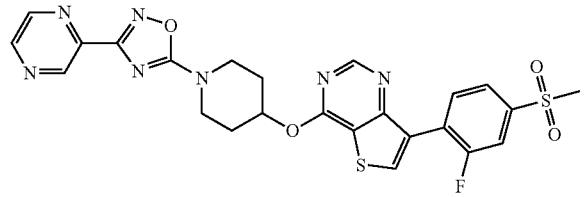 [SMILES: CS(=O)(=O)c1ccc(-c2csc3c(OC4CCN(c5nc(-c6cnccn6)no5)CC4)ncnc23)c(F)c1]

The procedure of Example 60 was repeated except for using 1-(3-(pyrazin-2-yl)-1,2,4-oxadiazol-5-yl)piperidin-4-ol instead of 1-(3-isopropyl-1,2,4-oxadiazol-5-yl)piperidin-4-ol to obtain the title compound.

¹H NMR (300 MHz, DMSO-d6): δ 9.16 (s, 1H), 8.86-8.81 (m, 3H), 8.72 (s, 1H), 8.26 (t, 1H), 7.94 (t, 2H), 5.73-5.65 (m, 1H), 3.99-3.94 (m, 2H), 3.75-3.69 (m, 2H), 3.34 (s, 3H), 2.26-2.23 (m, 2H), 2.00-1.93 (m, 2H).

Example 69

7-(2-fluoro-4-methanesulfonyl-phenyl)-4-[1-(3-cyclopropylmethyl-[1,2,4]oxadiazol-5-yl)piperidin-4-yloxy]thieno[3,2-d]pyrimidine

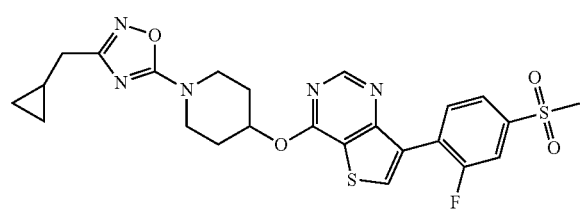 [SMILES: CS(=O)(=O)c1ccc(-c2csc3c(OC4CCN(c5nc(CC6CC6)no5)CC4)ncnc23)c(F)c1]

The procedure of Example 60 was repeated except for using 1-(3-cyclopropylmethyl-1,2,4-oxadiazol-5-yl)piperidin-4-ol instead of 1-(3-isopropyl-1,2,4-oxadiazol-5-yl)piperidin-4-ol to obtain the title compound.

¹H NMR (300 MHz, DMSO-d6): δ 8.85 (s, 1H), 8.72 (s, 1H), 8.26 (m, 1H), 7.97 (m, 2H), 5.65 (m, 1H), 3.86-3.82 (m, 2H), 3.63-3.57 (m, 2H), 3.34 (s, 3H), 2.40 (d, 2H), 2.25 (m, 2H), 1.97-1.89 (m, 2H) 1.00 (m, 1H), 0.50-0.46 (m, 2H), 0.21-0.18 (m, 2H).

Example 70

7-(2-fluoro-4-methanesulfonyl-phenyl)-4-[1-(3-cyclopentyl-[1,2,4]oxadiazol-5-yl)piperidin-4-yloxy]thieno[3,2-d]pyrimidine

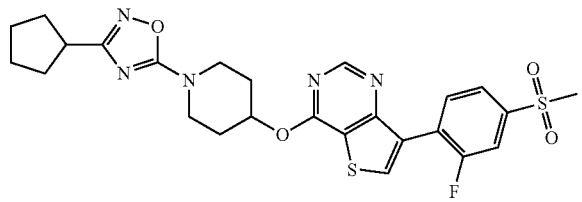 [SMILES: CS(=O)(=O)c1ccc(-c2csc3c(OC4CCN(c5nc(C6CCCC6)no5)CC4)ncnc23)c(F)c1]

The procedure of Example 60 was repeated except for using 1-(3-cyclopentyl-1,2,4-oxadiazol-5-yl)piperidin-4-ol instead of 1-(3-isopropyl-1,2,4-oxadiazol-5-yl)piperidin-4-ol to obtain the title compound.

¹H NMR (300 MHz, DMSO-d6): δ 8.85 (s, 1H), 8.73 (s, 1H), 8.27 (t, 1H), 7.94 (t, 2H), 5.66 (m, 1H), 3.90 (m, 2H), 3.59 (m, 2H), 3.29 (m, 2H), 2.40 (m, 3H), 2.30 (m, 2H), 1.95 (m, 4H), 1.71 (m, 4H).

Example 71

7-(2-fluoro-4-methanesulfonyl-phenyl)-4-[1-(3-t-butyl-[1,2,4]oxadiazol-5-yl)piperidin-4-yloxy]thieno[3,2-d]pyrimidine

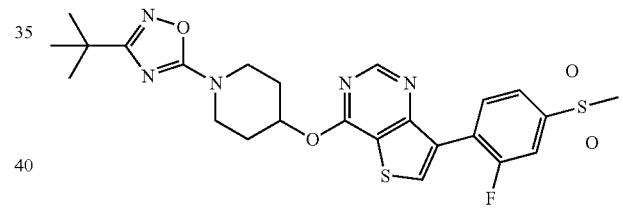

The procedure of Example 60 was repeated except for using 1-(3-t-butyl-1,2,4-oxadiazol-5-yl)piperidin-4-ol instead of 1-(3-isopropyl-1,2,4-oxadiazol-5-yl)piperidin-4-ol to obtain the title compound.

¹H NMR spectrum (300 MHz, DMSO-d₆): δ 8.98 (s, 1H), 8.72 (s, 3H), 8.27 (t, 1H), 7.94 (t, 2H), 5.64 (m, 1H), 3.84 (m, 2H), 3.57 (m, 2H), 2.27 (m, 2H), 1.92 (m, 2H), 1.31 (s, 9H).

Example 72 tert-butyl 4-(7-(2-fluoro-4-methanesulfonyl-phenyl)thieno[3,2-d]pyrimidin-4-yloxy)piperidin-1-carboxylate

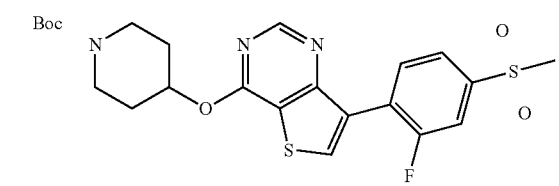

The procedure of Example 60 was repeated except for using t-butyl 4-hydroxypiperidin-1-carboxylate instead of 1-(3-isopropyl-1,2,4-oxadiazol-5-yl)piperidin-4-ol to obtain the title compound.

¹H NMR spectrum (300 MHz, DMSO-d₆): δ 8.84 (s, 1H), 8.71 (s, 1H), 8.27 (t, 1H), 7.94 (t, 2H), 5.58 (m, 1H), 3.70 (m, 2H), 3.33 (s, 3H), 2.05 (m, 2H), 1.73 (m, 2H), 1.55 (m, 2H), 1.43 (s, 9H).

Example 73 isopropyl 4-(7-(2-fluoro-4-methanesulfonyl-phenyl)thieno[3,2-d]pyrimidin-4-yloxy)piperidin-1-carboxylate

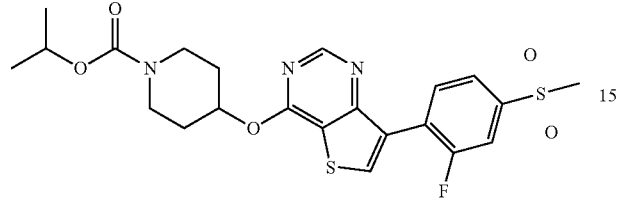

The procedure of Example 60 was repeated except for using isopropyl 4-hydroxypiperidin-1-carboxylate instead of 1-(3-isopropyl-1,2,4-oxadiazol-5-yl)piperidin-4-ol to obtain the title compound.

¹H NMR spectrum (300 MHz, DMSO-d₆): δ 8.83 (s, 1H), 8.71 (d, 1H), 8.26 (t, 1H), 7.94 (td, 2H), 5.60-5.57 (m, 1H), 4.81-4.77 (m, 1H), 3.76-3.71 (m, 2H), 3.47-3.41 (m, 2H), 3.34 (s, 3H), 2.08-2.04 (m, 2H), 1.78-1.72 (m, 2H), 1.20 (d, 6H).

Example 74

7-(2-fluoro-4-methanesulfonyl-phenyl)-4-[1-methylpiperidin-4-yloxy]thieno[3,2-d]pyrimidine

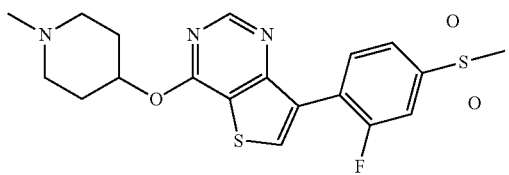

The procedure of Example 60 was repeated except for using 1-methylpiperidin-4-ol instead of 1-(3-isopropyl-1,2,4-oxadiazol-5-yl)piperidin-4-ol to obtain the title compound.

¹H NMR spectrum (300 MHz, DMSO-d₆): δ 8.82 (s, 1H), 8.70 (s, 1H), 8.27 (t, 1H), 7.95 (t, 2H), 5.39 (m, 1H), 3.72 (m, 2H), 3.37 (s, 3H), 2.62 (m, 2H), 2.25-2.09 (m, 3H), 2.05 (m, 2H), 1.73 (m, 2H).

Example 75

4-(7-(2-fluoro-4-methanesulfonyl-phenyl)thieno[3,2-d]pyrimidin-4-yloxy)piperidin-1-carbonitrile

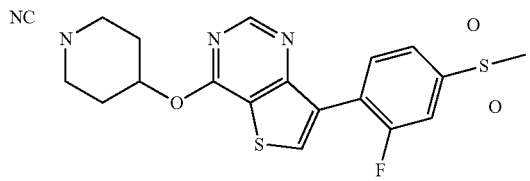

The procedure of Example 60 was repeated except for using 4-hydroxypiperidin-1-carbonitrile instead of 1-(3-isopropyl-1,2,4-oxadiazol-5-yl)piperidin-4-ol to obtain the title compound.

¹H NMR spectrum (300 MHz, DMSO-d₆): δ 8.82 (s, 1H), 8.71 (s, 1H), 8.26 (t, 1H), 7.92 (t, 2H), 5.54 (m, 1H), 3.42 (m, 2H), 3.33 (s, 3H), 3.30 (m, 2H), 2.13 (m, 2H), 1.90 (m, 2H).

Example 76

7-(2-fluoro-4-methanesulfonyl-phenyl)-4-[piperidin-4-yloxy]thieno[3,2-d]pyrimidine

The procedure of step 5-3 in Preparation Example 5 was repeated using the compound obtained in Example 75 to obtain the title compound.

¹H NMR spectrum (300 MHz, DMSO-d₆): δ 8.82 (s. 1H), 8.70 (s, 1H), 8.27 (t, 1H), 7.94 (s, 2H), 5.46 (s, 1H), 3.34 (s, 3H), 2.99 (m, 2H), 2.64 (m, 2H), 2.04 (m, 2H), 1.66 (m, 2H).

Example 77

2-(4-(7-(2-fluoro-4-methanesulfonyl-phenyl)thieno[3,2-d]pyrimidin-4-yloxy)piperidin-1-yl)benzo[d]oxazole

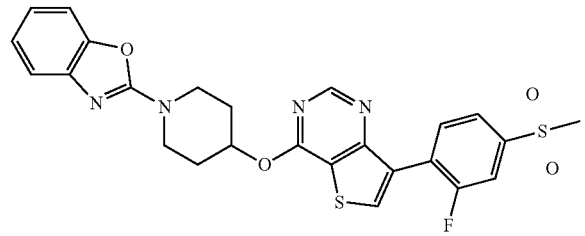

The procedure of Example 60 was repeated except for using 1-(benzo[d]oxazol-2-yl)piperidin-4-ol instead of 1-(3-isopropyl-1,2,4-oxadiazol-5-yl)piperidin-4-ol to obtain the title compound.

¹H NMR spectrum (300 MHz, DMSO-d₆): δ 8.89 (s. 1H), 8.73 (s, 1H), 8.27 (t, 1H), 7.99 (m, 2H), 7.50 (d, 1H), 7.42 (d, 1H), 7.33 (t, 1H), 7.00 (t, 1H), 5.66 (s, 1H), 3.99 (m, 2H), 3.51 (m, 2H), 3.33 (s, 3H), 2.23 (m, 2H), 2.05-1.98 (m, 2H).

Example 78

7-(2-fluoro-4-methanesulfonyl-phenyl)-4-[1-(3-isobutyl-[1,2,4]oxadiazol-5-yl)piperidin-4-yloxy]thieno[3,2-d]pyrimidine

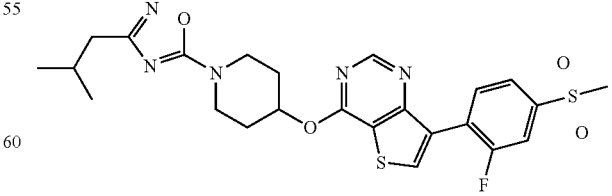

The procedure of Example 60 was repeated except for using 1-(3-isobutyl-1,2,4-oxadiazol-5-yl)piperidin-4-ol instead of 1-(3-isopropyl-1,2,4-oxadiazol-5-yl)piperidin-4-ol to obtain the title compound.

¹H NMR spectrum (300 MHz, DMSO-d₆): δ 8.83 (s, 1H), 8.70 (s, 1H), 8.25 (m, 1H), 7.95 (m, 2H), 5.63 (m, 1H), 3.84-3.80 (m, 2H), 3.60-3.53 (m, 2H), 3.32 (s, 3H), 2.32 (d, 2H), 2.15 (m, 2H), 1.97-1.88 (m, 3H), 0.90 (d, 6H).

Example 79

7-(2-fluoro-4-methanesulfonyl-phenyl)-4-[1-(3-cyclohexyl-[1,2,4]oxadiazol-5-yl)piperidin-4-yloxy]thieno[3,2-d]pyrimidine

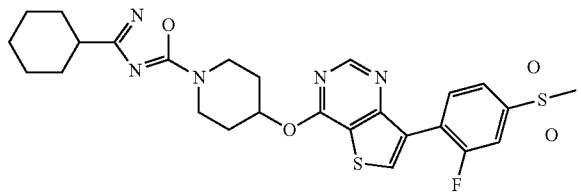

The procedure of Example 60 was repeated except for using 1-(3-cyclohexyl-1,2,4-oxadiazol-5-yl)piperidin-4-ol instead of 1-(3-isopropyl-1,2,4-oxadiazol-5-yl)piperidin-4-ol to obtain the title compound.

¹H NMR spectrum (300 MHz, DMSO-d₆): δ 8.85 (s, 1H), 8.70 (s, 1H), 8.25 (m, 1H), 7.95 (m, 2H), 5.63 (m, 1H), 3.84-3.80 (m, 2H), 3.60-3.53 (m, 2H), 3.32 (s, 3H), 2.32 (d, 2H), 2.35-2.10 (m 4H), 2.15 (m, 2H), 1.97-1.88 (m, 4H), 1.11-1.00 (m, 2H).

Example 80

7-(2-fluoro-4-methanesulfonyl-phenyl)-4-[1-(3-bicyclo[2,2,1]heptan-2-yl[1,2,4]oxadiazol-5-yl)piperidin-4-yloxy]thieno[3,2-d]pyrimidine

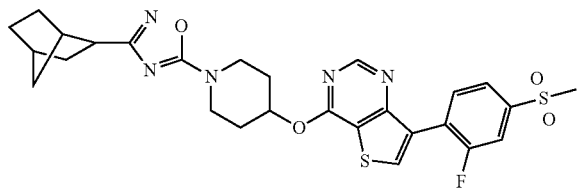

The procedure of Example 60 was repeated except for using 1-(3-bicycloheptan-2-yl)-1,2,4-oxadiazol-5-yl)piperidin-4-ol instead of 1-(3-isopropyl-1,2,4-oxadiazol-5-yl)piperidin-4-ol to obtain the title compound.

¹H NMR spectrum (300 MHz, DMSO-d₆): δ 8.85 (s, 1H), 8.70 (s, 1H), 8.25 (m, 1H), 7.95 (m, 2H), 5.63 (m, 1H), 3.84-3.80 (m, 2H), 3.60-3.53 (m, 2H), 3.32 (s, 3H), 2.32 (d, 2H), 2.15 (m, 2H), 1.45-1.11 (m, 11H).

Example 81

4-[1-(5-ethylpyrimidin-2-yl)-piperidin-4-yloxy]-7-(2-fluoro-4-methanesulfonyl-phenyl)-thieno[3,2-d]pyrimidine

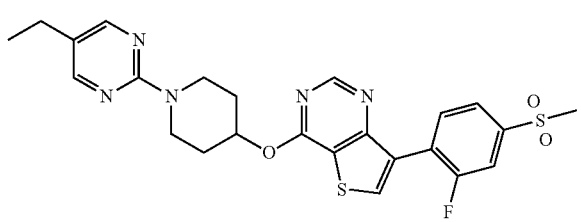

The procedure of Example 60 was repeated except for using 1-(5-ethylpyrimidin-2-yl)piperidin-4-ol instead of 1-(3-isopropyl-1,2,4-oxadiazol-5-yl)piperidin-4-ol to obtain the title compound.

¹H NMR spectrum (300 MHz, DMSO-d₆): δ 8.89 (s, 1H), 8.81 (s, 1H), 8.37 (m, 1H), 8.24 (s, 2H), 7.99 (m, 2H), 5.65 (m, 1H), 4.23-4.19 (m, 2H), 3.60-3.53 (m, 2H), 3.33 (s, 3H), 3.01 (m, 2H), 2.15 (m, 2H), 1.87 (m, 2H), 1.45-1.11 (t, 3H).

Example 82

7-(2-fluoro-4-4-[1-(5-trifluoromethylpyrimidin-2-yl)-piperidin-4-yloxy]-thieno[3,2-d]pyrimidine

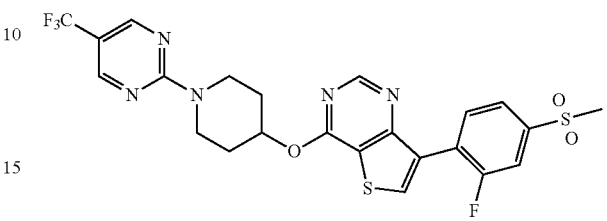

The procedure of Example 60 was repeated except for using 1-(5-trifluoromethyl)pyrimidin-2-yl)piperidin-4-ol instead of 1-(3-isopropyl-1,2,4-oxadiazol-5-yl)piperidin-4-ol to obtain the title compound.

¹H NMR spectrum (300 MHz, DMSO-d₆): δ 8.89 (s, 1H), 8.81 (s, 1H), 8.37 (m, 1H), 8.24 (s, 2H), 7.99 (m, 2H), 5.65 (m, 1H), 4.23-4.19 (m, 2H), 3.60-3.53 (m, 2H), 3.33 (s, 3H), 3.01 (m, 2H), 2.15 (m, 2H).

Example 83

7-(2-fluoro-4-methanesulfonyl-phenyl)-4-[1-(5-propyl-pyrimidin-2-yl)-piperidin-4-yloxy]-thieno[3,2-d]pyrimidine

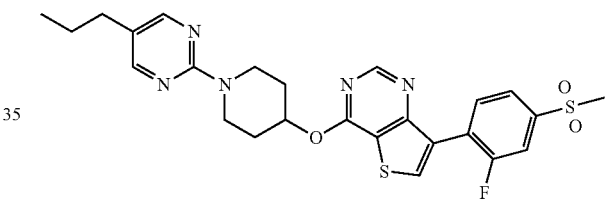

The procedure of Example 60 was repeated except for using 1-(5-propylpyrimidin-2-yl)piperidin-4-ol instead of 1-(3-isopropyl-1,2,4-oxadiazol-5-yl)piperidin-4-ol to obtain the title compound.

¹H NMR spectrum (300 MHz, DMSO-d₆): δ 8.89 (s, 1H), 8.81 (s, 1H), 8.37 (m, 1H), 8.24 (s, 2H), 7.99 (m, 2H), 5.65 (m, 1H), 4.23-4.19 (m, 2H), 3.60-3.53 (m, 2H), 3.34 (s, 3H), 3.01 (m, 2H), 2.15 (m, 2H), 1.99-1.90 (m 2H), 1.88 (m, 2H), 1.45-1.11 (t, 3H).

Example 84

7-(2-fluoro-4-methanesulfonyl-phenyl)-4-[1-(5-cyclopropyl-pyrimidin-2-yl)-piperidin-4-yloxy]-thieno[3,2-d]pyrimidine

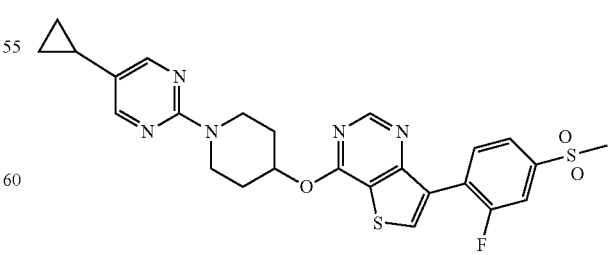

The procedure of Example 60 was repeated except for using 1-(5-cyclopropylpyrimidin-2-yl)piperidin-4-ol instead of 1-(3-isopropyl-1,2,4-oxadiazol-5-yl)piperidin-4-ol to obtain the title compound.

¹H NMR spectrum (300 MHz, DMSO-d₆): δ 8.85 (s, 1H), 8.81 (s, 1H), 8.34 (m, 1H), 8.24 (s, 2H), 7.98 (m, 2H), 5.64 (m, 1H), 4.23-4.19 (m, 2H), 3.60-3.53 (m, 2H), 3.33 (s, 3H), 3.01 (m, 2H), 1.99-1.90 (m 2H), 1.56 (m, 1H), 1.33-1.11 (m, 2H), 0.99-0.87 (m, 2H).

Example 85

7-(2-fluoro-4-methanesulfonyl-phenyl)-4-(1-pyrimidin-2-yl-piperidin-4-yloxy)-thieno[3,2-d]pyrimidine

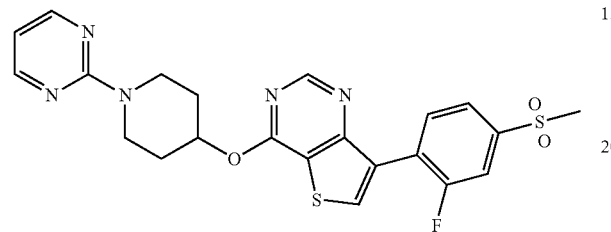

The procedure of Example 60 was repeated except for using 1-(pyrimidin-2-yl)piperidin-4-ol instead of 1-(3-isopropyl-1,2,4-oxadiazol-5-yl)piperidin-4-ol to obtain the title compound.

¹H NMR spectrum (300 MHz, DMSO-d₆): δ 8.86 (s, 1H), 8.71 (s, 1H), 8.38 (d, 2H), 8.27 (t, 2H), 7.91 (t, 1H), 6.65 (t, 1H), 5.70 (m, 1H), 4.20 (m, 2H), 3.64 (m, 2H), 3.35 (s, 3H), 2.14 (m, 2H), 1.80 (m, 2H).

Example 86

7-(2-fluoro-4-methanesulfonyl-phenyl)-4-{1-[5-(4-isopropylphenyl)-pyrimidin-2-yl)-piperidin-4-yloxy]-thieno[3,2-d]pyrimidine

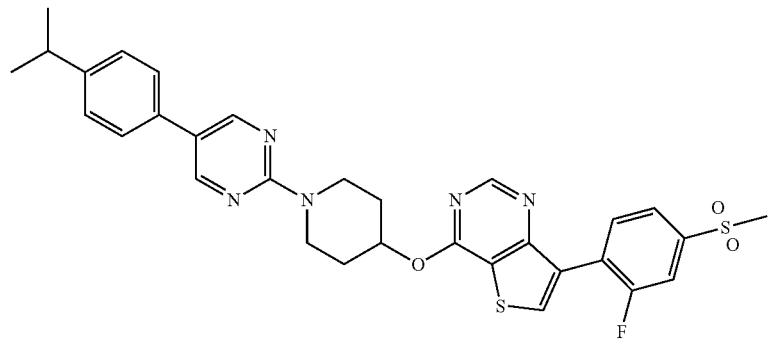

The procedure of Example 60 was repeated except for using 1-(5-(4-isopropylphenyl)pyrimidin-2-yl)piperidin-4-ol instead of 1-(3-isopropyl-1,2,4-oxadiazol-5-yl)piperidin-4-ol to obtain the title compound.

¹H NMR spectrum (300 MHz, DMSO-d₆): δ 8.87 (s, 1H), 8.71 (s, 3H), 8.20 (t, 1H), 7.94 (t, 2H), 7.57 (d, 2H), 7.23 (d, 2H), 5.76 (m, 1H), 4.30 (m, 2H), 3.70 (m, 3H), 2.90 (m, 2H), 2.10 (m, 2H), 1.80 (m, 3H), 1.24 (d, 6H).

The compound of Example 87 was prepared by the procedure shown in Reaction Scheme 14.

<Reaction Scheme 14>

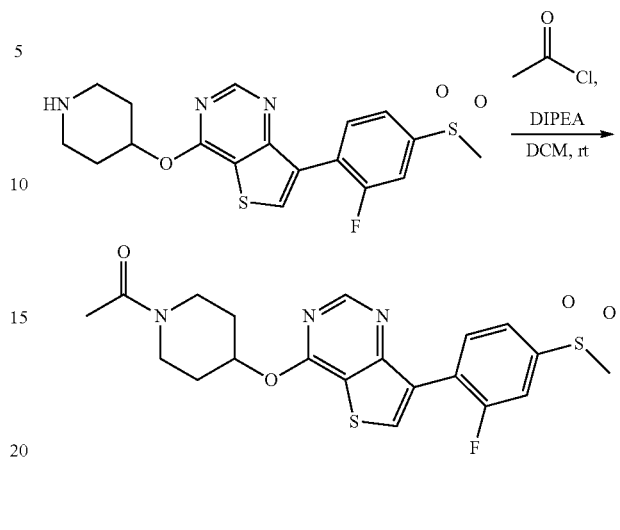

Example 87

1-(4-(7-(2-fluoro-4-methanesulfonyl-phenyl)thieno[3,2-d]pyrimidin-4-yloxy)piperidin-1-yl)ethanone

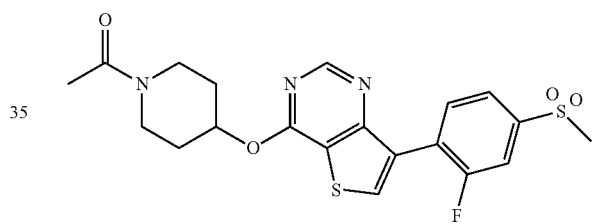

30 mg (0.0736 mmol) of 7-(2-fluoro-4-methanesulfonyl-phenyl)-4-(piperidin-4-yloxy)thieno[3,2-d]pyrimidine was dissolved in 1 ml of dimethylchloride, and 20 (0.147 mmol) of acetyl chloride and 19 µl (0.110 mmol) of diisopropylethylamine were added thereto. The mixture was stirred at room temperature for 13 hr. The resulting mixture was dissolved in ethylacetate and washed with sodium bicarbonate. The organic layer was dried over anhydrous magnesium sulfate, and concentrated under a reduced pressure to obtain 17 mg of the title compound as a pale yellow solid.

¹H NMR spectrum (300 MHz, DMSO-d₆): δ 8.84 (s, 1H), 8.71 (d, 1H), 8.26 (t, 1H), 7.94 (td, 2H), 5.64-5.59 (m, 1H), 3.90-3.86 (m, 1H), 3.72-3.70 (m, 1H), 3.46-3.43 (m, 2H), 3.34 (s, 3H), 2.26-2.22 (m, 2H), 2.04 (s, 3H), 1.83-1.80 (m, 1H), 1.71-1.67 (m, 1H).

Example 88

1-(4-(7-(2-fluoro-4-methanesulfonyl-phenyl)thieno[3,2-d]pyrimidin-4-yloxy)piperidin-1-yl)-2,2-dimethylpropan-1-one

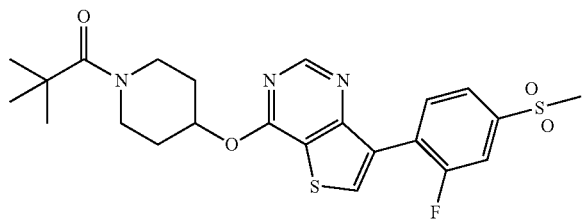

The procedure of Example 87 was repeated except for using pivaloyl chloride instead of acetyl chloride to obtain the title compound.

¹H NMR spectrum (300 MHz, DMSO-d₆): δ 8.84 (s, 1H), 8.71 (d, 1H), 8.26 (t, 1H), 7.94 (td, 2H), 5.64-5.59 (m, 1H), 3.97-3.93 (m, 2H), 3.47-3.41 (m, 2H), 3.34 (s, 3H), 2.08-1.98 (m, 2H), 1.77-1.72 (m, 2H), 1.22 (s, 9H).

Example 89

{4-[7-(2-fluoro-4-methanesulfonyl-phenyl)-thieno[3,2-d]pyrimidin-4-yloxy]-piperidin-1-yl}phenyl-methanone

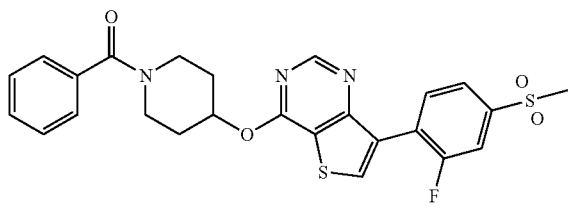

The procedure of Example 87 was repeated except for using benzoyl chloride instead of acetyl chloride to obtain the title compound.

¹H NMR spectrum (300 MHz, DMSO-d₆): δ 8.87 (s, 1H), 8.75 (s, 1H), 8.25 (t, 1H), 7.97 (t, 2H), 7.33 (m, 2H), 6.79 (m, 3H), 5.68 (m, 1H), 3.89 (m, 2H), 3.43 (m, 2H), 3.33 (s, 3H), 2.11 (m, 2H), 1.82 (m, 2H).

Example 90

{4-[7-2-fluoro-4-methanesulfonyl-phenyl]-thieno[3,2-d]pyrimidin-4-yloxy]-piperidin-1-yl}pyridin-3-yl-methanone

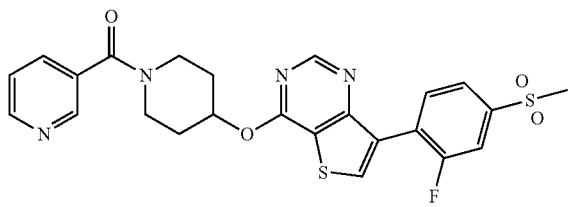

The procedure of Example 87 was repeated except for using nicotinoyl chloride instead of acetyl chloride to obtain the title compound.

¹H NMR spectrum (300 MHz, DMSO-d₆): δ 8.82 (s, 1H), 8.70 (s, 1H), 8.65 (m, 2H), 8.24 (t, 1H), 7.92 (m, 3H), 7.47 (t, 1H), 5.66 (m, 1H), 3.55 (m, 2H), 3.33 (s, 3H), 2.14 (m, 2H), 1.87 (m, 2H), 1.48 (m, 2H).

The compound of Example 91 was prepared by the procedure shown in Reaction Scheme 15.

[Reaction Scheme 15]

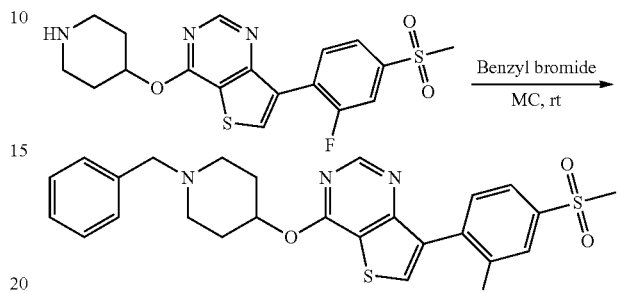

Example 91

4-(1-benzylpiperidin-4-yloxy]-7-(2-fluoro-4-methanesulfonyl-phenyl)thieno[3,2-d]pyrimidine

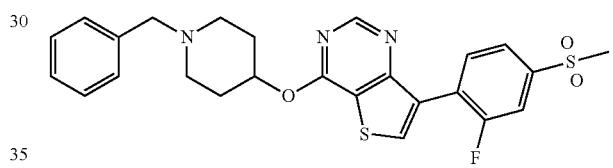

50 mg of 7-(2-fluoro-4-methanesulfonyl-phenyl)-4-[piperidin-4-yloxy]thieno[3,2-d]pyrimidin was added to 1 ml of dichloromethane, and 32 μl of triethylamine was added thereto. 16 μl of (bromomethyl)benzene was added to the mixture, and after 1 hr, water was added thereto for terminating the reaction. The resulting solution was extracted with dichloromethane, dried over anhydrous sodium sulfate, and concentrated under a reduced pressure to obtain a bubble residue. The resulting residue was purified by column chromatography to obtain 30 mg of the title compound.

¹H NMR spectrum (300 MHz, DMSO-d₆): δ 8.81 (s, 1H), 8.70 (s, 1H), 8.26 (t, 1H), 7.93 (t, 2H), 7.32 (m, 4H), 7.25 (m, 1H), 5.42 (m, 1H), 3.52 (s, 2H), 3.33 (s, 3H), 2.72 (m, 2H), 2.33 (m, 2H), 2.10 (m, 2H), 1.81 (m, 2H).

Example 92

4-(4-bromo-1-benzyl-piperidin-4-yloxy]-7-(2-fluoro-4-methanesulfonyl-phenyl)thieno[3,2-d]pyrimidine The procedure of Example 91 was repeated except for using 1-bromo-4-(bromomethyl)benzene instead of (bromomethyl)benzene to obtain the title compound.

¹H NMR spectrum (300 MHz, DMSO-d₆): δ 8.82 (s, 1H), 8.71 (s, 1H), 8.29-8.20 (m, 3H), 7.93 (t, 2H), 7.65 (d, 2H), 5.44 (m, 1H), 3.67 (s, 2H), 3.34 (s, 3H0, 2.72 (m, 2H), 2.41 (m, 2H), 2.08 (m, 2H), 1.85 (m, 2H).

The compound of Example 93 was prepared by the procedure shown in Reaction Scheme 16.

[Reaction Scheme 16]

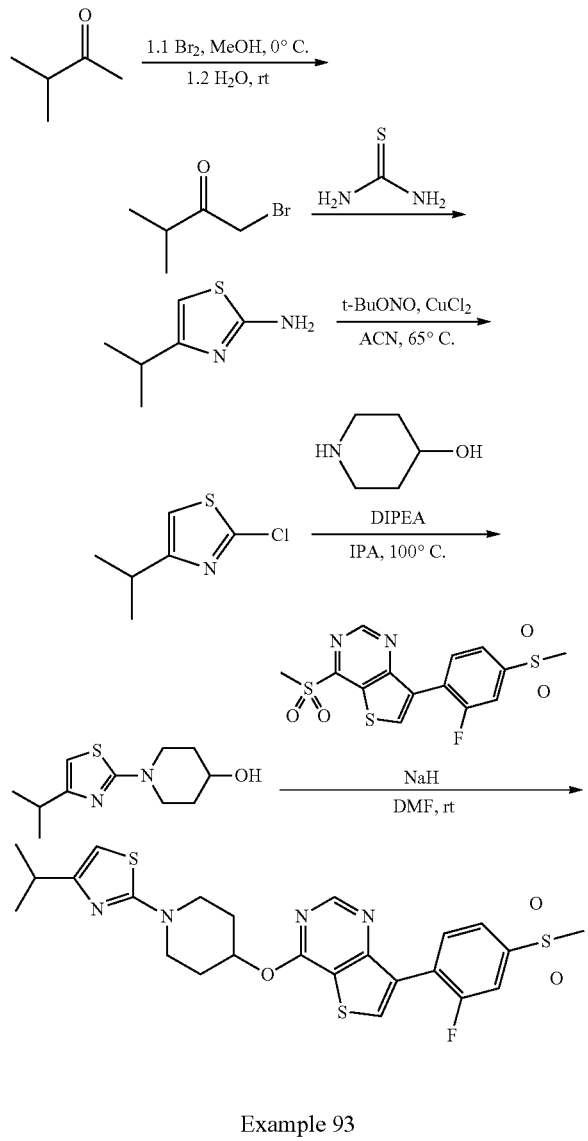

Example 93

7-(2-fluoro-4-methanesulfonyl-phenyl)-4-[1-(4-isopropyl-thiazo-2-yl)piperidin-4-yloxy]-thieno[3,2-d]pyrimidine Step 93-1) 1-bromo-3-methyl-butan-2-one

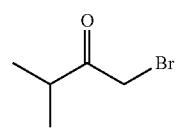

6 g of isopropyl methyl ketone was added in 20 ml of methanol and cooled to 0° C. 3.56 ml of brome was dropwise added to the mixture to adjust a temperature thereof not to exceed 10° C. and stirred for 45 min. 20 ml of water was added to the resulting mixture and stirred for 20 hr at room temperature. The reaction was terminated by adding water, and the resulting mixture was extracted twice with ethyl acetate. The organic layer was washed with sodium bicarbonate and water, dried over anhydrous sodium sulfate, and concentrated under a reduced pressure to obtain 5 g of the title compound in the colorless and transparent oil form.

¹H NMR spectrum (300 MHz, DMSO-d₆): δ 3.99 (s, 2H), 2.99 (m, 1H), 1.16 (d, 6H).

Step 93-2) 4-isopropyl-thiazol-2-yl amine

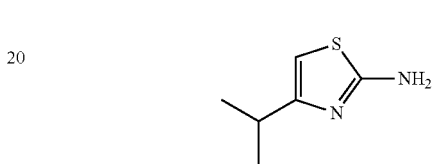

2 g of 1-bromo-3-methyl-butan-2-one obtained in step 93-1 was added to 20 ml of ethanol and 920 mg of thiourea was added thereto. The mixture was heated to 60° C., stirred for 3.5 hr and cooled to room temperature. The resulting mixture was added with aqueous sodium carbonate and extracted twice with ethyl acetate. The organic layer was washed with water and saline solution, dried over anhydrous magnesium sulfate and concentrated under a reduced pressure. The resulting residue thus obtained was purified by column chromatography (ethyl acetate/hexane=1/2) to obtain 1.2 g of the title compound.

¹H NMR spectrum (300 MHz, DMSO-d₆): δ 6.79 (s, 2H), 6.05 (s, 1H), 2.65 (m, 1H), 1.15 (d, 6H).

Step 93-3) 2-chloro-4-isopropyl-thiazole

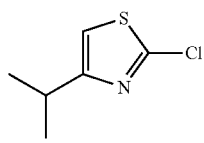

500 mg of 4-isopropyl-thiazol-2-yl amine obtained in step 93-2 was dissolved in 10 ml of acetonitrile and 900 mg of cupper(II) chloride dehydrate was added to the mixture, followed by adding 630 μl of t-BuNO₂ thereto dropwise. The resulting mixture was heated to 65° C. and stirred for 2 hr. The resulting solution was cooled to room temperature and the reaction was terminated by adding water. The resulting mixture was extracted twice with ethyl acetate and washed with water and saline solution. The organic layer was dried over anhydrous magnesium sulfate and concentrated under a reduced pressure to obtain 500 mg of the title compound as a light brown oil.

¹H NMR spectrum (300 MHz, DMSO-d₆): δ 7.29 (s, 1H), 2.96 (m, 1H), 1.21 (d, 6H).

Step 93-4) 1-(4-isopropyl-thiazo-2-yl)-piperidin-4-ol

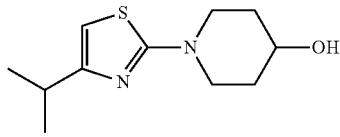

2-chloro-4-isopropyl-thiazole obtained in step 93-3 was reacted with 4-hydroxypiperidine in a same condition disclosed in the procedure of intermediate 10 to obtain the title compound.

¹H NMR spectrum (300 MHz, DMSO-d₆): δ 7.25 (s, 1H), 3.00-3.05 (m, 2H), 2.99-2.90 (m, 2H), 1.74-1.72 (m, 3H), 1.41-1.39 (m, 2H), 1.18 (d, 6H).

Step 93-5) 7-(2-fluoro-4-methanesulfonyl-phenyl)-4-[1-(4-isopropyl-thiazo-2-yl)piperidin-4-yloxy]-thieno[3,2-d]pyrimidine

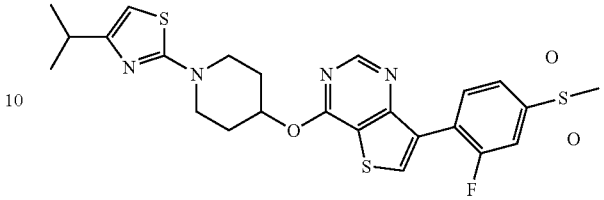

The procedure of Example 60 was repeated except for using 1-(4-isopropyl-thiazo-2-yl)-piperidin-4-ol obtained in step 93-4 instead of 1-(3-isopropyl-1,2,4-oxadiazol-5-yl)piperidin-4-ol to obtain the title compound.

¹H NMR spectrum (300 MHz, DMSO-d₆): δ 8.72 (s, 1H), 8.50 (s, 1H), 8.25 (m, 1H), 8.00 (s, 1H), 7.92 (m, 2H), 5.64 (m, 1H), 3.84-3.80 (m, 2H), 3.60-3.54 (m, 2H), 3.33 (s, 3H), 2.82 (m, 1H), 2.25 (m, 2H), 1.97-1.89 (m, 2H), 1.77 (d, 6H).

The compound of Example 94 was prepared by the procedure shown in Reaction Scheme 17.

[Reaction Scheme 17]

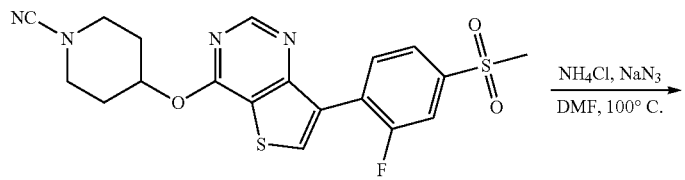

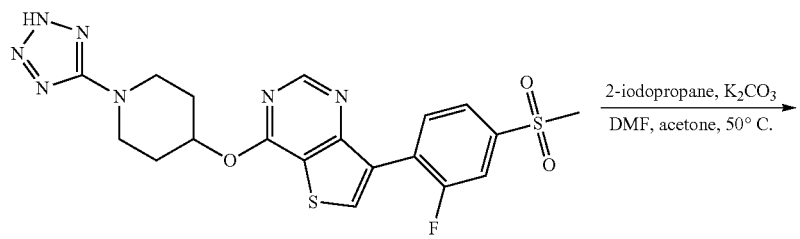

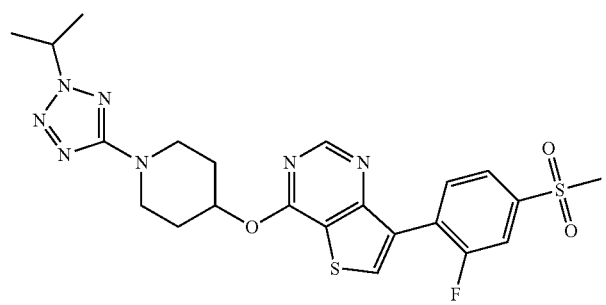

Example 94

7-(2-fluoro-4-methanesulfonyl-phenyl)-4-(1-(2-isopropyl-2H-tetrazol-5-yl)piperidin-4-yloxy)thieno[3,2-d]pyrimidine

Step 94-1) 4-(1-(2H-tetrazol-5-yl)piperidin-4-yloxy)-7-(2-fluoro-4-methanesulfonyl-phenyl)thieno[3,2-d]pyrimidine

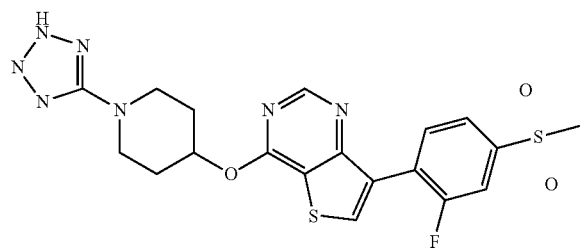

2.5 ml of dimethylformamide was added to 200 mg 4-(7-(2-fluoro-4-methanesulfonyl-phenyl)thieno[3,2-d]pyrimidin-4-yloxy)piperidin-1-carbonitrile of Example 75, and 33 mg of NH₄Cl and 45 mg of NaN₃ 45 mg were added thereto with stirring. The mixture was stirred at 100° C. for 12 hr. The resulting mixture was cooled to room temperature, added with water and stirred. The solid thus obtained was filtered to obtain 120 mg of the title compound.

$^1$H NMR spectrum (300 MHz, DMSO-$d_6$): δ 8.84 (s, 1H), 8.70 (d, 1H), 8.25 (t, 1H), 7.93 (td, 2H), 5.66-5.63 (m, 1H), 3.77-3.72 (m, 2H), 3.47-3.41 (m, 2H), 3.34 (s, 3H), 2.27-2.17 (m, 2H), 1.92-1.88 (m, 2H).

Step 94-2) 7-(2-fluoro-4-methanesulfonyl-phenyl)-4-(1-(2-isopropyl-2H-tetrazol-5-yl)piperidin-4-yloxy)thieno[3,2-d]pyrimidine

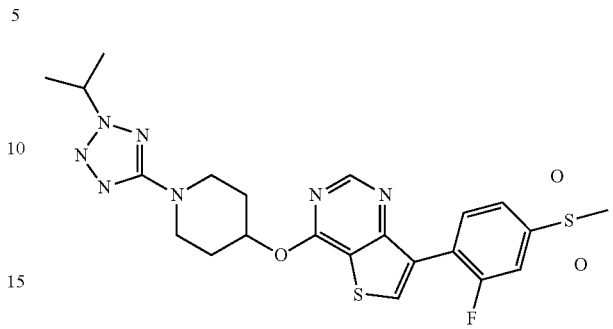

700 mg of 4-(1-(2H-tetrazol-5-yl)piperidin-4-yloxy)-7-(2-fluoro-4-methanesulfonyl-phenyl)thieno[3,2-d]pyrimidine obtained in step 94-1 and 41 mf of K₂CO₃ were added in a mixture of methylformamide and acetone, and 44 μl of 2-iodopropane was dropwise added with stirring. The resulting mixture was stirred at 50° C. for 12 hr, cooled to room temperature and extracted three times with ethyl acetate. The organic layer was dried over anhydrous sodium sulfate, filtered and concentrated under a reduced pressure to obtain 51 mg of the title compound.

$^1$H NMR spectrum (300 MHz, DMSO-$d_6$): δ 8.85 (s, 1H), 8.72 (d, 1H), 8.26 (t, 1H), 7.93 (td, 2H), 5.66-5.63 (m, 1H), 4.93-4.88 (m, 1H), 3.80-3.76 (m, 2H), 3.42-3.37 (m, 2H), 3.34 (s, 3H), 2.22-2.16 (m, 2H), 1.98-1.89 (m, 2H), 1.51 (d, 6H).

The compound of Example 95 was prepared by the procedure shown in Reaction Scheme 18.

[Reaction Scheme 18]

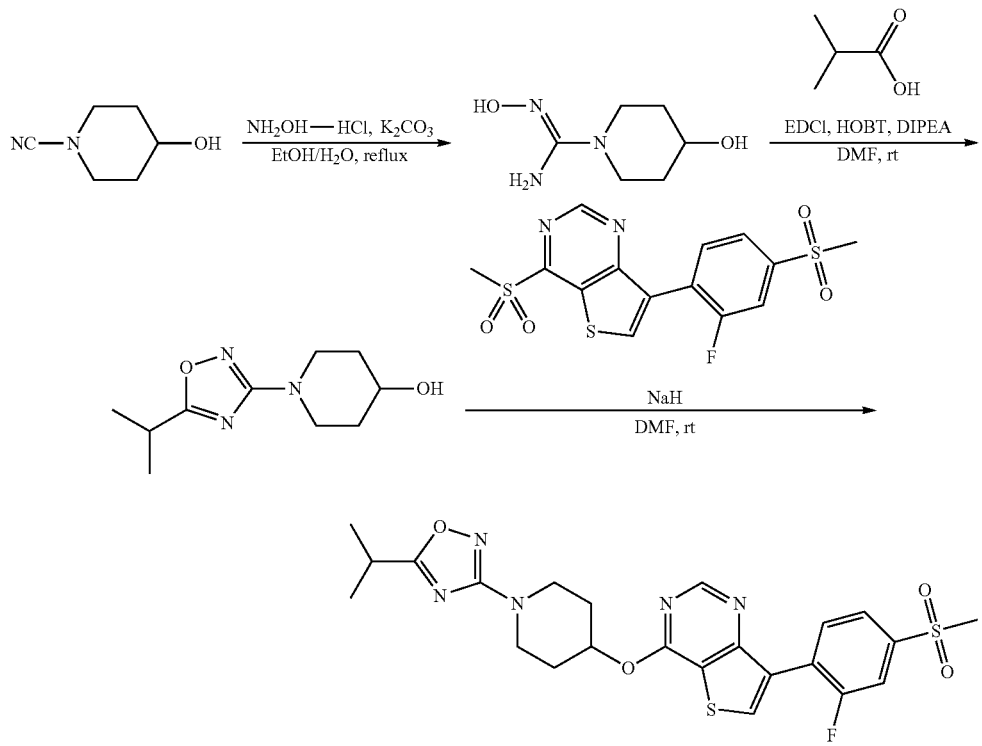

Example 95

7-(2-fluoro-4-methanesulfonyl-phenyl)-4[1-(5-isopropyl-[1,2,4]oxadiazol-3-yl)-piperidin-4-yloxy]-thieno[3,2d]pyrimidine

Step 95-1)
4,N-dihydroxy-piperidin-1-carboxamidine

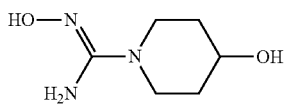

3 g of 4-hydroxy-1-nitrilpiperidine was added in a mixture of 30 ml ethanol and 30 ml water with stirring, and 6 g of potassium carbonate was added thereto. 6.2 g of hydroxyamine hydrochloride was dissolved in water, added slowly it dropwise to the mixture and refluxed for 12 hr. The resulting solution was distilled under a reduced pressure to remove ethanol and extracted three times with ethyl acetate. The organic layer was dried over anhydrous sodium sulfate, filtered and concentrated under a reduced pressure to obtain 3 g of the title compound as a colorless and transparent oil.

$^1$H NMR spectrum (300 MHz, DMSO-d$_6$): δ 8.71 (bs, 1H), 5.30 (s, 2H), 4.77 (m, 1H), 3.85 (m, 2H), 2.99 (m, 2H), 2.25 (m, 2H), 2.05-1.999 m, 2H).

Step 95-2) 1-(5-isopropyl-[1,2,4]oxadizo-3-yl)piperidin-4-ol

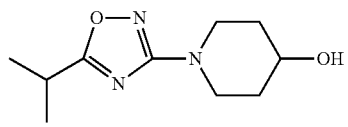

600 mg of isobutyric acid was dissolved in 50 ml of tetrahydrofuran, and 1.32 g of EDCI and 933 mg of HOBT were added thereto. 3.28 ml of diisopropylethylamine was added to the mixture, stirred for 15 min, and amidine compound obtained in step 95-1 dissolved in THF was dropwise added thereto. The resulting mixture was stirred at room temperature for 6 hr and sodium bicarbonate was added thereto. The resulting mixture was extracted with ethyl acetate, washed with water and saline solution, dried over anhydrous sodium sulfate, and concentrated under a reduced pressure to obtain 1 g of the title compound.

$^1$H NMR spectrum (300 MHz, DMSO-d$_6$): δ 4.88 (s, 1H), 4.55 (m, 1H), 3.85 (m, 2H), 2.99 (m, 2H), 2.25 (m, 2H), 2.05-1.99 (m, 2H), 0.99 (d, 6H).

Step 95-3) 7-(2-fluoro-4-methanesulfonyl-phenyl)-4[1-(5-isopropyl-[1,2,4]oxadiazol-3-yl)-piperidin-4-yloxy]-thieno[3,2-d]pyrimidine

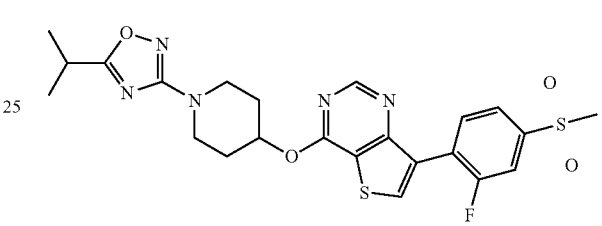

The procedure of Example 60 was repeated except for using 1-(5-isopropyl-[1,2,4]oxadiazo-3-yl)piperidin-4-ol obtained in step 95-2 instead of 1-(3-isopropyl-1,2,4-oxadiazol-5-yl)piperidin-4-ol to obtain the title compound.

$^1$H NMR spectrum (300 MHz, DMSO-d$_6$): δ 8.92 (s, 1H), 8.77 (s, 1H), 8.26 (t, 1H), 7.94 (t, 2H), 5.64 (m, 1H), 3.84 (m, 2H), 3.34 (s, 3H), 2.90 (m, 2H), 2.19 (m, 2H), 1.89 (m, 3H), 1.23 (d, 6H).

The compound of Example 96 was prepared by the procedure shown in Reaction Scheme 19.

[Reaction Scheme 19]

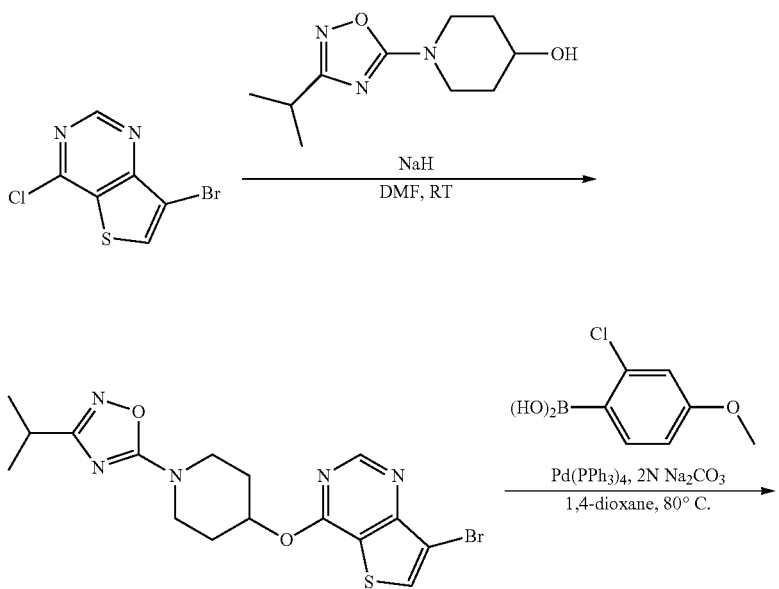

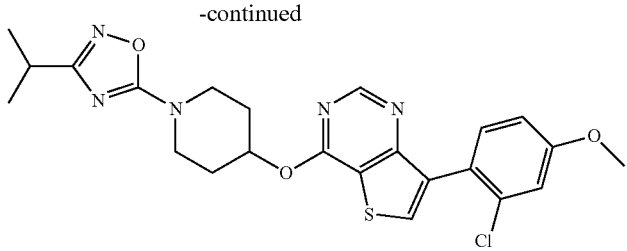

Example 96

5-(4-(7-(2-chloro-4-methoxyphenyl)thieno[3,2-d]pyrimidin-4-yloxy)piperidin-1-yl)-3-isopropyl-1,2,4-oxadiazole Step 96-1) 7-bromo-4-[1-(3-isopropyl-[1,2,4]oxadiazol-5-yl)-piperidin-4-yloxy]-thieno[3,2-d]pyrimidine

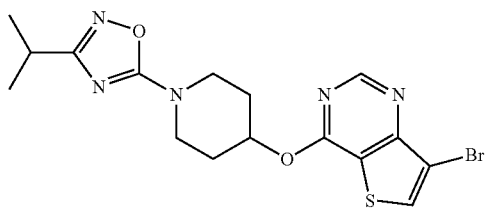 [SMILES: CC(C)c1noc(N2CCC(Oc3ncnc4c(Br)csc34)CC2)n1]

30 mg of 1-(3-isopropyl-1,2,4-oxadiazol-5-yl)piperidin-4-ol was dissolved in 2 ml of N,N-dimethylformamide and cooled to 0° C. 9 mg of NaH was added to the mixture and stirred for 30 min. 50 mg of 7-bromo-4-chloro-thieno[3,2-d]pyrimidine was added to the mixture, heated to room temperature and stirred for 2 hr. The resulting mixture was added with aqueous ammonium chloride and extracted twice with ethyl acetate. The organic layer was washed with water, dried over anhydrous sodium sulfate, and concentrated under a reduced pressure to obtain a bubble residue. The resulting residue was crystallized in diethylether solvent to obtain 50 mg of the title compound as a white solid.

$^1$H NMR spectrum (300 MHz, DMSO-$d_6$): δ 8.83 (s, 1H), 8.70 (s, 1H), 5.63 (m, 1H), 3.81 (m 2H), 3.56 (m, 1H), 2.81 (m, 1H), 2.16 (m, 2H), 1.90 (m, 2H), 1.06 (d, 6H).

Step 96-2) 5-(4-(7-(2-chloro-4-methoxyphenyl)thieno[3,2-d]pyrimidin-4-yloxy)piperidin-1-yl)-3-isopropyl-1,2,4-oxadiazole

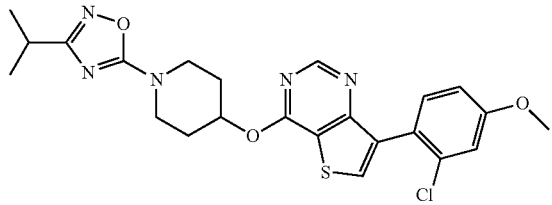 [SMILES: COc1ccc(-c2csc3c(OC4CCN(c5nc(C(C)C)no5)CC4)ncnc23)c(Cl)c1]

50 mg of 7-bromo-4-[1-(3-isopropyl-[1,2,4]oxadiazol-5-yl)-piperidin-4-yloxy]-thieno[3,2-d]pyrimidine was dissolved in 1 ml of 1,4-dioxane, and 35 mg of 2-chloro-4-methoxyboronate, 10 mg of triphosphine palladium tetrakis and 1 μl of 2N aqueous sodium carbonate were subsequently added thereto, followed by modifying the inner atmosphere with nitrogen gas. The resulting mixture was stirred at 100° C. for 12 hr, cooled to room temperature and added with water. The resulting solution was extracted with ethyl acetate, dried over anhydrous sodium sulfate, and concentrated under a reduced pressure to obtain a bubble residue. The resulting residue was crystallized in diethylether solvent to obtain 15 mg of the title compound as a white solid.

$^1$H NMR spectrum (300 MHz, DMSO-$d_6$): δ 8.85 (s, 1H), 8.35 (s, 1H), 7.50 (m, 1H), 7.20 (s, 1H), 7.00 (m, 1H), 5.60 (m, 1H), 3.93 (s, 3H), 3.51 (m 4H), 2.23 (m, 2H), 1.90 (m, 2H), 1.21 (d, 6H).

Example 97

4-[1-(3-isopropyl-[1,2,4]oxadiazol-5-yl)-piperidin-4-yloxy]-7-(2,3,4-trifluoro-phenyl)-thieno[3,2-d]pyrimidine

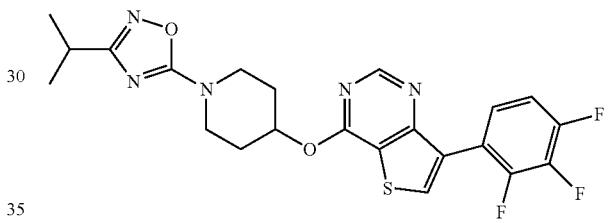

The procedure of Example 96 was repeated except for using 2,3,4-trifluorophenylboronic acid instead of 2-chloro-4-methoxyboronate in step 96-2 to obtain the title compound.

$^1$H NMR spectrum (300 MHz, DMSO-$d_6$): δ 8.80 (s, 1H), 8.10 (s, 1H), 7.89 (m, !H), 7.10 (m, 1H), 5.72 (m, 1H), 3.93 (m, 2H), 3.70 (m, 2H), 2.89 (m, 1H), 2.20 (m, 2H), 2.09 (m, 2H), 1.30 (d, 6H).

Example 98

7-(3-fluoro-4-methoxy-phenyl)-4-[1-(3-isopropyl-[1,2,4]oxadiazol-5-yl)-piperidin-4-yloxy]-thieno[3,2-d]pyrimidine

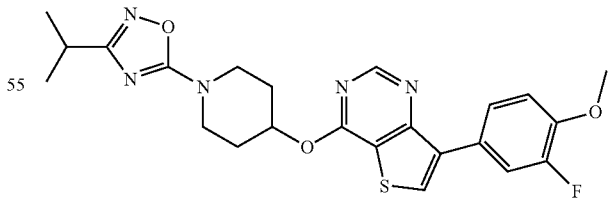

The procedure of Example 96 was repeated except for using 3-fluoro-4-methoxyphenylboronic acid instead of 2-chloro-4-methoxyboronate in step 96-2 to obtain the title compound.

$^1$H NMR spectrum (300 MHz, DMSO-$d_6$): δ 8.90 (s, 1H), 8.62 (s, 1H), 8.07 (d, 1H), 7.96 (s, 1H), 7.30 (t, 1H), 5.76 (m, 1H), 3.90 (s, 3H), 3.80 (m, 2H), 3.55 (m, 2H), 2.84 (m, 1H), 2.50 (m, 2H), 2.00 (m, 2H), 1.30 (d, 6H).

Example 99

4-[1-(3-isopropyl-[1,2,4]oxadiazol-5-yl)-piperidin-4-yloxy]-7-(4-trifluoromethoxy-phenyl)-thieno[3,2-d]pyrimidine

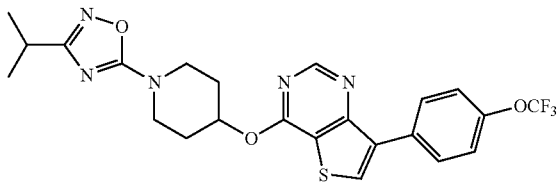 [SMILES: CC(C)c1noc(N2CCC(Oc3ncnc4c(-c5ccc(OC(F)(F)F)cc5)csc34)CC2)n1]

The procedure of Example 96 was repeated except for using 4-(trifluoromethoxy)phenylboronic acid instead of 2-chloro-4-methoxyboronate in step 96-2 to obtain the title compound.

$^1$H NMR spectrum (300 MHz, DMSO-$d_6$): δ 8.89 (s, 1H), 8.70 (s, 1H), 8.22 (d, 2H), 7.50 (d, 2H), 5.65 (m, 1H), 3.80 (m, 2H), 3.55 (m, 2H), 2.82 (m, 1H), 2.30 (m, 2H), 1.90 (m, 2H), 1.25 (d, 6H).

Example 100

4-[1-(3-isopropyl-[1,2,4]oxadiazol-5-yl)-piperidin-4-yloxy]-7-(4-trifluoromethylsulfanyl-phenyl)-thieno[3,2-d]pyrimidine

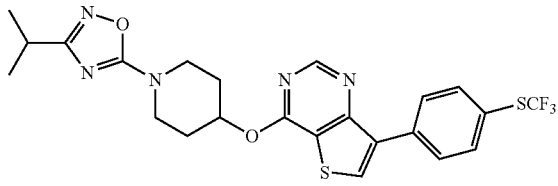

The procedure of Example 96 was repeated except for using 4,4,5,5-tetramethyl-2-(4-(trifluoromethylthiol)phenyl)-1,3,2-dioxaborolane instead of 2-chloro-4-methoxyboronate in step 96-2 to obtain the title compound.

$^1$H NMR spectrum (300 MHz, DMSO-$d_6$): δ 8.90 (s, 1H), 8.79 (s, 1H), 8.27 (d, 2H), 7.90 (d, 2H), 5.67 (m, 1H), 3.85 (m, 2H), 3.53 (m, 2H), 2.84 (m, 1H), 2.18 (m, 2H), 1.93 (m, 2H), 1.20 (d, 6H).

Example 101

7-(2-fluoro-4-trifluoro(methanesulfonyl)phenyl)-4-[1-(3-isopropyl-[1,2,4]oxadiazol-5-yl)-piperidin-4-yloxy]-thieno[3,2-d]pyrimidine

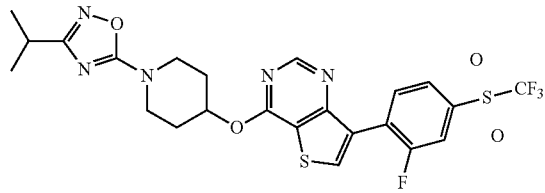

The procedure of Example 96 was repeated except for using 2-(2-fluoro-4-trifluoromethanesulfonyl-phenyl)-4,4,5,5-tetramethyl-1,3,2-dioxaborolane instead of 2-chloro-4-methoxyboronate in step 96-2 to obtain the title compound.

$^1$H NMR spectrum (300 MHz, DMSO-$d_6$): δ 9.02 (s, 1H), 8.94 (s, 1H), 8.60 (t, 1H), 8.28 (t, 2H), 5.65 (m, 1H), 3.85 (m, 2H), 3.57 (m, 2H), 2.87 (m, 2H), 2.63 (m, 2H), 2.00 (m, 2H), 1.20 (d, 6H)

Example 102

4-{4-[1-(3-isopropyl-[1,2,4]oxadiazol-5-yl)-piperidin-4-yloxy]-thieno[3,2-d]pyrimidin-7-yl}-benzoic acid methylester

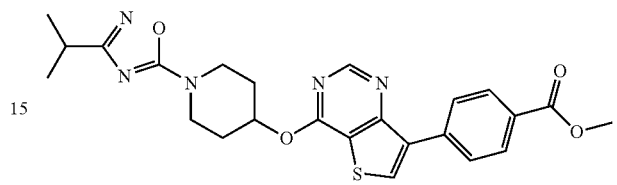

The procedure of Example 96 was repeated except for using 4-(methoxycarbonyl)benzene boronic acid instead of 2-chloro-4-methoxyboronate in step 96-2 to obtain the title compound.

$^1$H NMR spectrum (300 MHz, DMSO-$d_6$): δ 8.91 (s, 1H), 8.80 (s, 1H), 8.30 (d, 2H), 8.08 (d, 2H), 5.65 (m, 1H), 3.88 (m, 4H), 3.59 (m, 2H), 2.83 (m, 1H), 2.17 (m, 2H), 1.92 (m, 2H), 1.20 (d, 6H).

Example 103

1-(4-{4-[1-(3-isopropyl-[1,2,4]oxadiazol-5-yl)-piperidin-4-yloxy]-thieno[3,2-d]pyrimidin-7-yl}-phenyl)-ethanone

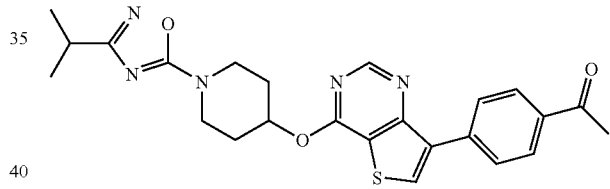

The procedure of Example 96 was repeated except for using 4-acetylbenzene boronic acid instead of 2-chloro-4-methoxyboronate in step 96-2 to obtain the title compound.

$^1$H NMR spectrum (300 MHz, DMSO-$d_6$): δ 8.90 (s, 1H), 8.80 (s, 1H), 8.30 (d, 2H), 8.08 (d, 2H), 5.65 (m, 1H), 3.85 (m, 2H), 3.59 (m, 2H), 2.83 (m, 1H), 2.62 (s, 3H), 2.18 (m, 2H), 1.92 (m, 2H), 1.20 (d, 6H).

Example 104

7-(4-cyclopropylsulfonyl-phenyl)-4-[1-(3-isopropyl-[1,2,4]oxadiazol-5-yl)-piperidin-4-yloxy]-thieno[3,2-d]pyrimidine

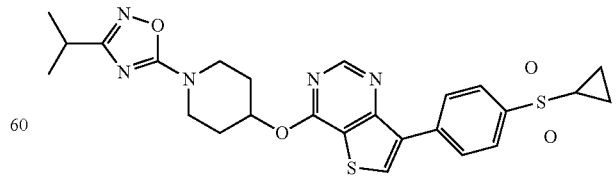

The procedure of Example 96 was repeated except for using 4-(cyclopropylsulfonyl)phenyl-4,4,5,5-tetramethyl-[1,3,2]dioxaborolan instead of 2-chloro-4-methoxyboronate in step 96-2 to obtain the title compound.

¹H NMR spectrum (300 MHz, DMSO-d₆): δ 8.91 (s, 1H), 8.84 (s, 1H), 8.36 (d, 2H), 8.02 (d, 2H), 5.65 (m, 1H), 3.84 (m, 2H), 3.60 (m, 2H), 2.90 (m, 1H), 2.86 (m, 1H), 2.77 (m, 2H), 2.58 (m, 2H), 2.33 (m, 1H), 2.18 (m, 2H), 1.97 (m, 3H), 1.11 (m, 2H), 0.99 (m, 2H).

Example 105

4-[1-(3-isopropyl-[1,2,4]oxadiazol-5-yl)-piperidin-4-yloxy]-7-(4-isopropylsulfonyl-phenyl)-thieno[3,2-d]pyrimidine

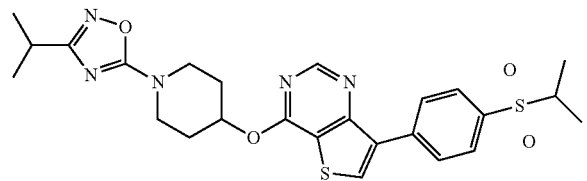

The procedure of Example 96 was repeated except for using 4-(isopropylsulfonyl)phenyl-4,4,5,5-tetramethyl-[1,3,2]dioxaborolane instead of 2-chloro-4-methoxyboronate in step 96-2 to obtain the title compound.

¹H NMR spectrum (300 MHz, DMSO-d₆): δ 8.91 (s, 1H), 8.84 (s, 1H), 8.36 (d, 2H), 8.02 (d, 2H), 5.65 (s, 1H), 3.84 (m, 2H), 3.60 (m, 2H), 2.90 (m, 1H), 2.85 (m, 2H), 2.83 (m, 1H), 2.32 (m, 2H), 1.21 (d, 6H), 0.10 (d, 6H).

Example 106

4-[1-(3-isopropyl-[1,2,4]oxadiazol-5-yl)-piperidin-4-yloxy]-7-(4-propylsulfonyl-phenyl)-thieno[3,2-d]pyrimidine

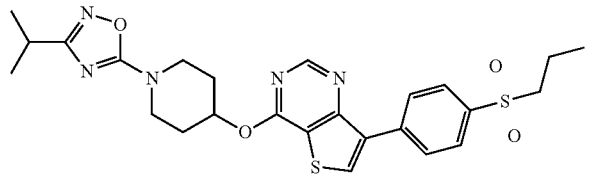

The procedure of Example 96 was repeated except for using 4-(propylsulfonyl)phenyl-4,4,5,5-tetramethyl-[1,3,2]dioxaborolane instead of 2-chloro-4-methoxyboronate in step 96-2 to obtain the title compound.

¹H NMR spectrum (300 MHz, DMSO-d₆): δ 8.92 (s, 1H), 8.85 (s, 1H), 8.40 (t, 1H), 8.03 (t, 2H), 5.76 (m, 1H), 3.614 (m, 2H), 3.54 (m, 2H), 3.20 (d, 1H), 2.85 (q, 2H), 2.25 (m, 2H), 1.95 (m, 2H), 1.65 (m, 2H), 1.20 (d, 6H), 0.95 (t, 3H).

Example 107

7-(2-fluoro-(4-propylsulfonyl)-phenyl)-4-[1-(3-isopropyl-[1,2,4]oxadiazol-5-yl)-piperidin-4-yloxy]-thieno[3,2-d]pyrimidine

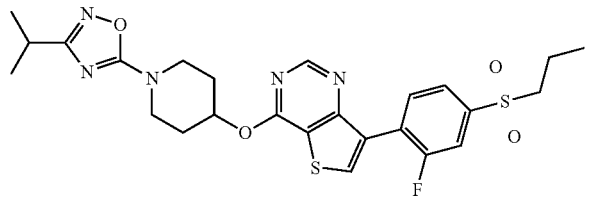

The procedure of Example 96 was repeated except for using 2-(2-fluoro-4-(propansulfonyl)phenyl)-4,4,5,5-tetramethyl-[1,3,2]dioxaborolan instead of 2-chloro-4-methoxyboronate in step 96-2 to obtain the title compound.

¹H NMR spectrum (300 MHz, DMSO-d₆): δ 8.86 (s, 1H), 8.73 (s, 1H), 8.28 (t, 1H), 7.90 (t, 2H), 5.69 (m, 1H), 3.84 (m, 2H), 3.43 (t, 2H), 2.84 (m, 2H), 2.18 (m, 2H), 1.91 (m, 2H), 1.61 (m, 2H), 1.20 (d, 6H), 0.96 (t, 3H).

Example 108

7-(4-cyclopentylsulfonyl-phenyl)-4-[1-(3-isopropyl-[1,2,4]oxadiazol-5-yl)-piperidin-4-yloxy]-thieno[3,2-d]pyrimidine

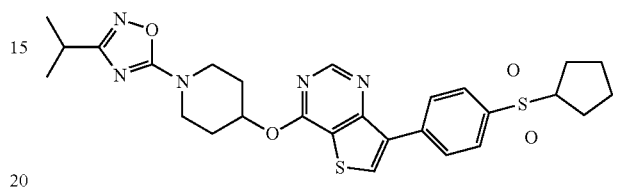

The procedure of Example 96 was repeated except for using 2-(4-(cyclopentylsulfonyl)phenyl)-4,4,5,5-tetramethyl-[1,3,2]dioxaborolane instead of 2-chloro-4-methoxyboronate in step 96-2 to obtain the title compound.

¹H NMR spectrum (300 MHz, DMSO-d₆): δ 8.92 (s, 1H), 8.85 (s, 1H), 8.40 (d, 2H), 8.03 (d, 2H), 5.76 (m, 1H), 3.95 (m, 2H), 3.65 (m, 2H), 2.90 (m, 2H), 2.85 (m, 1H), 2.25 (m, 4H), 1.95 (m, 8H), 1.65 (m, 6H), 1.20 (d, 6H), 0.95 (t, 2H).

The compound of Example 109 was prepared by the procedure shown in Reaction Scheme 20.

[Reaction Scheme 20]

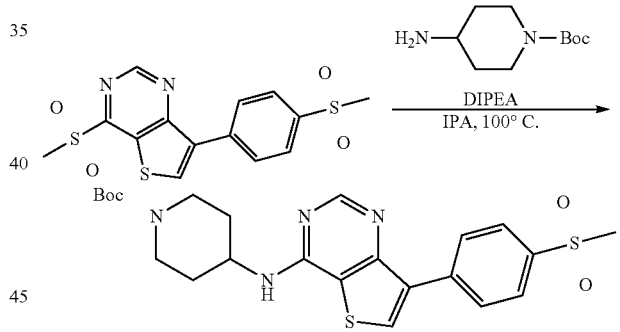

Example 109 tert-butyl 4-(7-(4-methanesulfonyl-phenyl)thieno[3,2-d]pyrimidin-4-ylamino)piperidin-1-carboxylate

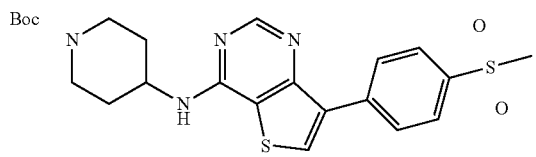

The procedure of Example 1 was repeated except for using tert-butyl 4-aminopiperidin-1-carboxylate instead of 4-(3-cyclopropyl-[1,2,4]oxadiazol-5-yl)piperidine to obtain the title compound.

$^1$H NMR spectrum (300 MHz, DMSO-d$_6$): δ 8.57 (s, 1H), 8.56 (s, 1H), 8.35 (d, 2H), 8.03 (d, 2H), 7.83 (d, 1H), 4.35 (m, 2H), 4.09-4.00 (m, 2H), 3.24 (s, 3H), 2.87 (m, 3H), 1.93-1.89 (m, 2H), 1.40 (s, 9H).

Example 110

7-(4-methanesulfonyl-phenyl)-N-(piperidin-4-yl)thieno[3,2-d]pyrimidin-4-amine

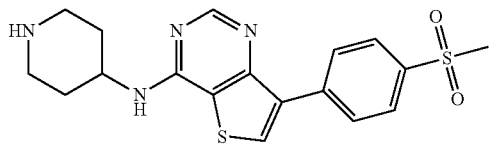 [SMILES: CS(=O)(=O)c1ccc(-c2csc3c(NC4CCNCC4)ncnc23)cc1]

The deprotection according to the procedure disclosed in step 5-3 in Preparation Example 5 was performed using the compound obtained in Example 109 to obtain the title compound.
$^1$H NMR spectrum (300 MHz, DMSO-d$_6$): δ 8.57 (s, 1H), 8.54 (s, 1H), 8.35 (d, 2H), 8.02 (d, 2H), 7.99 (m, 1H), 7.58 (d, 1H), 4.29 (m, 2H), 3.24 (s, 3H), 3.04-3.00 (m, 2H), 1.89-1.86 (m, 2H), 1.55-1.48 (m, 2H).

Example 111

N-(1-(5-ethylpyrimidin-2-yl)piperidin-4-yl)-7-(4-methanesulfonyl-phenyl)thieno[3,2-d]pyrimidin-4-amine

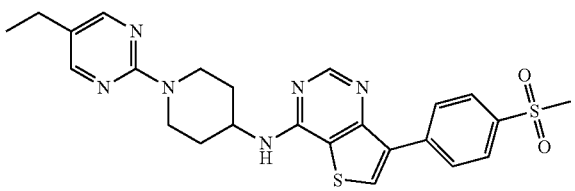 [SMILES: CCc1cnc(N2CCC(Nc3ncnc4c(-c5ccc(S(C)(=O)=O)cc5)csc34)CC2)nc1]

The procedure of intermediate 10 was repeated using 7-(4-methanesulfonyl-phenyl)-N-(piperidin-4-yl)thieno[3,2-d]pyrimidin-4-amine obtained in Example 110 and 2-chloro-5-ethylpyrimidine to obtain the title compound.
$^1$H NMR spectrum (300 MHz, DMSO-d$_6$): δ 8.56 (s, 1H), 8.34 (s, 1H), 8.26 (d, 2H), 8.00 (d, 2H), 7.82 (d, 1H), 4.67-4.63 (m, 2H), 3.23 (s, 3H), 3.04-3.00 (m, 2H), 2.43 (m, 2H), 1.99-1.96 (m, 2H), 1.54-1.51 (m, 2H).

Example 112 tert-butyl 4-(methyl(7-(4-methanesulfonyl-phenyl)thieno[3,2-d]pyrimidin-4-yl)amino)piperidin-1-carboxylate

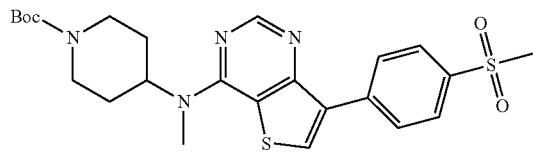

54 mg (0.11 mmol) of tert-butyl 4-(7-(4-methanesulfonyl-phenyl)thieno[3,2-d]pyrimidin-4-ylamino)piperidin-1-carboxylate obtained in Example 109 was dissolved in 2 ml of N,N-dimethylformamide, and 3.4 mg (0.143 mmol) of NaH was added thereto. After 0.5 hr, 10 μl (0.143 mmol) of iodomethane was dropwise added to the mixture at room temperature, heated to 50° C. and stirred for 3 hr. The resulting mixture was neutralized with 1 N aqueous hydrochloride, and extracted twice with ethyl acetate. The organic layer was dried over anhydrous sodium sulfate, filtered and distilled under a reduced pressure to obtain 40 mg of the title compound as a pale yellow solid.
$^1$H NMR spectrum (300 MHz, DMSO-d$_6$): δ 8.67 (s, 1H), 8.56 (s, 1H), 8.33 (d, 2H), 8.00 (d, 2H), 4.93 (m 1H), 4.21-4.10 (m, 2H), 3.25 (s, 3H), 2.89-2.82 (m, 2H), 1.90-1.73 (m, 4H), 1.43 (s, 9H).

Example 113

N-(1-(5-isopropyl-1,2,4-oxadiazol-3-yl)piperidin-4-yl)-N-methyl-7-(4-methanesulfonyl-phenyl)thieno[3,2-d]pyrimidin-4-amine

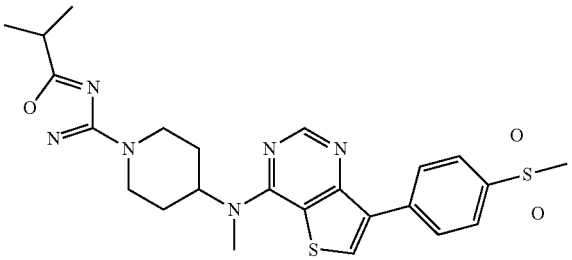

The procedure of Example 112 was repeated except for using 1-(3-isopropyl-1,2,4-oxdiazol-5-yl)piperidin-4-amine instead of tert-butyl 4-aminopiperidin-1-carboxylate to obtain the title compound.
$^1$H NMR spectrum (300 MHz, DMSO-d$_6$): δ 8.69 (s, 1H), 8.56 (s, 1H), 8.33 (d, 2H), 8.02 (d, 2H), 5.05 (m, 1H), 4.55 (m, 1H), 3.32 (s, 3H), 3.26 (s, 3H), 2.96 (m, 2H), 2.58 (m, 2H), 1.77 (m, 4H), 1.02 (d, 6H).

Example 114

[1-(5-ethylpyrimidin-2-yl)-piperidin-4-yl]-[7-(4-methanesulfonyl-phenyl)-thieno[3,2-d]pyrimidin-4-yl]-methylamine

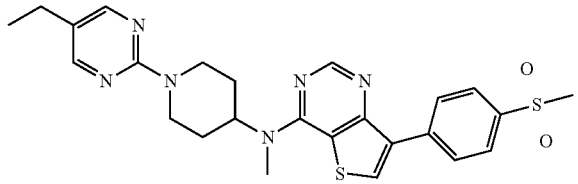

The procedure of Example 112 was repeated except for using 1-(5-ethylpyrimidin-2-yl)piperidin-4-amine instead of tert-butyl 4-aminopiperidin-1-carboxylate to obtain the title compound.
$^1$H NMR spectrum (300 MHz, DMSO-d$_6$): δ 8.68 (s, 1H), 8.57 (s, 1H), 8.34 (d, 2H), 8.26 (s, 2H), 8.02 (d, 2H), 4.84 (m, 2H), 4.12 (m, 2H), 3.39 (s, 3H), 3.34 (s, 3H), 3.15 (m, 2H), 2.48 (m, 3H), 1.65 (m, 2H), 1.02 (t, 3H).

Example 115

Ethyl-[7-(4-methanesulfonyl-phenyl)-thieno[3,2-d]pyrimidin-4-yl]-(5'-trifluoromethyl-3,4,5,6-tetrahydro-2H-[1,2']bipyridinyl-4-yl)amine

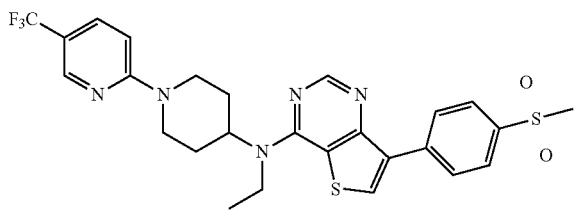

The procedure of Example 112 was repeated except for using 1-(5-(trifluoromethyl)pyridin-2-yl)piperidin-4-amine and iodoethane instead of tert-butyl 4-aminopiperidin-1-carboxylate and iodomethane to obtain the title compound.

$^1$H NMR spectrum (300 MHz, DMSO-d$_6$): δ 8.66 (s, 1H), 8.57 (s, 1H), 8.41 (s, 1H), 8.30 (d, 2H), 8.00 (d, 2H), 7.79 (d, 1H), 7.09 (d, 1H), 5.07 (m, 1H), 4.65 (m, 2H), 3.75 (m, 2H), 3.30 (s, 3H), 3.16 (m, 3H), 1.87 (m, 4H), 1.24 (t, 3H).

The compound of Example 116 was prepared by the procedure shown in Reaction Scheme 21.

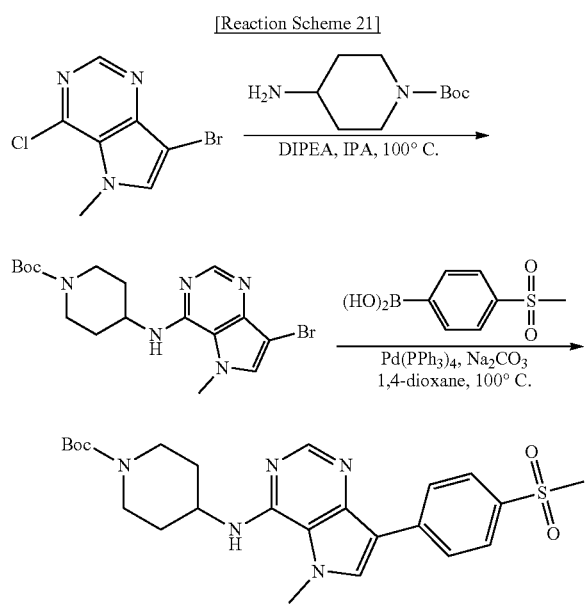

Example 116 tert-butyl 4-(5-methyl-7-(4-methanesulfonyl-phenyl)-5H-pyrrolo[3,2-d]pyrimidin-4-ylamino)piperidin-1-carboxylate Step 116-1) tert-butyl 4-(7-bromo-5-methyl-5H-pyrrolo[3,2-d]pyrimidin-4-ylamino)piperidin-1-carboxylate

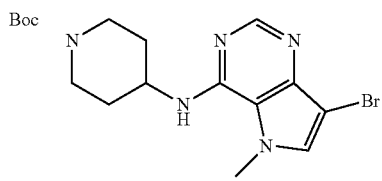 [SMILES: Cn1cc(Br)c2ncnc(NC3CCNCC3)c21 ; "Boc"]

The procedure of Example 1 was repeated using 7-bromo-4-chloro-5-methyl-5H-pyrrolo[3,2-d]pyrimidine obtained in Preparation Example 4 and 4-aminopiperidin-1-carboxyl-tert-butyl ester to obtain the title compound.

$^1$H NMR spectrum (300 MHz, DMSO-d$_6$): δ 8.18 (s, 1H), 7.60 (s, 1H), 6.31 (d, NH), 4.01 (s, 3H), 3.98 (m, 2H), 3.39 (m, 1H), 2.85 (m, 2H), 1.87 (m, 2H), 1.55 (m, 2H), 1.42 (s, 9H).

Step 116-2) tert-butyl 4-(5-methyl-7-(4-methane-sulfonyl-phenyl)-5H-pyrrolo[3,2-d]pyrimidin-4-ylamino)piperidin-1-carboxylate

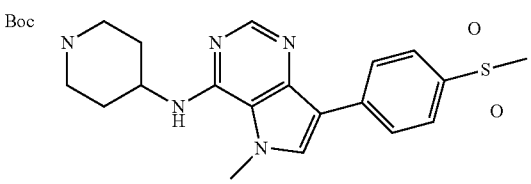

tert-butyl 4-(7-bromo-5-methyl-5H-pyrrolo[3,2-d]pyrimidin-4-yl amino)piperidin-1-carboxylate, 73 mg of 4-methanesulfonyl-phenylboronic acid, 17 mg of Pd(PPh$_3$)$_4$ and 0.73 ml of 2N Na$_2$CO$_3$ were added in 3 ml of 1,4-dioxane and stirred in a closed reactor at 100° C. for 12 hr. The resulting mixture was cooled to room temperature, extracted with ethylacetate and distilled water. The organic layer was washed with water and saline solution, dried over anhydrous sodium sulfate and concentrated under a reduced pressure to obtain 15 mg of the title compound.

$^1$H NMR spectrum (300 MHz, DMSO-d$_6$): δ 8.41 (d, 2H), 8.32 (s, 1H), 8.14 (s, 1H), 7.90 (d, 2H), 6.31 (d, NH), 4.36 (m, 1H), 4.11 (s, 3H), 3.98 (m, 2H), 3.18 (s, 3H), 2.90 (m, 2H), 1.94 (m, 2H), 1.60 (m, 2H), 1.24 (s, 9H).

Example 117

3-isopropyl-5-(1-(5-methyl-7-(4-methanesulfonyl-phenyl)-5H-pyrrolo[3,2-d]pyrimidin-4-yl)piperidin-4-yl)-1,2,4-oxadiazole

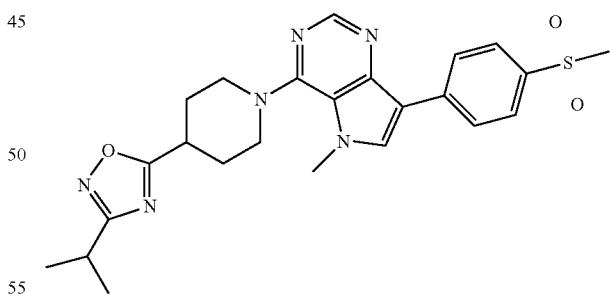

The procedure of Example 12 was repeated except for using 7-bromo-4-chloro-5-methyl-5H-pyrrolo[3,2-d]pyrimidine instead of 7-bromo-4-chlorothieno[3,2-d]pyrimidine to obtain the title compound.

$^1$H NMR spectrum (300 MHz, DMSO-d$_6$): δ 8.57 (s, 1H), 8.46 (d, 2H), 8.41 (s, 1H), 7.95 (d, 2H), 4.06 (s, 3H), 3.78 (m, 2H), 3.22 (s, 3H), 3.11 (m, 3H), 2.23 (m, 2H), 1.99 (m, 2H), 1.28 (s, 3H), 1.26 (s, 3H).

The compound of Example 118 was prepared by the procedure shown in Reaction Scheme 22.

[Reaction Scheme 22]

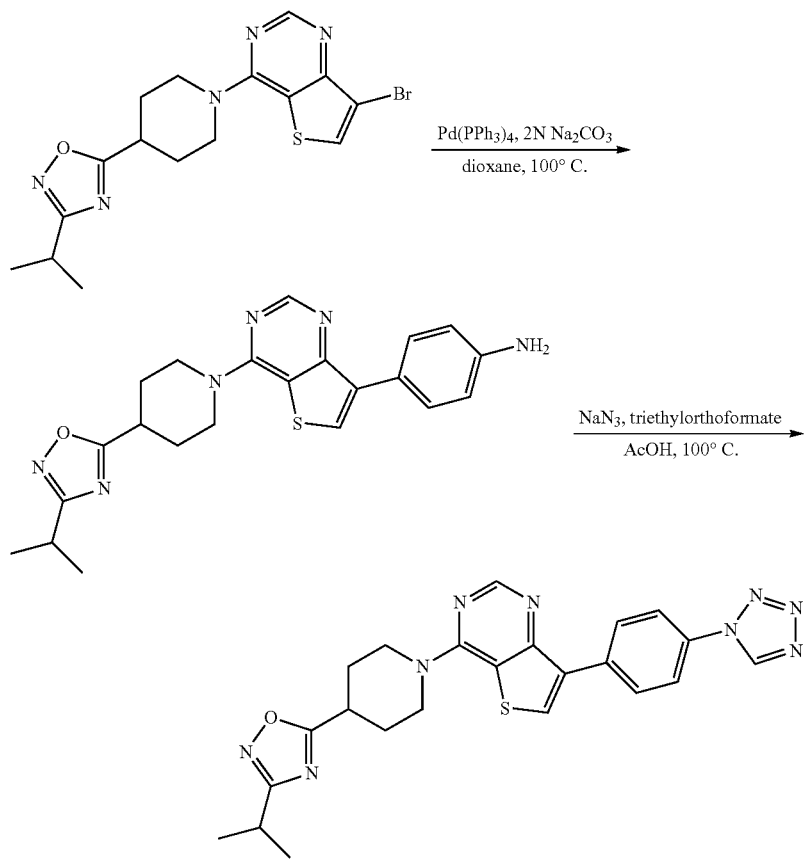

Example 118

5-(1-(7-(4-(1H-tetrazol-1-yl)phenyl)thieno[3,2-d]pyrimidin-4-yl)piperidin-4-yl)-3-iso propyl-1,2,4-oxadiazole Step 118-1) 4-(4-(4-(3-isopropyl-1,2,4-oxadiazol-5-yl)piperidin-1-yl)thieno[3,2-d]pyrimidin-7-yl)benzenamine

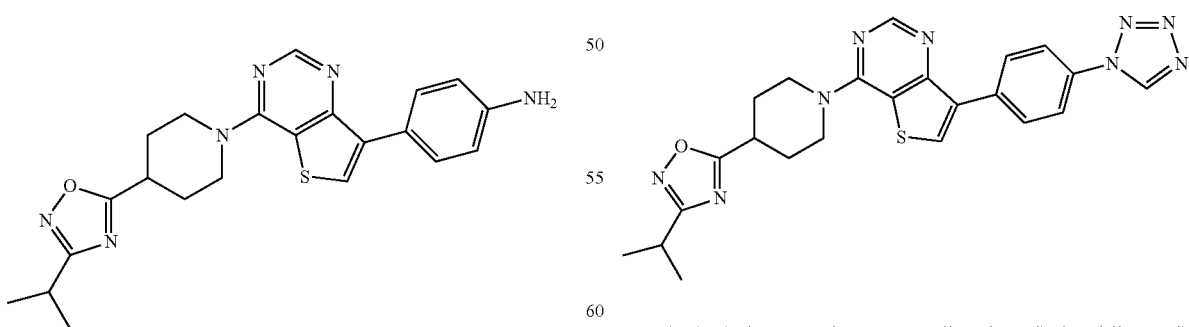

The procedure of Example 12 was repeated except for using 4-(4,4,5,5-tetramethyl-1,3,2-dioxaborolan-2-yl)benzenamine instead of 7-(2-fluoro-4-methanesulfonyl-phenyl)-4,4,5,5-tetramethyl-[1,3,2]dioxaborolane in step 12-2 to obtain the title compound.

$^1$H NMR spectrum (300 MHz, DMSO-$d_6$): δ 8.60 (s, 1H), 8.14 (s, 1H), 7.76 (d, 2H), 6.66 (d, 2H), 5.26 (s, 2H), 4.71-4.67 (m, 2H), 3.59-3.50 (m, 2H), 3.46 (m, 1H), 3.09-3.02 (m, 1H), 2.29-2.25 (m, 2H), 1.89-1.77 (m, 2H), 1.26 (d, 6H).

Step 118-2) 5-(1-(7-(4-(1H-tetrazol-1-yl)phenyl)thieno[3,2-d]pyrimidin-4-yl)piperidin-4-yl)-3-iso propyl-1,2,4-oxadiazole 4-(4-(4-(3-isopropyl-1,2,4-oxadiazol-5-yl)piperidin-1-yl)thieno[3,2-d]pyrimidin-7-yl)benzenamine was dissolved in acetic acid, and triethylorthoformate and sodium azide were added thereto followed by stirring at 100° C. for 12 hr. When the reaction is terminated, the resulting mixture was distilled under a reduced pressure to remove acetic acid, and ethyl acetate was added thereto, followed by washing with satuated sodium bicarbonate and water. Subsequently, the resultant was dried over anhydrous sodium sulfate, filtered and distilled under a reduced pressure to obtain the title compound.

$^1$H NMR spectrum (300 MHz, DMSO-$d_6$): δ 10.03 (s, 1H), 8.59 (s, 1H), 8.44 (s, 1H), 7.97-7.94 (d, 2H), 7.66-7.63 (d, 2H), 4.68-4.64 (m, 2H), 3.68-3.44 (m, 3H), 3.05-2.90 (m, 1H), 2.21-2.17 (m, 2H), 1.85-1.78 (m, 2H), 1.23-1.21 (d, 6H).

The compound of Preparation Example 7 was prepared by the procedure shown in Reaction Scheme 23.

[Reaction Scheme 23]

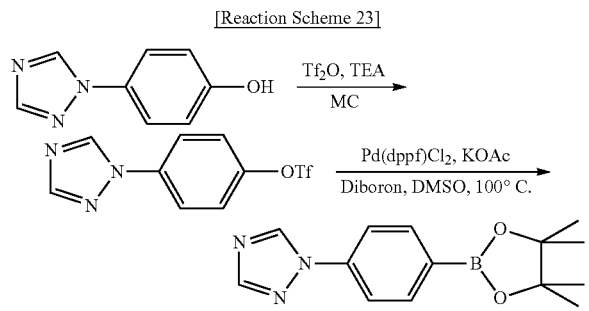

Preparation Example 7

1-[4-(4,4,5,5-tetramethyl-[1,3,2]dioxaborolan-2-yl)-phenyl]-1H-[1,2,4]triazole

Step 7-1) trifluoro-methane sulfonic acid 4-[1,2,4]triazol-1-yl-phenyl ester

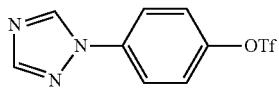

1.0 g of 4-[1,2,4]triazol-1-yl-phenol was dissolved in 10 ml of dichloromethane, and 1.72 ml of triethylamine was added thereto. 1.56 ml of Tf$_2$O was added to the mixture and stirred for 5 hr. The reaction was terminated by using water, and the resulting mixture was extracted with dichloromethane, dried over anhydrous sodium sulfate, and concentrated under a reduced pressure to obtain the title compound.

$^1$H NMR spectrum (300 MHz, DMSO-$d_6$): δ 9.38 (s, 1H), 8.31 (s, 1H), 7.75 (d, 2H), 7.63 (d, 2H).

Step 7-2) 1-[4-(4,4,5,5-tetramethyl-[1,3,2]dioxaborolan-2-yl)-phenyl]-1H-[1,2,4]triazole

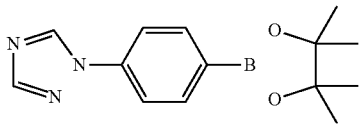

0.3 g of trifluoro-methane sulfonic acid 4-[1,2,4]triazol-1-yl-phenyl ester obtained in step 7-1 of Preparation Example 7 was added in 3 ml of DMSO, and 67 mg of palladium catalyst, 300 mg of KOAc and 285 mg of diborane were added thereto at a time. The inner atmosphere was modified with argon gas, heated to 100° C. and stirred for 30 min. The reaction was terminated by using sodium carbonate solution, extracted with ethyl acetate, dried over anhydrous sodium sulfate, and concentrated under a reduced pressure. The resulting residue was purified by column chromatography (dichloromethane:methanol=50:1) to obtain the title compound $^1$H NMR spectrum (300 MHz, DMSO-$d_6$): δ 9.37 (s, 1H), 8.25 (s, 1H), 7.90 (d, 2H), 7.82 (d, 2H), 1.15 (s, 12H).

Example 119

5-(4-(7-(4-(1H-1,2,4-triazol-1-yl)phenyl)thieno[3,2-d]pyrimidin-4-yloxy)piperidin-1-yl)-3-tert-butyl-1,2,4-oxadiazole

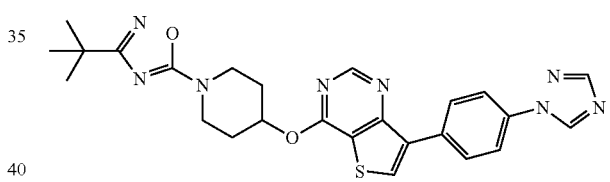

The procedure of Example 96 was repeated except for using 1-(3-tert-butyl-1,2,4-oxadiazol-5-yl)piperidin-4-ol and 1-[4-(4,4,5,5-tetramethyl-[1,3,2]dioxaborolan-2-yl)-phenyl]-1H-[1,2,4]triazol instead of 1-(3-isopropyl-1,2,4-oxadiazol-5-yl)piperidin-4-ol and 2-chloro-4-methoxyboronate to obtain the title compound.

$^1$H NMR spectrum (300 MHz, DMSO-$d_6$): δ 9.38 (s, 1H), 8.91 (s, 1H), 8.74 (s, 1H), 8.32 (d, 2H), 8.28 (s, 1H), 7.99 (d, 2H), 5.62 (m, 1H), 3.81 (m, 2H), 3.57 (m 2H), 2.17 (m, 2H), 1.91 (m, 2H), 1.24 (s, 9H).

The compound of Example 120 was prepared by the procedure shown in Reaction Scheme 24.

[Reaction Scheme 24]

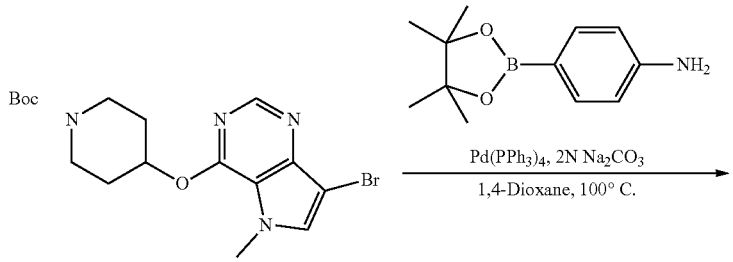

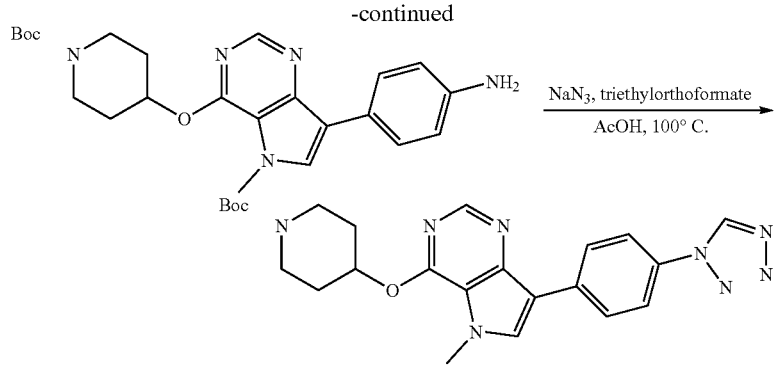

Example 120 tert-butyl 4-(7-(4-(1H-tetrazol-1-yl)phenyl)-5-methyl-5H-pyrrolo[3,2-d]pyrimidin-4-yloxy)piperidin-1-carboxylate Step 120-1) tert-butyl 4-(7-(4-aminophenyl)-5-methyl-5H-pyrrolo[3,2-d]pyrimidin-4-yloxy)piperidin-1-carboxylate

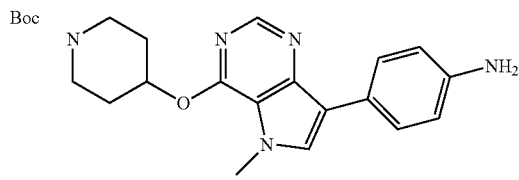 [SMILES: Cn1cc(-c2ccc(N)cc2)c2ncnc(OC3CCNCC3)c21 ; "Boc"]

The procedure of step 25-2 in Example 25 was repeated except for using 4-aminophenylboronic acid instead of 4-methanesulfonyl-phenylboronic acid to obtain the title compound.

$^1$H NMR spectrum (300 MHz, DMSO-d$_6$): δ 8.40 (s, 1H), 7.87 (s, 1H), 7.78 (d, 2H), 6.60 (d, 2H), 5.54 (m, 1H), 5.01 (s, NH) 4.01 (s, 3H), 3.58 (m, 2H), 3.42 (m, 2H), 2.01 (m, 2H), 1.78 (m, 2H), 1.42 (s, 9H).

Step 120-2) tert-butyl 4-(7-(4-(1H-tetrazol-1-yl)phenyl)-5-methyl-5H-pyrrolo[3,2-d]pyrimidin-4-yloxy)piperidin-1-carboxylate

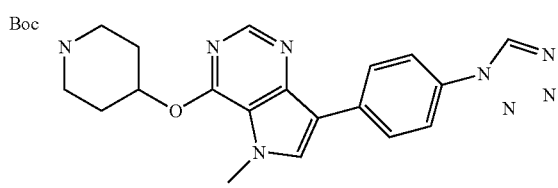

The procedure of step 118-2 in Example 118 was repeated using the compound obtained in step 120-1 of Example 120 to obtain the title compound.

$^1$H NMR spectrum (300 MHz, DMSO-d$_6$): δ 10.10 (s, 1H), 8.52 (s, 1H), 8.44 (d, 2H), 8.34 (s, 1H), 7.95 (d, 2H), 5.57 (m, 1H), 4.09 (s, 3H), 3.59 (m, 2H), 3.44 (m, 2H), 2.00 (m, 2H), 1.80 (m, 2H), 1.42 (s, 9H).

Example 121

4-(4-(1-(5-ethylpyrimidin-2-yl)piperidin-4-yloxy)-5-methyl-5H-pyrrolo[3,2-d]pyrimidin-7-yl)benzenamine

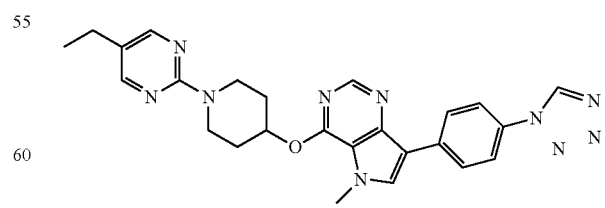

The procedure of Example 27 was repeated except for using 4-aminophenylboronic acid instead of 4-methanesulfonyl-phenylboronic acid to obtain the title compound.

$^1$H NMR spectrum (300 MHz, DMSO-d$_6$): δ 8.42 (s, 1H), 8.27 (s, 2H), 7.87 (s, 1H), 7.84 (d, 2H), 6.61 (d, 2H), 5.62 (m, 1H), 5.02 (s, NH), 4.02 (s, 3H), 4.02 (m, 2H), 3.80 (m, 2H), 2.44 (dd, 2H), 2.05 (m, 2H), 1.84 (m, 2H), 1.14 (t, 3H).

Example 122

7-(4-(1H-tetrazol-1-yl)phenyl)-4-(1-(5-ethylpyrimidin-2-yl)piperidin-4-yloxy)-5-methyl-5H-pyrrolo[3,2-d]pyrimidine The procedure of step 118-2 in Example 118 was repeated using 4-(4-(1-(5-ethylpyrimidin-2-yl)piperidin-4-yloxy)-5-methyl-5H-pyrrolo[3,2-d]pyrimidin-7-yl)benzenamine obtained in Example 121 to obtain the title compound.

$^1$H NMR spectrum (300 MHz, DMSO-d$_6$): δ 10.10 (s, 1H), 8.54 (s, 1H), 8.44 (d, 2H), 8.43 (s, 1H), 8.28 (s, 2H), 7.96 (d, 2H), 5.65 (m, 1H), 4.08 (s, 3H), 4.06 (m, 2H), 3.82 (m, 2H), 2.44 (dd, 2H), 2.08 (m, 2H), 1.86 m, 2H), 1.14 (t, 3H).

Example 123

7-(4-(1H-tetrazol-1-yl)phenyl)-5-methyl-4-(1-(5-(trifluoromethyl)pyrimidin-2-yl)piperidin-4-yloxy)-5H-pyrrolo[3,2-d]pyrimidine

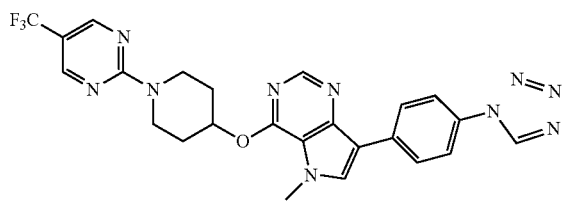

The procedure of Example 120 was repeated except for using 1-(5-(trifluoromethyl)pyrimidin-2-yl)piperidin-4-ol instead of t-butyl 4-hydroxypiperidin-1-carboxylate to obtain the title compound.

$^1$H NMR spectrum (300 MHz, DMSO-d$_6$): δ 10.09 (s, 1H), 8.71 (s, 1H), 8.53 (s, 1H), 8.43 (d, 2H), 8.34 (s, 1H), 7.94 (d, 2H), 5.68 (m, 1H), 4.08 (s, 3H), 4.04 (m, 4H), 2.10 (m, 2H), 1.92 (m, 2H).

Example 124

(S)-tert-butyl 3-[5-methyl-7-(4-amino-phenyl)-5H-pyrrolo[3,2-d]pyrimidin-4-yloxy)pyrrolidin-1-carboxylate

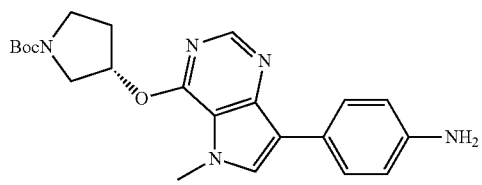 [SMILES: Cn1cc(-c2ccc(N)cc2)c2ncnc(O[C@H]3CCN(C(=O)OC(C)(C)C)C3)c21]

The procedure of step 120-1 in Example 120 was repeated except for using (S)-t-butyl-3-hydroxypyrrolidin-1-carboxylate instead of t-butyl 4-hydroxypiperidin-1-carboxylate to obtain the title compound.

$^1$H NMR spectrum (300 MHz, CDCl$_3$): δ 8.52 (s, 1H), 7.77 (d, 2H), 7.30 (s, 1H), 6.75 (d, 2H), 5.85 (s, 1H), 3.99 (s, 3H), 3.75-3.51 (m, 6H), 2.26 (s, 2H), 1.46 (s, 9H), 1.22 (s, 2H).

Example 125

(S)-tert-butyl 3-[5-methyl-7-(4-tetrazol-1-yl-phenyl)-5H-pyrrolo[3,2-d]pyrimidin-4-yloxy)pyrrolidin-1-carboxylate

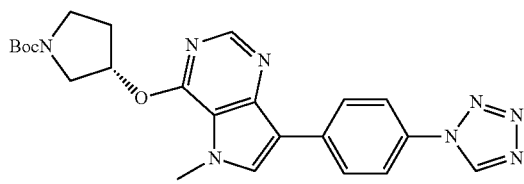 [SMILES: Cn1cc(-c2ccc(-n3cnnn3)cc2)c2ncnc(O[C@H]3CCN(C(=O)OC(C)(C)C)C3)c21]

The procedure of step 120-2 in Example 120 was repeated using (S)-tert-butyl 3-[5-methyl-7-(4-amino-phenyl)-5H-pyrrolo[3,2-d]pyrimidin-4-yloxy)pyrrolidin-1-carboxylate obtained in Example 124 to obtain the title compound.

$^1$H NMR spectrum (300 MHz, CDCl$_3$): δ 9.00 (s, 1H), 8.59 (s, 1H), 8.27 (d, 2H), 7.74 (d, 2H), 7.58 (s, 1H), 5.90 (s, 1H), 4.07 (s, 3H), 3.78-3.54 (m, 4H), 2.30 (s, 2H), 1.47 (s, 9H).

Test Example 1

Controlling Effect of GPR119 in CRE-bla CHO-K1 Cells (EC$_{50}$)

The day before the experiment, GPR119 CRE-bla CHO-K1 cell line purchased from Invitrogen was seeded in a 96 black well plate in an amount of 80 μl at a density of 5×10$^4$ cells. After the seeding, 10 μl of doxycycline in a concentration of 1 μg/ml was added to each well and incubated in an incubator at 37° C. under 5% CO$_2$ for about 16 to 20 hr.

The day of experiment, sample compounds were performed a 10-fold serial dilution with a culture medium at various concentrations of 1 uM to 0.01 mM. Considering that the culture medium used in the seeding and doxycycline are together applied, the sample compounds were diluted to a 5-fold dilution of the planned concentration. 20 μl of the compound diluted with the culture medium was added to each well and incubated in the incubator for 5 hr. The compound-untreated group was added with 20 μl of 0.5% dimethyl sulfoxide (DMSO) diluted with the culture medium. After 5 hr from the incubation, substrate mixture of a 6-fold concentration were prepared; 6 μl of 1 mM LiveBLAzer™-FRET B/G(CCF4-AM) substrate, 60 μl of solution B, 904 μl of solution C and 30 μl of solution D. 12 μl of the substrate mixture was added to each well and allowed to be kept at room temperature for 2 hr with shading the light. Fluorescence intensity value of blue channel and green channel was determined by a fluorescence microplate reader at 409 nm/460 nm and 409 nm/630 nm (excitation/emission), respectively. In order to confirm the controlling effect of the inventive compounds against GPR119, EC$_{50}$ (half maximal effective concentration) was determined based on the determined values. EC$_{50}$, the concentration at which 50% activity of β-lactamase, was determined according to the following Equation:

$$\text{Equation} = [(Ti-Tz)/(C-Tz)] \times 100$$

[Wherein, Ti: Cell density of the compound-treated group; Tz: Cell density of the negative control group; and C: Cell density of the positive control group]

The results on the controlling effect against GPR119 in CRE-bla CHO-K1 cell line (EC$_{50}$) are shown in Table 1.

TABLE 1

| Example | CRE-bla CHO-K1 |
|---|---|
| 1 | * |
| 2 | *** |
| 3 | *** |
| 4 | ** |
| 5 | * |
| 6 | * |
| 7 | * |
| 8 | ** |
| 9 | ** |
| 10 | ** |
| 11 | ** |
| 12 | * |
| 13 | *** |
| 14 | *** |
| 15 | ** |
| 16 | ** |
| 17 | * |
| 18 | * |

TABLE 1-continued

| Example | CRE-bla CHO-K1 |
|---|---|
| 19 | * |
| 20 | * |
| 21 | * |
| 22 | * |
| 23 | * |
| 24 | * |
| 25 | * |
| 26 | *** |
| 27 | * |
| 28 | * |
| 29 | * |
| 30 | * |
| 31 | * |
| 32 | * |
| 33 | * |
| 34 | * |
| 35 | * |
| 36 | * |
| 37 | * |
| 38 | *** |
| 39 | ** |
| 40 | ** |
| 41 | *** |
| 42 | *** |
| 43 | *** |
| 44 | ** |
| 45 | ** |
| 46 | ** |
| 47 | *** |
| 48 | *** |
| 49 | ** |
| 50 | * |
| 51 | * |
| 52 | * |
| 53 | * |
| 54 | * |
| 55 | * |
| 56 | * |
| 57 | * |
| 58 | ** |
| 59 | *** |
| 60 | * |
| 61 | * |
| 62 | * |
| 63 | * |
| 64 | * |
| 65 | * |
| 66 | * |
| 67 | * |
| 68 | ** |
| 69 | * |
| 70 | * |
| 71 | * |
| 72 | * |
| 73 | * |
| 74 | *** |
| 75 | ** |
| 76 | *** |
| 77 | * |
| 78 | * |
| 79 | * |
| 80 | * |
| 81 | * |
| 82 | * |
| 83 | * |
| 84 | * |
| 85 | * |
| 86 | * |
| 87 | *** |
| 88 | * |
| 89 | * |
| 90 | *** |
| 91 | * |
| 92 | * |
| 93 | *** |
| 94 | * |
| 95 | * |
| 96 | * |

TABLE 1-continued

| Example | CRE-bla CHO-K1 |
|---|---|
| 97 | *** |
| 98 | *** |
| 99 | ** |
| 100 | *** |
| 101 | *** |
| 102 | ** |
| 103 | * |
| 104 | * |
| 105 | * |
| 106 | * |
| 107 | * |
| 108 | * |
| 109 | ** |
| 110 | *** |
| 111 | *** |
| 112 | * |
| 113 | ** |
| 114 | *** |
| 115 | *** |
| 116 | *** |
| 117 | ** |
| 118 | ** |
| 119 | * |
| 120 | * |
| 121 | *** |
| 122 | * |
| 123 | * |
| 125 | *** |

* $EC_{50}$ value is <100 nM;
** $EC_{50}$ value is 100~1,000 nM
*** $EC_{50}$ value is >1,000 nM As shown in Table 1, the compounds of the present invention show an excellent controlling effect against CRE-bla CHO-K1.

What is claimed is:

1. A compound selected from the group consisting of a bicyclic heteroaryl compound of formula (I), a pharmaceutically acceptable salt thereof, a hydrate thereof, and a solvate thereof:

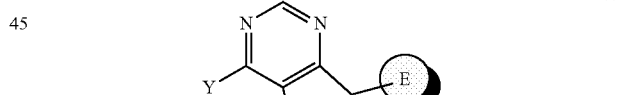

(I)

wherein,

X is S or $NR^1$, $R^1$ is H or $C_{1-4}$ alkyl;

E is $C_{6-14}$ aryl or $C_{2-13}$ heteroaryl, wherein E is optionally substituted with one to three substituents selected from the group consisting of halogen, —$NO_2$, —CN, —$CF_3$, $C_{1-6}$ alkyl, $C_{3-8}$ cycloalkyl, —$NH_2$, $C_{1-6}$ alkylamino, $diC_{1-6}$ alkylamino, $C_{1-6}$ alkoxy, —S—$C_{1-6}$ alkyl, —$S(O)_2$—$C_{1-6}$ alkyl, —$S(O)_2$—$C_{1-6}$ alkylamino, —$S(O)_2$-$diC_{1-6}$ alkylamino, —C(O)—$C_{1-6}$ alkyl, carboxyl, —$C(O)_2$—$C_{1-6}$ alkyl, —C(O)—$C_{1-6}$ alkylamino, —C(O)-$diC_{1-6}$ alkylamino, $C_{6-14}$ aryl, $C_{1-13}$ heteroaryl and $C_{2-13}$ heterocycloalkyl, wherein said substitutuents aryl, heteroaryl and heterocycloalkyl are optionally each independently additionally substituted with $C_{1-6}$ alkyl, halogen, $diC_{1-6}$ alkylamino or $C_{1-6}$ alkoxy; and Y is

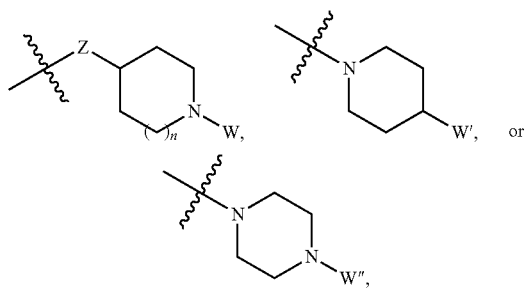

wherein,
Z is O, OCH$_2$ or NR$^2$; wherein R$^2$ is —H, —OH, C$_{1-3}$ alkyl; n is 0, 1 or 2;

W is —H, —C$_{1-6}$ alkyl, —C(O)—C$_{1-6}$ alkyl, —C(O)—C$_{6-14}$ aryl, —C(O)—C$_{1-13}$ heteroaryl, —C(O)$_2$—C$_{1-6}$ alkyl, —C(O)$_2$—C$_{6-14}$ aryl, —C(O)—C$_{1-6}$ alkylamino or C$_{1-13}$ heteroaryl, wherein said aryl and heteroaryl are optionally each independently substituted with a C$_{1-6}$ alkyl, a halogen, a C$_{1-6}$ alkoxy, or a C$_{3-8}$ cycloalkyl;

W' is —C(O)—C$_{1-6}$ alkyl, —C(O)—C$_{6-14}$ aryl or C$_{1-5}$ heteroaryl, wherein said aryl and heteroaryl are optionally each independently substituted with a C$_{1-6}$ alkyl, a halogen, a C$_{1-6}$ alkoxy, or a C$_{3-8}$ cycloalkyl; and W" is —C(O$_2$)—C$_{1-6}$ alkyl or C$_{1-5}$ heteroaryl, wherein said heteroaryl is optionally substituted with a C$_{1-6}$ alkyl, a halogen, a C$_{1-6}$ alkoxy, or a C$_{3-8}$ cycloalkyl.

2. The compound of claim 1, wherein E is pyrrolyl, imidazolyl, pyrazolyl, phenyl, pyridinyl, or pyrimidinyl, and wherein E is optionally substituted with one to three substituents selected from the group consisting of halogen, —NO$_2$, —CN, —CF$_3$, C$_{1-6}$ alkyl, C$_{3-8}$ cycloalkyl, —NH$_2$, C$_{1-6}$ alkylamino, diC$_{1-6}$ alkylamino, C$_{1-6}$ alkoxy, —S—C$_{1-6}$ alkyl, —S(O)$_2$—C$_{1-6}$ alkyl, —S(O)$_2$—C$_{1-6}$ alkylamino, —S(O)$_2$-diC$_{1-6}$ alkylamino, —C(O)—C$_{1-6}$ alkyl, carboxyl, —C(O)$_2$—C$_{1-6}$ alkyl, —C(O)—C$_{1-6}$ alkylamino, —C(O)-diC$_{1-6}$ alkylamino, C$_{6-14}$ aryl, C$_{1-13}$ heteroaryl and C$_{2-13}$ heterocycloalkyl.

3. The compound of claim 2, wherein said aryl is phenyl, said heteroaryl is pyrrolyl, imidazolyl, pyrazolyl, tetrazolyl, oxadiazolyl, thiazolyl, pyridinyl or pyrimidinyl, and said heterocycloalkyl is pyrrolidinyl, piperidinyl, piperazinyl, or morpholinyl, and wherein said aryl, heteroaryl and heterocycloalkyl are optionally each independently additionally substituted with C$_{1-6}$alkyl, halogen, diC$_{1-6}$alkylamino or C$_{1-6}$alkoxy.

4. The compound of claim 1, wherein Y is

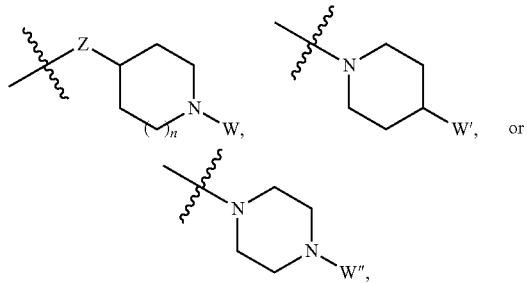

wherein,
Z is O or NR$^2$; wherein R$^2$ is H, methyl or ethyl;
n is 1;
W is —C(O)—C$_{1-6}$ alkyl, —C(O)—C$_{6-14}$ aryl, —C(O)—C$_{1-13}$ heteroaryl, —C(O)$_2$—C$_{1-6}$ alkyl, —C(O)$_2$—C$_{6-14}$ aryl or C$_{1-13}$ heteroaryl, wherein said aryl and heteroaryl are optionally each independently substituted with a C$_{1-6}$ alkyl, a halogen, a C$_{1-6}$ alkoxy, or a C$_{3-8}$ cycloalkyl;

W' is —C$_{1-5}$ heteroaryl, wherein said heteroaryl is optionally substituted with a C$_{1-6}$ alkyl, a halogen, a C$_{1-6}$ alkoxy, or C$_{3-8}$ cycloalkyl; and W" is —C(O$_2$)—C$_{1-6}$ alkyl or C$_{1-5}$ heteroaryl, wherein said heteroaryl is optionally substituted with a C$_{1-6}$ alkyl, a halogen, a C$_{1-6}$ alkoxy, or a C$_{3-8}$ cycloalkyl.

5. The compound of claim 4, wherein said aryl is phenyl, said heteroaryl is pyrrolyl, imidazolyl, pyrazolyl, triazolyl, tetrazolyl, oxadiazolyl, thiazolyl, pyridinyl or pyrimidinyl, and said heterocycloalkyl is pyrrolidinyl, piperidinyl, piperazinyl, or morpholinyl, and wherein said aryl, heteroaryl and heterocycloalkyl are optionally each independently additionally substituted with C$_{1-6}$ alkyl, halogen, diC$_{1-6}$ alkylamino, C$_{1-6}$ alkoxy, C$_{3-8}$ cycloalkyl or C$_{6-14}$ aryl.

6. The compound of claim 1, wherein said bicyclic heteroaryl compound of formula (I) is selected from the group consisting of:

1) 3-cyclopropyl-5-(1-(7-(4-methanesulfonyl-phenyl)thieno[3,2-d]pyrimidin-4-yl)piperidin-4-yl)-1,2,4-oxadiazole;
2) 3-ethyl-5-(1-(7-(4-methanesulfonyl-phenyl)thieno[3,2-d]pyrimidin-4-yl)piperidin-4-yl)-1,2,4-oxadiazole;
3) 3-isopropyl-5-(1-(7-(4-methanesulfonyl-phenyl)thieno[3,2-d]pyrimidin-4-yl)piperidin-4-yl)-1,2,4-oxadiazole;
4) 3-cyclopentyl-5-(1-(7-(4-methanesulfonyl-phenyl)thieno[3,2-d]pyrimidin-4-yl)piperidin-4-yl)-1,2,4-oxadiazole;
5) 3-cyclohexyl-5-(1-(7-(4-methanesulfonyl-phenyl)thieno[3,2-d]pyrimidin-4-yl)piperidin-4-yl)-1,2,4-oxadiazole;
6) 5-(1-(7-(4-(methanesulfonylphenyl)phenyl)thieno[3,2-d]pyrimidin-4-yl)piperidin-4-yl)-3-phenyl-1,2,4-oxadiazole;
7) 3-isopropyl-5-(4-(7-(4-methanesulfonyl-phenyl)thieno[3,2-d]pyrimidin-4-yl) piperazin-1-yl)-1,2,4-oxadiazole;
8) tert-butyl 4-(7-(4-methanesulfonyl-phenyl)thieno[3,2-d]pyrimidin-4-yl)piperazin-1-carboxylate;
9) 4-(4-(5-ethylpyrimidin-2-yl) piperazin-1-yl)-7-(4-methanesulfonyl-phenyl)thieno[3,2-d]pyrimidine;
10) 7-(2-fluoro-4-methanesulfonyl-phenyl)-4-[4-(3-isopropyl-[1,2,4]oxadiazol-5-yl)-piperidin-4-yl]-thieno[3,2-d]pyrimidine;
11) 7-(3-fluoro-4-methanesulfonyl-phenyl)-4-[4-(3-isopropyl-[1,2,4]oxadiazol-5-yl)-piperidin-4-yl]-thieno[3,2-d]pyrimidine;
12) 4-[4-(3-isopropyl-[1,2,4]oxadiazol-5yl)-piperidin-1-yl]-7-(4-nitro-phenyl)-thieno[3,2-d]pyrimidine;
13) 4-{4-[4-(3-isopropyl-[1,2,4]oxadiazol-5yl)-piperidin-1-yl]-thieno[3,2-d]pyrimidin-7-yl}-benzoic acid;
14) 4-{4-[4-(3-isopropyl-[1,2,4]oxadiazol-5yl)-piperidin-1-yl]-thieno[3,2-d]pyrimidin-7-yl}-benzoic acid methyl ester;
15) 4-[4-(3-tert-butyl-[1,2,4]oxadiazol-5yl)-piperidin-1-yl]-7-(2-fluoro-4-methanesulfonyl-phenyl)-thieno[3,2-d]pyrimidine;
16) 4-[4-(3-cyclopropyl-[1,2,4]oxadiazol-5yl)-piperidin-1-yl]-7-(2-fluoro-4-methanesulfonyl-phenyl)-thieno[3,2-d]pyrimidine;
17) 4-[4-(3-cyclopentyl-[1,2,4]oxadiazol-5yl)-piperidin-1-yl]-7-(2-fluoro-4-methanesulfonyl-phenyl)-thieno[3,2-d]pyrimidine;

18) 4-[4-(3-isopropyl-[1,2,4]oxadiazol-5yl)-piperidin-1-yl]-7-(4-(propylsulfonyl)phenyl)-thieno[3,2-d]pyrimidine;
19) 7-(4-(cyclopropylsulfonyl)phenyl)-4-[4-(3-isopropyl-[1,2,4]oxadiazol-5-yl)-piperidin-1-yl]-thieno[3,2-d]pyrimidine;
20) 4-[4-(3-isopropyl-[1,2,4]oxadiazol-5yl)-piperidin-1-yl]-7-(4-(isopropylsulfonyl)phenyl)-thieno[3,2-d]pyrimidine;
21) 7-(4-(cyclopentylsulfonyl)phenyl)-4-[4-(3-isopropyl-[1,2,4]oxadiazol-5-yl)-piperidin-1-yl]-thieno[3,2-d]pyrimidine;
22) 7-4-(2-fluoro-(4-propylsulfonyl)phenyl)-4-[4-(3-isopropyl-[1,2,4]oxadiazol-5-yl)-piperidin-1-yl]-thieno[3,2-d]pyrimidine;
23) tert-butyl 4-(5-methyl-7-(4-methanesulfonyl-phenyl)-5H-pyrrolo[3,2-d]pyrimidin-4-yloxy)piperidin-1-carboxylate;
24) 5-methyl-7-(4-methanesulfonyl-phenyl)-4-(piperidin-4-yloxy)-5H-pyrrolo[3,2-d]pyrimidine;
25) 4-(1-(5-ethylpyrimidin-2-yl)piperidin-4-yloxy)-5-methyl-7-(4-methanesulfonyl-phenyl)-5H-pyrrolo[3,2-d]pyrimidine;
26) 5-methyl-7-(4-methanesulfonyl-phenyl)-4-(1-(5-(trifluoromethyl)pyrimidin-2-yl)piperidin-4-yloxy)-5H-pyrrolo[3,2-d]pyrimidine;
27) 4-(1-(5-ethylpyrimidin-2-yl)piperidin-4-yloxy)-7-(2-fluoro-4-methanesulfonyl-phenyl)-5-methyl-5H-pyrrolo[3,2-d]pyrimidine;
28) 7-(2-fluoro-4-(methanesulfonyl(phenyl)-5-methyl-4-(1-(5-propylpyrimidin-2-yl)piperidin-4-yloxy)-5H-pyrrolo[3,2-d]pyrimidine;
29) 7-(2-fluoro-4-methanesulfonyl-phenyl)-5-methyl-4-(1-(5-(trifluoromethyl)pyrimidin-2-yl)piperidin-4-yloxy)-5H-pyrrolo[3,2-d]pyrimidine;
30) 5-ethyl-4-(1-(5-ethylpyrimidin-2-yl)piperidin-4-yloxy)-7-(4-methanesulfonyl-phenyl)-5H-pyrrolo[3,2-d]pyrimidine;
31) 5-ethyl-4-(1-(5-ethylpyrimidin-2-yl)piperidin-4-yloxy)-7-(2-fluoro-4-methanesulfonyl-phenyl)-5H-pyrrolo[3,2-d]pyrimidine;
32) 5-ethyl-7-(2-fluoro-4-methanesulfonyl-phenyl)-4-(1-(5-propylpyrimidin-2-yl)piperidin-4-yloxy)-5H-pyrrolo[3,2-d]pyrimidine;
33) 3-isopropyl-5-(4-(5-methyl-7-(4-methanesulfonyl-phenyl)-5H-pyrrolo[3,2-d]pyrimidin-4-yloxy)piperidin-1-yl)-1,2,4-oxadiazole;
34) 5-(4-(7-(2-fluoro-4-methanesulfonyl-phenyl)-5-methyl-5H-pyrrolo[3,2-d]pyrimidin-4-yloxy)piperidin-1-yl)-3-isopropyl-1,2,4-oxadiazole;
35) 5-(4-(5-ethyl-7-(2-fluoro-4-methanesulfonyl-phenyl)-5H-pyrrolo[3,2-d]pyrimidin-4-yloxy)piperidin-1-yl)-3-isopropyl-1,2,4-oxadiazole;
36) 4-[1-(3-isopropyl-[1,2,4]oxadiazol-5-yl)-pyrrolidin-3-yloxy]-7-(4-methanesulfonyl-phenyl)-5-methyl-5H-pyrrolo[3,2-d]pyrimidine;
37) 4-[1-(5-ethylpyrimidin-2-yl)-pyrrolidin-3-yloxy]-7-)4-methanesulfonyl-phenyl)-5-methyl-5H-pyrrolo[3,2-d]pyrimidine;
38) 4-[7-(4-methanesulfonyl-phenyl)-5-methyl-5H-pyrrolo[3,2-d]pyrimidin-4-yloxy]piperidin-1-carboxylic acid tert-butylamide;
39) 4-(4-(1-(3-isopropyl-1,2,4-oxadiazol-5-yl)piperidin-4-yloxy)-5-methyl-5H-pyrrolo[3,2-d]piperidin-7-yl) benzeneamine;
40) 3-isopropyl-5-(4-(5-methyl-7-(4-nitrophenyl)-5H-pyrrolo[3,2-d]pyrimidin-4-yloxy)piperidin-1-yl)-1,2,4-oxadiazole;
41) 4-{4-[1-(5-ethylpyrimidin-2-yl)-piperidin-4-yloxy]-5-methyl-5H-pyrrolo[3,2-d]pyrimidin-7-yl}-benzonitrile;
42) 1-(4-{4-[1-(5-ethylpyrimidin-2-yl)-piperidin-4-yloxy]-5-methyl-5H-pyrrolo[3,2-d]pyrimidin-7-yl}-phenyl)-ethanone;
43) 4-(1-isopropyl-piperidin-4-yloxy)-7-(4-methanesulfonyl-phenyl)-5-methyl-5H-pyrrolo[3,2-d]pyrimidine;
44) 1-{4-[7-(4-methanesulfonyl-phenyl)-5-methyl-5H-pyrrolo[3,2-d]pyrimidin-4-yloxy]-piperidin-1-yl}-2,2-dimethynyl-propan-1-one;
45) tert-butyl 4-(7-(6-fluoropyridin-3-yl)-5-methyl-5H-pyrrolo[3,2-d]pyrimidin-4-yloxy)piperidin-1-carboxylate;
46) 4-(1-(5-ethylpyrimidin-2-yl)piperidin-4-yloxy)-7-(6-fluoropyridin-3-yl)-5-methyl-5H-pyrrolo[3,2-d]pyrimidine;
47) 4-((1-(5-ethylpyrimidin-2-yl)piperidin-4-yl)methoxy)-5-methyl-7-(4-methanesulfonyl-phenyl)-5H-pyrrolo[3,2-d]pyrimidine;
48) tert-butyl 4-(7-(4-methanesulfonyl-phenyl)thieno[3,2-d]pyrimidin-4-yloxy)piperidin-1-carboxylate;
49) 3-isopropyl-5-(4-(5-methyl-7-(4-methanesulfonyl-phenyl)-5H-thieno[3,2-d]pyrimidin-4-yloxy)piperidin-1-yl)-1,2,4-oxadiazole;
50) 3-(cyclopropylmethyl)-5-(4-(7-(4-methanesulfonyl-phenyl)thieno[3,2-d]pyrimidin-4-yloxy)piperidin-1-yl)-1,2,4-oxadiazole;
51) 3-tert-butyl-5-(4-(7-(4-methanesulfonyl-phenyl)thieno[3,2-d]pyrimidin-4-yloxy)piperidin-1-yl)-1,2,4-oxadiazole;
52) 3-cyclobutyl-5-(4-(7-(4-methanesulfonyl-phenyl)thieno[3,2-d]pyrimidin-4-yloxy)piperidin-1-yl)-1,2,4-oxadiazole;
53) 4-(1-(5-ethylpyrimidin-2-yl)piperidin-4-yloxy)-7-(4-methanesulfonyl-phenyl)thieno[3,2-d]pyrimidine;
54) 4-[1-(5-cyclopropyl-pyrimidin-2-yl)-piperidin-4-yloxy]-7-(4-methanesulfonyl-phenyl)-thieno[3,2-d]pyrimidine;
55) 4-[1-(5-ethyl-pyrimidin-2-yl)-pyrrolidin-3-yloxy]-7-(4-methanesulfonyl-phenyl)-thieno[3,2-d]pyrimidine;
56) 4-[1-(3-isopropyl-[1,2,4]oxadiazol-5-yl)-pyrrolidin-3-yloxy]-7-(4-methanesulfonyl-phenyl)-thieno[3,2-d]pyrimidine;
57) 7-(4-((methanesulfony)phenyl)-4-(1-(4-(trifluoromethyl)pyrimidin-2-yl)piperidin-4-yloxy) thieno[3,2-d]pyrimidine;
58) 7-(2-fluoro-4-methanesulfonyl-phenyl)-4-[1-(3-isopropyl-[1,2,4]oxadiazol-5-yl)piperidin-4-yloxy]thieno[3,2-d]pyrimidine;
59) 3-ethyl-5-(4-(7-(2-fluoro-4-methanesulfonyl-phenyl)thieno[3,2-d]pyrimidin-4-yloxy)piperidin-1-yl)-1,2,4-oxadiazole;
60) 3-sec-butyl-5-(4-(7-(2-fluoro-4-methanesulfonyl-phenyl)thieno[3,2-d]pyrimidin-4-yloxy)piperidin-1-yl)-1,2,4-oxadiazole;
61) 7-(2-fluoro-4-methanesulfonyl-phenyl)-4-[1-(3-cyclopropyl-[1,2,4]oxadiazol-5-yl)piperidin-4-yloxy]thieno[3,2-d]pyrimidine;
62) 5-(4-(7-(2-fluoro-4-methanesulfonyl-phenyl)thieno[3,2-d]pyrimidin-4-yloxy)piperidin-1-yl)-3-phenyl-1,2,4-oxadiazole;

63) 5-(4-(7-(2-fluoro-4-methanesulfonyl-phenyl)thieno[3,2-d]pyrimidin-4-yloxy)piperidin-1-yl)-3-(4-fluorophenyl)-1,2,4-oxadiazole;
64) 5-(4-(7-(2-fluoro-4-methanesulfonyl-phenyl)thieno[3,2-d]pyrimidin-4-yloxy)piperidin-1-yl)-3-(pyridin-4-yl)-1,2,4-oxadiazole;
65) 5-(4-(7-(2-fluoro-4-methanesulfonyl-phenyl)thieno[3,2-d]pyrimidin-4-yloxy)piperidin-1-yl)-3-(pyridin-3-yl)-1,2,4-oxadiazole;
66) 5-(4-(7-(2-fluoro-4-methanesulfonyl-phenyl)thieno[3,2-d]pyrimidin-4-yloxy)piperidin-1-yl)-3-(pyrazin-2-yl)-1,2,4-oxadiazole;
67) 7-(2-fluoro-4-methanesulfonyl-phenyl)-4-[1-(3-cyclopropylmethyl-[1,2,4]oxadiazol-5-yl)piperidin-4-yloxy]thieno[3,2-d]pyrimidine;
68) 7-(2-fluoro-4-methanesulfonyl-phenyl)-4-[1-(3-cyclopentyl-[1,2,4]oxadiazol-5-yl)piperidin-4-yloxy]thieno[3,2-d]pyrimidine;
69) 7-(2-fluoro-4-methanesulfonyl-phenyl)-4-[1-(3-t-butyl-[1,2,4]oxadiazol-5-yl)piperidin-4-yloxy]thieno[3,2-d]pyrimidine;
70) tert-butyl 4-(7-(2-fluoro-4-methanesulfonyl-phenyl)thieno[3,2-d]pyrimidin-4-yloxy)piperidin-1-carboxylate;
71) isopropyl 4-(7-(2-fluoro-4-methanesulfonyl-phenyl)thieno[3,2-d]pyrimidin-4-yloxy)piperidine-1-carboxylate;
72) 7-(2-fluoro-4-methanesulfonyl-phenyl)-4-[1-methylpiperidin-4-yloxy]thieno[3,2-d]pyrimidine;
73) 4-(7-(2-fluoro-4-methanesulfonyl-phenyl)thieno[3,2-d]pyrimidin-4-yloxy)piperidin-1-carbonitrile;
74) 7-(2-fluoro-4-methanesulfonyl-phenyl)-4-[piperidin-4-yloxy]thieno[3,2-d]pyrimidine;
75) 2-(4-(7-(2-fluoro-4-methanesulfonyl-phenyl)thieno[3,2-d]pyrimidin-4-yloxy)piperidin-1-yl)benzo[d]oxazole;
76) 7-(2-fluoro-4-methanesulfonyl-phenyl)-4-[1-(3-isobutyl-[1,2,4]oxadiazol-5-yl)piperidin-4-yloxy]thieno[3,2-d]pyrimidine;
77) 7-(2-fluoro-4-methanesulfonyl-phenyl)-4-[1-(3-cyclohexyl-[1,2,4]oxadiazol-5-yl)piperidin-4-yloxy]thieno[3,2-d]pyrimidine;
78) 7-(2-fluoro-4-methanesulfonyl-phenyl)-4-[1-(3-bicyclo[2,2,1]heptan-2-yl[1,2,4]oxadiazol-5-yl)piperidin-4-yloxy]thieno[3,2-d]pyrimidine;
79) 4-[1-(5-ethyl-pyrimidin-2-yl)-piperidin-4-yloxy]-7-(2-fluoro-4-methanesulfonyl-phenyl)-thieno[3,2-d]pyrimidine;
80) 7-(2-fluoro-4-methanesulfonyl-phenyl)-4-[1-(5-trifluoromethyl-pyrimidin-2-yl)-piperidin-4-yloxy]-thieno[3,2-d]pyrimidine;
81) 7-(2-fluoro-4-methanesulfonyl-phenyl)-4-[1-(5-propyl-pyrimidin-2-yl)-piperidin-4-yloxy]-thieno[3,2-d]pyrimidine;
82) 7-(2-fluoro-4-methanesulfonyl-phenyl)-4-[1-(5-cyclopropyl-pyrimidin-2-yl)-piperidin-4-yloxy]-thieno[3,2-d]pyrimidine;
83) 7-(2-fluoro-4-methanesulfonyl-phenyl)-4-(1-pyrimidin-2-yl-piperidin-4-yloxy)-thieno[3,2-d]pyrimidine;
84) 7-(2-fluoro-4-methanesulfonyl-phenyl)-4-{1-[5-(4-isopropylphenyl)-pyrimidin-2-yl)-piperidin-4-yloxy]-thieno[3,2-d]pyrimidine;
85) 1-(4-(7-(2-fluoro-4-methanesulfonyl-phenyl)thieno[3,2-d]pyrimidin-4-yloxy)piperidin-1-yl)ethanone;
86) 1-(4-(7-(2-fluoro-4-methanesulfonyl-phenyl)thieno[3,2-d]pyrimidin-4-yloxy)piperidin-1-yl)-2,2-dimethylpropan-1-one;
87) {4-[7-(2-fluoro-4-methanesulfonyl-phenyl)-thieno[3,2-d]pyrimidin-4-yloxy]-piperidin-1-yl}phenyl-methanone;
88) {4-[7-2-fluoro-4-methanesulfonyl-phenyl]-thieno[3,2-d]pyrimidin-4-yloxy]-piperidin-1-yl}pyridin-3-yl-methanone;
89) 4-(1-benzylpiperidin-4-yloxy]-7-(2-fluoro-4-methanesulfonyl-phenyl) thieno[3,2-d]pyrimidine;
90) 4-(4-bromo-1-benzyl-piperidin-4-yloxy]-7-(2-fluoro-4-methanesulfonyl-phenyl) thieno[3,2-d]pyrimidine;
91) 7-(2-fluoro-4-methanesulfonyl-phenyl)-4-[1-(4-isopropyl-thiazol-2-yl)piperidin-4-yloxy]-thieno[3,2-d]pyrimidine;
92) 7-(2-fluoro-4-methanesulfonyl-phenyl)-4-(1-(2-isopropyl-2H-tetrazol-5-yl)piperidin-4-yloxy)thieno[3,2-d]pyrimidine;
93) 7-(2-fluoro-4-methanesulfonyl-phenyl)-4[1-(5-isopropyl-[1,2,4]oxadiazol-3-yl)-piperidin-4-yloxy]-thieno[3,2-d]pyrimidine;
94) 5-(4-(7-(2-chloro-4-methoxyphenyl)thieno[3,2-d]pyrimidin-4-yloxy)piperidin-1-yl)-3-isopropyl-1,2,4-oxadiazole;
95) 4-[1-(3-isopropyl-[1,2,4]oxadiazol-5yl)-piperidin-4-yloxy]-7-(2,3,4-trifluoro-phenyl)-thieno[3,2-d]pyrimidine;
96) 7-(3-fluoro-4-methoxy-phenyl)-4-[1-(3-isopropyl-[1,2,4]oxadiazol-5-yl)-piperidin-4-yloxy]-thieno[3,2-d]pyrimidine;
97) 4-[1-(3-isopropyl-[1,2,4]oxadiazol-5yl)-piperidin-4-yloxy]-7-(4-trifluoromethoxy-phenyl)-thieno[3,2-d]pyrimidine;
98) 4-[1-(3-isopropyl-[1,2,4]oxadiazol-5yl)-piperidin-4-yloxy]-7-(4-trifluoromethylsulfanyl-phenyl)-thieno[3,2-d]pyrimidine;
99) 7-(2-fluoro-4-trifluoro(methanesulfony)phenyl)-4-[1-(3-isopropyl-[1,2,4]oxadiazol-5-yl)-piperidin-4-yloxy]-thieno[3,2-d]pyrimidine;
100 4-{4-[1-(3-isopropyl-[1,2,4]oxadiazol-5yl)-piperidin-4-yloxy]-thieno[3,2-d]pyrimidin-7-yl}-benzoic acid methyl ester;
101) 1-(4-{4-[1-(3-isopropyl-[1,2,4]oxadiazol-5yl)-piperidin-4-yloxy]-thieno[3,2-d]pyrimidin-7-yl}-phenyl)-ethanone;
102) 7-(4-cyclopropylsulfonyl-phenyl)-4-[1-(3-isopropyl-[1,2,4]oxadiazol-5-yl)-piperidin-4-yloxy]-thieno[3,2-d]pyrimidine;
103) 4-[1-(3-isopropyl-[1,2,4]oxadiazol-5yl)-piperidin-4-yloxy]-7-(4-isopropylsulfonyl-phenyl)-thieno[3,2-d]pyrimidine;
104) 4-[1-(3-isopropyl-[1,2,4]oxadiazol-5yl)-piperidin-4-yloxy]-7-(4-propylsulfonyl-phenyl)-thieno[3,2-d]pyrimidine;
105) 7-(2-fluoro-(4-propylsulfonyl)-phenyl)-4-[1-(3-isopropyl-[1,2,4]oxadiazol-5-yl)-piperidin-4-yloxy]-thieno[3,2-d]pyrimidine;
106) 7-(4-cyclopentylsulfonyl-phenyl)-4-[1-(3-isopropyl-[1,2,4]oxadiazol-5-yl)-piperidin-4-yloxy]-thieno[3,2-d]pyrimidine;
107) tert-butyl 4-(7-(4-methanesulfonyl-phenyl)thieno[3,2-d]pyrimidin-4-ylamino)piperidin-1-carboxylate;
108) 7-(4-methanesulfonyl-phenyl)-N-(piperidin-4-yl)thieno[3,2-d]pyrimidin-4-amine;
109) N-(1-(5-ethylpyrimidin-2-yl)piperidin-4-yl)-7-(4-methanesulfonyl-phenyl)thieno[3,2-d]pyrimidin-4-amine;

110) tert-butyl 4-(methyl(7-(4-methanesulfonyl-phenyl)thieno[3,2-d]pyrimidin-4-yl)amino)piperidin-1-carboxylate;
111) N-(1-(5-isopropyl-1,2,4-oxadiazol-3-yl)piperidin-4-yl)-N-methyl-7-(4-methanesulfonyl-phenyl) thieno[3,2-d]pyrimidin-4-amine;
112) [1-(5-ethylpyrimidin-2-yl)-piperidin-4-yl]-[7-(4-methanesulfonyl-phenyl)-thieno[3,2-d]pyrimidin-4-yl]-methylamine;
113) ethyl-[7-(4-methanesulfonyl-phenyl)-thieno[3,2-d]pyrimidin-4-yl]-(5'-trifluoromethyl-3,4,5,6-tetrahydro2H-[1,2']bipyridinyl-4-yl)amine;
114) tert-butyl 4-(5-methyl-7-(4-methanesulfonyl-phenyl)-5H-pyrrolo[3,2-d]pyrimidin-4-ylamino)piperidin-1-carboxylate;
115) 3-isopropyl-5-(1-(5-methyl-7-(4-methanesulfonyl-phenyl)-5H-pyrrolo[3,2-d]pyrimidin-4-yl)piperidin-4-yl)-1,2,4-oxadiazole;
116) 5-(1-(7-(4-(1H-tetrazol-1-yl)phenyl)thieno[3,2-d]pyrimidin-4-yl)piperidin-4-yl)-3-isopropyl-1,2,4-oxadiazole;
117) 5-(4-(7-(4-(1H-1,2,4-triazol-1-yl)phenyl) thieno[3,2-d]pyrimidin-4-yloxy)piperidin-1-yl)-3-tert-butyl-1,2,4-oxadiazole;
118) tert-butyl 4-(7-(4-(1H-tetrazol-1-yl)phenyl)-5-methyl-5H-pyrrolo[3,2-d]pyrimidin-4-yloxy)piperidin-1-carboxylate;
119) 4-(4-(1-(5-ethylpyrimidin-2-yl)piperidin-4-yloxy)-5-methyl-5H-pyrrolo[3,2-d]pyrimidin-7-yl)benzeneamine;
120) 7-(4-(1H-tetrazol-1-yl)phenyl)-4-(1-(5-ethylpyrimidin-2-yl)piperidin-4-yloxy)-5-methyl-5H-pyrrolo[3,2-d]pyrimidine;
121) 7-(4-(1H-tetrazol-1-yl)phenyl)-5-methyl-4-(1-(5-(trifluoromethyl)pyrimidin-2-yl)piperidin-4-yloxy)-5H-pyrrolo[3,2-d]pyrimidine;
122) (S)-tert-butyl 3-[5-methyl-7-(4-amino-phenyl)-5H-pyrrolo[3,2-d]pyrimidin-4-yloxy)pyrrolidin-1-carboxylate; and
123) (5)-tert-butyl 3-[5-methyl-7-(4-tetrazol-1-yl-phenyl)-5H-pyrrolo[3,2-d]pyrimidin-4-yloxy)pyrrolidin-1-carboxylate.

7. A pharmaceutical composition comprising the compound of claim 1 and a pharmaceutical acceptable carrier.

8. A method for treating a disease selected from the group consisting of diabetes, hyperglycemia, glucose tolerance impairment, insulin resistance, hyperinsulinemia, metabolic syndrome, obesity, dyslipidemia, hyperlipidemia, hypertriglyceridemia, hypercholesterolemia, low HDL and high HDL, which method comprises administering the compound of claim 1 to a mammal in need thereof.

* * * * *